US012678793B2

(12) United States Patent
Mei et al.

(10) Patent No.: US 12,678,793 B2
(45) Date of Patent: Jul. 14, 2026

(54) CARTRIDGE AND TESTING DEVICE

(71) Applicant: GUANGZHOU WONDFO BIOTECH CO., LTD., Guangzhou (CN)

(72) Inventors: Zhe Mei, Guangzhou (CN); Chuhao Jia, Guangzhou (CN); Tong Zhang, Guangzhou (CN)

(73) Assignee: GUANGZHOU WONDFO BIOTECH CO., LTD., Guangzhou (CN)

( * ) Notice: Subject to any disclaimer, the term of this patent is extended or adjusted under 35 U.S.C. 154(b) by 1062 days.

(21) Appl. No.: 17/750,521

(22) Filed: May 23, 2022

(65) Prior Publication Data

US 2022/0371019 A1 Nov. 24, 2022

Related U.S. Application Data

(60) Provisional application No. 63/191,368, filed on May 21, 2021.

(30) Foreign Application Priority Data

Sep. 30, 2021 (CN) .......................... 202111169089.0
Sep. 30, 2021 (CN) .......................... 202122409807.9

(51) Int. Cl.
   *B01L 7/00* (2006.01)
   *B01L 3/00* (2006.01)
   (Continued)

(52) U.S. Cl.
   CPC ........... *B01L 7/52* (2013.01); *B01L 3/502707* (2013.01); *B01L 3/502738* (2013.01);
   (Continued)

(58) Field of Classification Search
   CPC ................. B01L 7/52; B01L 3/502707; B01L 3/502738; B01L 2200/0689;
   (Continued)

(56) References Cited

U.S. PATENT DOCUMENTS

2004/0185554 A1* 9/2004 Daitch ................. G01N 1/2273
                                                       73/202.5
2005/0045538 A1* 3/2005 Seto ..................... G01N 35/026
                                                       422/534

(Continued)

OTHER PUBLICATIONS

Extended European Search Report of counterpart European Patent Application No. 22174632.4 issued on Oct. 24, 2022.

*Primary Examiner* — Charles Capozzi
*Assistant Examiner* — Jacqueline Brazin

(57) ABSTRACT

The present invention relates to the field of biomedical technology and discloses a cartridge and a testing device. The cartridge comprises a sample lysis compartment, a first sample mixing compartment and a first PCR compartment; a first valve is disposed between the sample lysis compartment and the first sample mixing compartment, the first valve controls the flowing or blocking of the sample between the sample lysis compartment and the first sample mixing compartment; a fourth valve is disposed between the first PCR compartment and the first sample mixing compartment, the fourth valve controls the flow or blocking of the sample between the first sample mixing compartment and the first PCR compartment; a first reagent is provided in the first sample mixing compartment. In the compartment, nucleic acids in the sample mix with the first reagent and is then sent to the first PCR compartment for amplification.

26 Claims, 23 Drawing Sheets

(51) Int. Cl.
    *C12Q 1/6806*      (2018.01)
    *C12Q 1/686*       (2018.01)

(52) U.S. Cl.
    CPC ........... *C12Q 1/6806* (2013.01); *C12Q 1/686* (2013.01); *B01L 2200/0689* (2013.01); *B01L 2200/16* (2013.01); *B01L 2300/041* (2013.01); *B01L 2300/0681* (2013.01); *B01L 2300/087* (2013.01); *B01L 2400/043* (2013.01)

(58) Field of Classification Search
    CPC ........... B01L 2200/16; B01L 2300/041; B01L 2300/0681; B01L 2300/087; B01L 2400/043; B01L 2200/028; B01L 2200/141; B01L 2300/043; B01L 2300/0816; B01L 2400/0638; B01L 2400/0644; B01L 3/502761; C12Q 1/6806; C12Q 1/686
    USPC ....................................................... 435/288.5
    See application file for complete search history.

(56) References Cited

U.S. PATENT DOCUMENTS

| | | | |
|---|---|---|---|
| 2012/0308445 A1* | 12/2012 | Roper .................... | G01N 1/312 |
| | | | 210/322 |
| 2015/0321193 A1* | 11/2015 | Sprague .............. | F16K 99/0015 |
| | | | 264/553 |
| 2015/0353919 A1 | 12/2015 | Mielke et al. | |
| 2018/0274824 A1* | 9/2018 | Holzwanger ......... | F25D 29/001 |
| 2019/0256890 A1* | 8/2019 | Eberhart .......... | G01N 27/44791 |

* cited by examiner

CARTRIDGE AND TESTING DEVICE

CROSS REFERENCE TO RELATED APPLICATIONS

The present application claims the benefit of U.S. Provisional Patent Application No. 63/191,368 filed on May 21, 2021, and Chinese Patent Application Nos. 202111169089.0 and 202122409807.9 filed on Sep. 30, 2021, the contents of which are hereby incorporated by reference.

FIELD OF THE INVENTION

The present invention relates to the field of biomedical technology, particularly relates to a cartridge and a testing device.

BACKGROUND OF THE INVENTION

Nucleic acid detection plays a very important role in many biochemical analysis fields, and has been widely used in the biomedical field.

The method of centrifuge columns or magnetic beads has been usually used in the prior art for nucleic acid extraction, which generally requires four steps of lysis, binding, washing, and elution, plus subsequent steps of nucleic acid molecule hybridization, polymerase chain reaction (PCR), and biochips, making the entire "sample to result" fully automated assay device very difficult to achieve. In terms of the transfer of the active ingredients in each step, most of the existing technologies use manual transfer, which is not only cumbersome, time-consuming, and labor-intensive, but also difficult to adequately and efficiently transfer those ingredients, and the manual operation will easily lead to unstable results and make the testing difficult to achieve.

In addition, the mainstream technology of molecular detection is fluorescence quantitative PCR technology. Due to the exponential amplification of templates in PCR technology, the existing open consumable materials make the whole operation process prone to PCR aerosol contamination, which affects the purity of extracts, thus limiting the further clinical application of fluorescence quantitative PCR technology.

Molecular detection in the prior art mainly relies on manual operation, resulting in unstable results, low accuracy, and low detection efficiency.

Therefore, the prior art is in urgent need of improvement.

SUMMARY OF THE INVENTION

The objective of the present invention is to provide a cartridge and a testing device, to solve technical problems that exist in the prior art of relying on manual operation, resulting in unstable detection results, low accuracy, and low detection efficiency.

To achieve the above-mentioned objectives, the present invention provides a cartridge, the cartridge comprises a sample lysis compartment, a first sample mixing compartment and a first PCR compartment;

A first valve is provided between the sample lysis compartment and the first sample mixing compartment, and the first valve is used to control the flow or blocking of a sample between the sample lysis compartment and the sample mixing compartment;

A fourth valve is provided between the first PCR compartment and the first sample mixing compartment, and the fourth valve is used to control the flow or blocking of the sample between the sample mixing compartment and the first PCR compartment;

The first sample mixing compartment is provided with a first reagent, nucleic acids in the sample mix with the first reagent in the first sample mixing compartment. In this way, the subsequent nucleic acid amplification reaction in the PCR chamber is facilitated.

In some embodiments of the present application, the cartridge further comprises a sample filtration compartment; the sample filtration compartment communicates with the first sample mixing compartment; the first valve is located between the sample lysis compartment and the sample filtration compartment.

In some embodiments of the present application, a filtration film is provided in the sample filtration compartment; preferably, the filtration film is a terylene or nylon filtration film.

In some embodiments of the present application, the cartridge further comprises a first damping compartment, the first damping compartment communicates with the first PCR compartment.

In some embodiments of the present application, the cartridge further comprises a sample addition compartment, the sample addition compartment communicates with the sample lysis compartment.

In some embodiments of the present application, the first sample mixing compartment is also provided with a first mixing bead, the first mixing bead allows thorough mixing of the sample and the first reagent through its movement.

In some embodiments of the present application, the cartridge further comprises a siphon tube, and the sample addition compartment and the sample lysis compartment communicate with each other through the siphon tube.

In some embodiments of the present application, a first choke valve is provided in the siphon tube; the first choke valve is used to control the flow or blocking of the sample and/or air between the sample addition compartment and the sample lysis compartment.

In some embodiments of the present application, the cartridge further comprises a cassette sample addition nozzle, the cassette sample addition nozzle communicates with the sample addition compartment, and is used for adding the sample into the sample addition compartment.

In some embodiments of the application, the cartridge further comprises a lid, the lid can cap the cassette sample addition nozzle; the lid is provided with a step, the step and a through-hole of the cassette sample addition nozzle are in an interference fit.

In some embodiments of the present application, a plate is provided in the sample lysis compartment, the plate is used to prevent the sample from splashing when entering the sample lysis compartment and to allow a balanced force acting upon the cartridge.

In some embodiments of the present application, the first valve is disposed below the sample lysis compartment, and communicates with the bottom of the sample lysis compartment.

In some embodiments of the present application, the first reagent is a first lyophilized bead.

In some embodiments of the present application, the first lyophilized bead comprises an excipient, the weight of the excipient accounts for 20%-60% of the total weight of the first lyophilized bead.

In some embodiments of the present application, there are multiple first PCR compartments, the first sample mixing compartment respectively communicates with the multiple first PCR compartments.

In some embodiments of the present application, the cartridge further comprises a pneumatic module, the pneumatic module is used to drive sample flow between the sample lysis compartment, the first sample mixing compartment and the first PCR compartment.

In some embodiments of the present application, the pneumatic module comprises a third air hole and a ninth air hole, the third air hole communicates with the first sample mixing compartment; the first PCR compartment communicates with the ninth air hole; a first waterproof and breathable film is provided on the ninth air hole, a first waterproof and breathable film is provided on the ninth air hole, the first waterproof and breathable film allows air to discharge from the first PCR compartment while blocking liquid from flowing out of the first waterproof and breathable film; wherein the third air hole is used to communicate with a second air pump to draw or push air contained in the first sample mixing compartment.

In some embodiments of the present application, the pneumatic module further comprises a first air hole, and a first air channel is provided at the cartridge; the first air hole communicates with the first air channel, the first air channel communicates with the sample lysis compartment; the first air hole is used to communicate with the first air pump, to draw or push the air contained in the sample lysis compartment.

In some embodiments of the present application, the pneumatic module further comprises a second air hole and a first air compartment; the first air hole and the second air hole are located in the first air compartment, the first air hole communicates with the first air channel through the second air hole; the first waterproof and breathable film is sealed over the first air hole and the second air hole; a sealing film is provided at an outer side of the first waterproof and breathable film, so that the first air hole and the second air hole exchange air within the first air compartment.

In some embodiments of the present application, the cartridge further comprises a sixth valve, the ninth air hole communicates with the first PCR chamber through the sixth valve in a switchable manner.

In some embodiments of the present application, the pneumatic module further comprises a sixth air hole, the sixth air hole communicates with the first sample mixing compartment, and the sixth air hole is provided with a second waterproof and breathable film, when the first sample mixing compartment is fulfilled up, the second waterproof and breathable film can prevent the liquid from flowing out of the second waterproof and breathable film.

In some embodiments of the present application, the cartridge further comprises a fifth air hole and a second air compartment, and the fifth air hole and the sixth air hole are both located in the second air compartment. The second air compartment is provided with a sealing film, and the sealing film is located on an outer side of the second waterproof and breathable film; wherein the fifth air hole communicates with the third air hole, and the fifth air hole and the sixth air hole exchange air in the second air compartment.

In some embodiments of the present application, the pneumatic module further comprises a fourth air hole, a second air channel and a third air channel; one end of the third air hole communicates with the second air pump, one end of the second air channel communicates with the other end of the third air hole; the second air channel communicates with the third air channel through the fourth air hole; the third air channel communicates with the fifth air hole; the third air channel and one end of the third air hole that communicates with the second air pump are located at one surface of the cartridge, the second air channel and the third air channel are located at a surface opposite to the cartridge In some embodiments of the present application, the first valve and the fourth valve are both ejector valves; the ejector valve comprises a valve chamber and a rubber cushion, the bottom of the valve chamber is provided with a flow channel hole and several bulged parts, the lateral side of the valve chamber is provided with an opening; the rubber cushion is placed above the bulged parts, the bulged parts support the rubber cushion, so that a gap is formed between undeformed the rubber cushion and the flow channel hole for sample flow, the rubber cushion is used to block the flow channel hole when deformed by compression.

In some embodiments of the present application, the bulged parts comprise at least two, all the bulged parts are arranged around the flow channel hole, and the sample flows into the flow channel hole from within the gap between adjacent the bulged parts.

In some embodiments of the present application, the cartridge further comprises a second valve; the second valve is located between the sample filtration compartment and the first sample mixing compartment, and is used to control the flow or blocking of the sample between the sample filtration compartment and the first sample mixing compartment.

In some embodiments of the present application, the cartridge further comprises a second sample mixing compartment, a second PCR compartment and a fifth valve; the second sample mixing compartment respectively communicates with the sample filtration compartment and the second PCR compartment; the fifth valve is located between the second sample mixing compartment and the second PCR compartment and is used to control the flow or blocking of the sample between the second sample mixing compartment and the second PCR compartment; a second mixing bead and a second lyophilized bead are provided in the second sample mixing compartment for the second mixing bead to mix the sample and the second lyophilized bead by movement, so that the nucleic acid within the sample is sufficiently mixed with re-dissolved the second lyophilized bead; the cartridge further comprises a third valve; the third valve is located between the sample filtration compartment and the second sample mixing compartment.

In some embodiments of the present application, the cartridge comprises a cartridge body, a main sealing film, a first rubber cushion and a fourth rubber cushion; a sample lysis chamber, a first valve chamber, a first sample mixing chamber, a fourth valve chamber and a first PCR chamber are provided on the cartridge body; the sample lysis chamber, the first valve chamber, the first sample mixing chamber, the fourth valve chamber and the first PCR chamber communicate with each other in sequence; the main sealing film covers the upper surface of the cartridge body, and forms the sample lysis compartment, the first sample mixing compartment, and the first PCR compartment respectively with the sample lysis chamber, the first sample mixing chamber, and the first PCR chamber; the bottoms of the first valve chamber and the fourth valve chamber are provided with flow channel holes and several bulged parts, and the sides thereof are provided with opening; the first rubber cushion is placed above the bulged parts of the first valve chamber to form the first valve; the fourth rubber cushion is placed above the bulged parts of the fourth valve chamber to form the fourth valve.

In some embodiments of the present application, a step portion is provided on the cartridge body, the first PCR chamber and the second PCR chamber are located on the step portion; the first PCR chamber and the second PCR chamber are pass-through chambers passing through the step portion.

In some embodiments of the present application, the cartridge further comprises a second sealing film, the second sealing film covers the lower surface of the cartridge body; the main sealing film comprises a first sealing film and a third sealing film; the third sealing film covers the upper surface of the step portion; the upper surfaces of the first PCR chamber and the second PCR chamber are sealed by the third sealing film, and the lower surfaces are sealed by the second sealing film; the first sealing film forms the sample lysis compartment, the first sample mixing compartment, and the first PCR compartment respectively with the sample lysis chamber, the first sample mixing chamber, and the first PCR chamber.

In another aspect, the present invention further provides a testing device, comprising above-mentioned cartridge and a supporting instrument; the instrument comprises at least the following modules: a first driving module, which is used to drive the opening and closing of the first valve; a fourth driving module, which is used to drive the opening and closing of the fourth valve; a first magnetic module, which is used to provide magnetic force; a heating module, which is used to heat the sample mixture; a first temperature control module, which is used to provide a heating and cooling cycle; a first optical detection module, which is used to assess the amplification in a chamber.

In some embodiments of the present application, the instruments further comprise a rack, the first driving module, the fourth driving module, the first magnetic module, the heating module, the first temperature control modules are all disposed on the rack; an installation slot (2100 is provided on the rack (2000) at a position corresponding to the positions of the first driving module, the fourth driving module, the first magnetic module, the heating module, and the first temperature control module; the cartridge is vertically inserted into the installation slot.

Compared with the prior art, the cartridge and testing device of the embodiment of the present invention has the beneficial effects:

(1) The cartridge of the present embodiment is inserted into the testing device, and can be operated simply on the testing device, and can realize the automatic and integrated amplification and detection of nucleic acids, thus reducing the manual operation steps and reducing the probability of infection to the testing operators; meanwhile, it reduces the requirements for the testing operators, thus is more convenient and quick, and can be easily used by personnel without professional training, and the testing results are highly reliable and accurate.

(2) In the cartridge of the present embodiment, the up and down movement by the first mixing bead in the first sample mixing compartment accelerates the mixing of the sample and the nucleic acid detection reagent, thus improving the stability of subsequent nucleic acid amplification.

(3) The cartridge of the present embodiment does not need to perform complicated nucleic acid extraction, and can effectively shorten the total duration of nucleic acid testing, so that the total duration of nucleic acid testing is less than one hour or even 45 minutes for simultaneously complete the high-sensitivity detection of multiple targets in one sample.

BRIEF DESCRIPTION OF THE DRAWINGS

For illustrating the technical solutions in the embodiments of the present invention more clearly, the accompanying drawings that need to be used in the description of the embodiments or the prior art will be briefly introduced below. and it is obvious that the accompanying drawings in the following description are only some embodiments of the present invention, and other accompanying drawings can be obtained according to them without any creative effort for a person of ordinary skill in the art. Dashed lines in FIGS. 5-7 and 14-33 represent structures on the opposite side of the cartridge from the solid-line structures.

DETAILED DESCRIPTION OF THE INVENTION

Specific embodiments of the present invention are described in further detail below in conjunction with the accompanying drawings and embodiments. The following embodiments are used to illustrate the present invention, but are not intended to limit the scope of the invention.

In the description of the present invention, it is to be understood that the terms "on", "under", "left", "right", "top", "bottom", etc., indicate an orientation or positional relationship based on the orientation or positional relationship shown in the accompanying drawings and are intended only to facilitate and simplify the description of the invention, not to indicate or imply that the device or element referred to must have a particular orientation, be constructed and operate in a particular It is not intended to indicate or imply that the device or element referred to must have a particular orientation, be constructed and operated in a particular orientation, and therefore is not to be construed as limiting the invention.

It is to be understood that the terms "length," "width," "on", "under", "front", "back", "left", "right", "vertical", "horizontal", "top", "bottom", "inside", "outside", etc. indicate orientations or positional relationships based on those shown in the accompanying drawings and are intended only to facilitate and simplify the description of the invention, not to indicate or imply that the device or element referred to must have a particular orientation, be constructed and operated in a particular orientation, and therefore are not to be construed as limiting the invention.

In addition, the terms "first" and "second" are used for descriptive purposes only and are not to be understood as indicating or implying relative importance or implicitly specifying the number of technical features indicated. Thus, a feature qualified with "first" and "second" may explicitly or implicitly comprise one or more such features. In the description of the present invention, "plurality" means two or more, unless otherwise expressly and specifically limited.

Example 1

Figure 1:
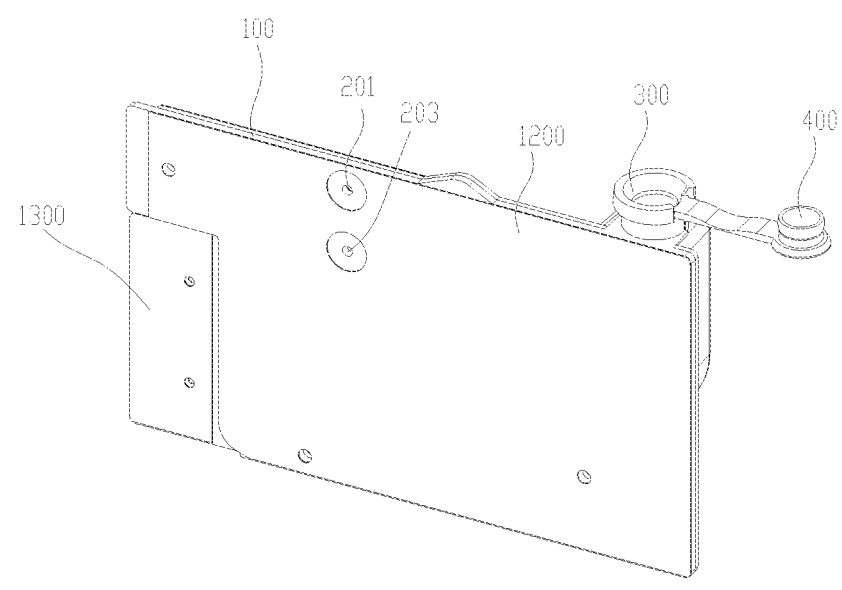
FIG. 1 is the schematic diagram of the axial side of the cartridge in Example 1 of the present invention.
Figure 5:
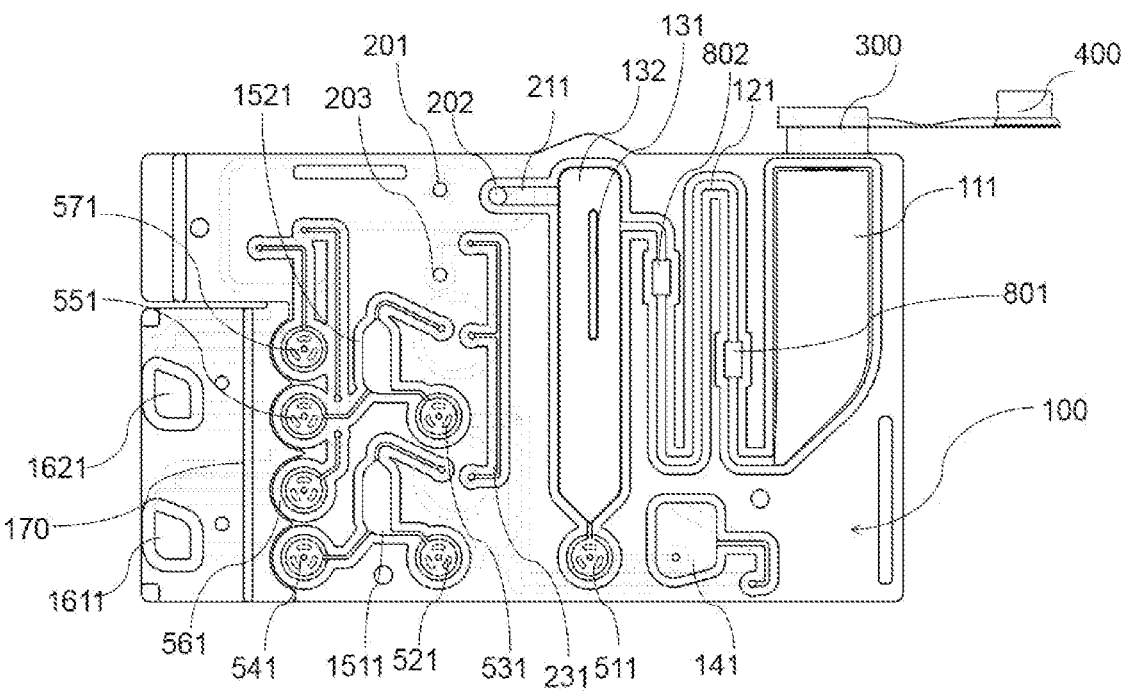
FIG. 5 is the structure schematic diagram of the front of the cartridge body of the cartridge in Example 1 of the present invention.
Figure 6:
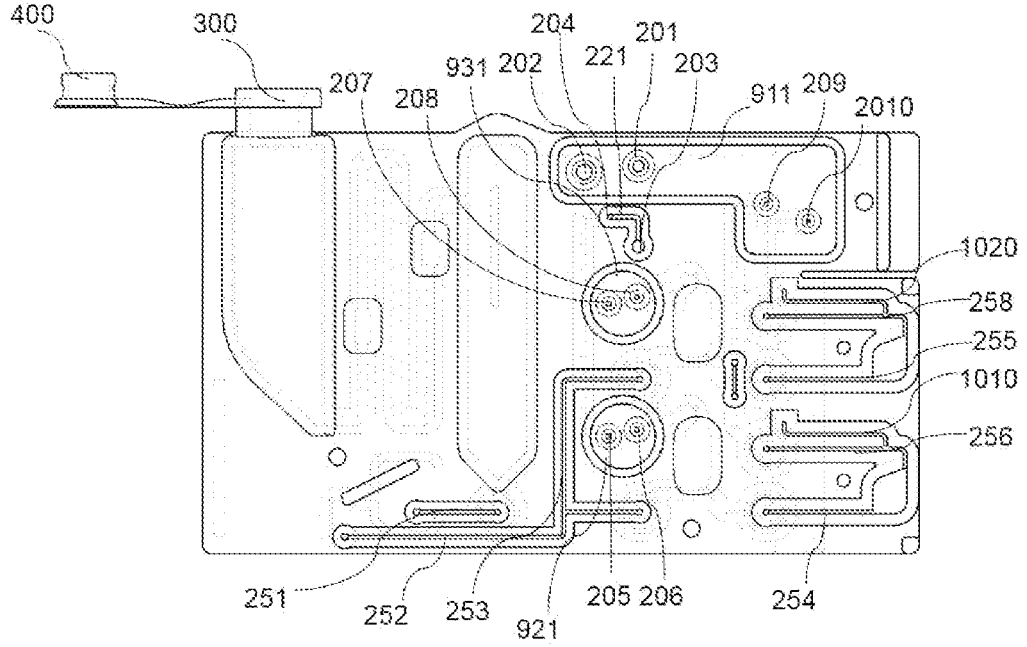
FIG. 6 is the structure schematic diagram of the back of the cartridge body of the cartridge in Example 1 of the present invention.
Figure 7:
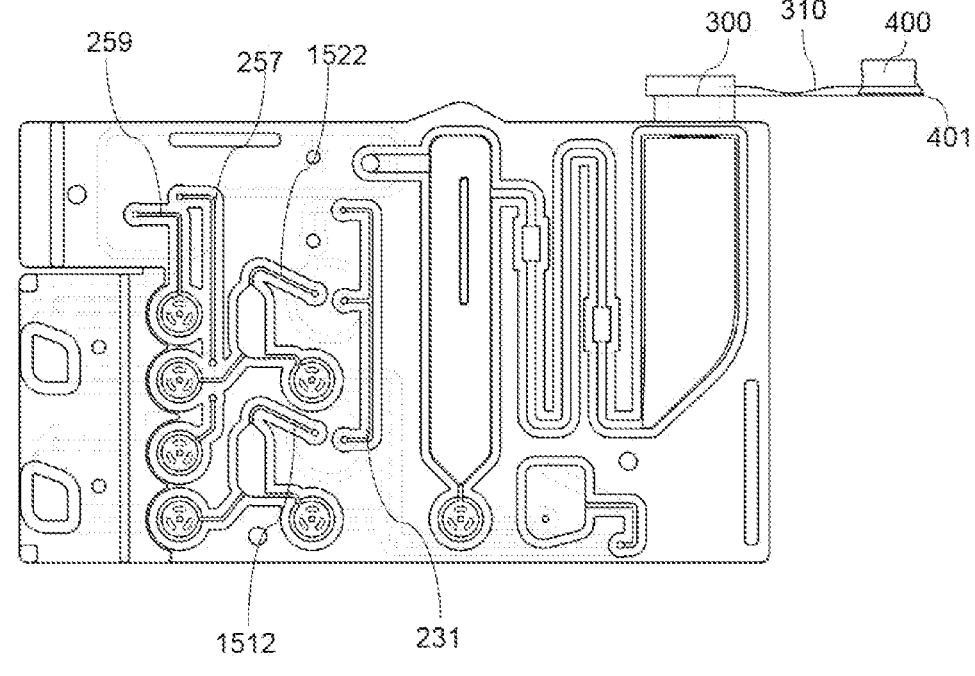
FIG. 7 is the front view structure schematic diagram of the cartridge body of the cartridge in Example 1 of the present invention.

Referring to FIG. 1, FIG. 1 is the structure schematic diagram of the cartridge of Example 1 of the present invention;

As shown in FIGS. 1 to 33 and FIGS. 36 to 44, the cartridge of a preferred embodiment of the present invention, as shown in FIGS. 1 to 4, it comprises cartridge body 100, first lyophilized bead 610, second lyophilized bead 620, first mixing bead 710, second mixing bead 720, filtration film 1600, first waterproof and breathable film 1510, second waterproof and breathable film 1520, third waterproof and breathable film 1530, first sealing film 1200, second sealing film 1400, third sealing film 1300, first rubber cushion, second rubber cushion 522, third rubber cushion 532, fourth rubber cushion 542, fifth rubber cushion 552, sixth rubber cushion 562 and seventh rubber cushion 572;

As shown in FIG. 5 to FIG. 7, lid 400, cassette sample addition nozzle 300, sample addition chamber 111, siphon part 121, sample lysis chamber 132, first valve chamber, and sample filtration chamber 141, second valve chamber 521, first sample mixing chamber 1511, third valve chamber 531, second sample mixing chamber 1521, fourth valve chamber 541, fifth valve chamber 551, sixth valve chamber 561, seventh valve chamber 571, first PCR chamber 1611 and second PCR chamber 1621 are provided on cartridge body 100;

Sample addition chamber 111, sample lysis chamber 132, first valve chamber, sample filtration chamber 141, second valve chamber 521, first sample mixing chamber 1511, third valve chamber 531, second sample mixing chamber 1521, fourth valve chamber 541, fifth valve chamber 551, sixth valve chamber 561, seventh valve chamber 571, first PCR chamber 1611 and second PCR chamber 1621 are all disposed on the first surface of cartridge body 100, and are all chambers with openings toward the first surface of cartridge body 100. Siphon part 121 is a slot with an opening toward the first surface of cartridge body 100, and the surface of cartridge body 100 facing away from the first surface of cartridge body 100 is the second surface.

Wherein, first PCR chamber 1611 and second PCR chamber 1621 are pass-through chambers;

Part of the structure of the first surface of cartridge body 100 is recessed downward as a whole, and the downwardly recessed part forms step portion 170, so that the first surface of cartridge body 100 presents a step shape as a whole; first PCR chamber 1611 and second PCR chamber 1621 are disposed on step portion 170.

Lid 400 is connected with cassette sample addition nozzle 300, and lid 400 can be covered on cassette sample addition nozzle 300, thus sealing cassette sample addition nozzle 300, and preventing extraneous objects from entering into sample addition chamber 111 through cassette sample addition nozzle 300, and maintaining the air pressure of each chamber in cartridge body 100. Lid 400 also serves to prevent liquid from flowing out of the cartridge, thus avoiding the problem of samples leaking out of the cartridge and causing viruses in the sample to infect the assayer or PCR amplification products to spread in the environment and cause testing accidents.

Cassette sample addition nozzle 300 communicates with sample addition chamber 111, sample addition chamber 111 is connected with one end of siphon part 121, sample lysis chamber 132 is connected with the other end of siphon part 121, and sample addition chamber 111 communicates with sample lysis chamber 132 through siphon part 121;

The first valve chamber is disposed at the bottom of sample lysis chamber 132, and communicates with sample lysis chamber 132;

The bottom of the first valve chamber is provided with a first flow channel hole and three first bulged parts 5111, a first opening is provided on the side wall of the first valve chamber, and the first opening communicates with the sample lysis chamber, The sample flowing out of sample lysis chamber 132 flows into the first valve chamber through the first opening, and then flows out through the first flow channel hole. Three first bulged parts 5111 are arranged around the first flow channel hole with equal gaps, and the sample can flow into the first flow channel hole through the gaps between three first bulged parts 5111, and the bottom of the first rubber cushion is in contact with each first bulged part 5111. When the first rubber cushion is compressed, the first rubber cushion is deformed and blocks the first flow channel hole, so that the sample cannot flow into other chambers through the first flow channel hole.

Cartridge body 100 is provided with first flow channel 251 between the first valve chamber and sample filtration chamber 141, and the first valve chamber communicates with sample filtration chamber 141 through first flow channel 251, i.e., first flow channel 251 and the first flow channel holes are communicated, the other end of first flow channel 251 communicates with sample filtration chamber 141, the filtration film is disposed in sample filtration chamber 141, and the filtration film is used to filter out macromolecular impurities; The sample lysed in sample lysis chamber 132 flows into the first valve chamber through the first opening, enters first flow channel 251 through the first flow channel hole, and then flows into sample filtration chamber 141; when the first rubber cushion is compressed, the first rubber cushion is deformed, the first flow channel hole is blocked and blocks the first flow channel hole, so that the sample cannot flow into first flow channel 251 through the first flow channel hole, and thus cannot reach sample filtration chamber 141.

The bottom of second valve chamber 521 is provided with a second flow channel hole and three second bulged parts, a second opening is provided on the side wall of second valve chamber 521, and the second opening communicates with the first sample mixing chamber, the sample flowing out of sample filtration chamber 141 flows out through the second flow channel hole, the three second bulged parts are arranged around the second flow channel hole with equal gaps, and the sample can flow into the second flow channel hole through the gaps between the three second bulged parts, and the bottom of second rubber cushion 522 is in contact with the second bulged parts;

When second rubber cushion 522 is compressed, second rubber cushion 522 is deformed and blocks the second flow channel hole, so that the sample cannot flow into other chambers through the second flow channel hole.

First mixing bead 710 and the first lyophilized bead 610 are located in first sample mixing chamber 1511, driven by an external power device (such as a magnetic device), first mixing bead 710 can move within first sample mixing chamber 1511. On the one hand, the movement of first mixing bead 710 can collide with first lyophilized bead 610 to smash first lyophilized bead 610 to accelerate the redissolution of first lyophilized bead 610. On the one hand, the movement of first mixing bead 710 directly and thoroughly mixes the redissolved first lyophilized bead 610 with the sample.

Cartridge body 100 is provided with second flow channel 252 communicated with both sample filtration chamber 141 and first sample mixing chamber 1511 therebetween, and second valve chamber 521 is provided on second flow channel 252, specifically: first sample mixing chamber 1511 communicates with the second opening of second valve chamber 521, the second flow channel hole of second valve chamber 521 communicates with sample filtration chamber 141 through second flow channel 252, and the sample filtered in sample filtration chamber 141 flows through second flow channel 252 through the second flow channel hole and enters first sample mixing chamber 1511; when second rubber cushion 522 is compressed, second rubber cushion 522 is deformed, and blocks the second flow channel hole, so that the sample cannot flow into first sample mixing chamber 1511 through the second flow channel hole.

The bottom of third valve chamber 531 is provided with a third flow channel hole and three third bulged parts, a third opening is provided on the side wall of third valve chamber 531, and the third opening communicates with the second sample mixing chamber, the sample flowing out of sample filtration chamber 141 flows into the next chamber through the third flow channel hole, the three third bulged parts are arranged around the third flow channel hole with equal gaps, and the sample can flow into the third flow channel hole through the gaps between the three third bulged parts, the bottom of third rubber cushion 532 is in contact with the third bulged parts;

When third rubber cushion 532 is compressed, third rubber cushion 532 is deformed and blocks the third flow channel hole, so that the sample cannot flow into other chambers through the third flow channel hole.

Second mixing bead 720 and second lyophilized bead 620 are located within second sample mixing chamber 1521, driven by the external magnetic device, second mixing bead 720 can move in second sample mixing chamber 1521, On the one hand, the movement of second mixing bead 720 can collide with second lyophilized bead 620 to smash second lyophilized bead 620 to accelerate the redissolution of second lyophilized bead 620; on the other hand, the movement of second mixing bead 720 directly and thoroughly mixes the redissolved second lyophilized bead 620 with the sample.

Cartridge body 100 is provided with third flow channel 252 communicated with both sample filtration chamber 141 and second sample mixing chamber 1511 therebetween, and third valve chamber 521 is provided on third flow channel 252, specifically: second sample mixing chamber 1521 communicates with the third opening of third valve chamber 531, the third flow channel hole of third valve chamber 531 communicates with sample filtration chamber 141 through third flow channel 253, the sample filtered in sample filtration chamber 141 flows through third flow channel 253 through the third flow channel hole and enters second sample mixing chamber 1521; when third rubber cushion 532 is compressed, third rubber cushion 532 is deformed and blocks third flow channel hole, so that the sample cannot flow into second sample mixing chamber 1521 through the third flow channel hole.

Wherein, second flow channel 252 and third flow channel 253 communicate with each other. Second flow channel 252 and third flow channel 253 can also be implemented as a flow channel with a first end communicating with sample filtration chamber 141 after bifurcation, with the second end of the flow channel communicating with first sample mixing chamber 1511 via a second valve chamber and the third end of the flow channel communicating with second sample mixing chamber 1521 via a third valve chamber, respectively.

The bottom of fourth valve chamber 541 is provided with a fourth flow channel hole and three fourth bulged parts, a fourth opening is provided on the side wall of fourth valve chamber 541, and the fourth opening communicates with the sample mixing chamber, the sample flowing out of first sample mixing chamber 1511 flows into the next chamber through the fourth flow channel hole, and the three fourth bulged parts are arranged around the fourth flow channel hole with equal gaps, and the sample can flow into the fourth channel hole through the gaps between the three fourth bulged parts, and the bottom of fourth rubber cushion 542 is in contact with the fourth bulged parts; when fourth rubber cushion 542 is compressed, fourth rubber cushion 542 is deformed and blocks the fourth flow channel hole, so that the sample cannot flow into other chambers through the fourth flow channel hole.

Cartridge body 100 is provided with fourth flow channel 254 between first sample mixing chamber 1511 and first PCR chamber 1611, first sample mixing chamber 1511 communicates with one end of fourth flow channel 254, first PCR chamber 1611 communicates with the other end of fourth flow channel 254, and the sample in first sample mixing chamber 1511 flows into the first PCR chamber through fourth flow channel 254. Fourth valve chamber 541 is disposed on fourth flow channel 254, and the fourth flow channel hole communicates with fourth flow channel 254; the sample mixed in first sample mixing chamber 1511 flows into first PCR chamber 1611 through fourth flow channel 254;

When fourth rubber cushion 542 is compressed, fourth rubber cushion 542 is deformed and blocks the fourth flow channel hole, so that the sample from first sample mixing chamber 1511 cannot flow into the fourth flow channel hole inside first PCR chamber 1611.

The bottom of fifth valve chamber 551 is provided with a fifth flow channel hole and three fifth bulged parts, and a fifth opening is provided on the side wall of second valve chamber 522, and the fifth opening communicates with the second sample mixing chamber, the sample flowing out of second sample mixing chamber 1521 flows into the next chamber through the fifth flow channel hole, and the three fifth bulged parts are arranged around the fifth flow channel hole with equal gaps, and the sample can flow into the fifth flow channel hole through the gaps between the three bulged parts, the bottom of the fifth rubber cushion is in contact with the fifth bulged parts; when the fifth rubber cushion is compressed, the fifth rubber cushion is deformed and blocks the fifth flow channel hole, so that the sample cannot flow into other chambers through the fifth flow channel hole.

Cartridge body 100 is provided with fifth flow channel 255 between second sample mixing chamber 1521 and second PCR chamber 1621, second sample mixing chamber 1521 communicates with one end of fifth flow channel 255, and second PCR chamber 1621 communicates with the other end of fifth flow channel 255, and the sample in second sample mixing chamber 1521 flows into the second PCR chamber through fifth flow channel 255. Fifth valve chamber 551 is disposed on fifth flow channel 255, and the fifth flow channel hole communicates with fifth flow channel 255; the sample mixed in second sample mixing chamber 1521 flows into second PCR chamber 1621 through fifth flow channel 255;

When the fifth rubber cushion is compressed, the fifth rubber cushion is deformed and blocks the fifth flow channel hole, so that the sample coming out from second sample mixing chamber 1521 cannot flow into second PCR chamber 1621 through the fifth flow channel hole.

First air slot 911, first air hole 201, second air hole 202 and first air passage 211 are provided on cartridge body 100; first air hole 201 is disposed in first air slot 911, and second air hole 202 is disposed on first air slot 911 and first air passage 211, second air hole 202 communicates with first air slot 911 and first air passage 211, first air passage 211 communicates with the upper part of sample lysis chamber 132, and first air hole 201 is used to connect external inflation device or air pressure regulating device;

First waterproof and breathable film 1510 is covered on first air slot 911 to prevent the sample from leaking out of first air slot 911, and can also discharge the air in the sample. First waterproof and breathable film 1510 is welded on first air slot 911 by laser welding. In one embodiment, first waterproof and breathable film 1510 is welded on the slot wall of first air slot 911, and can also be welded on the surface of the top outer edge of first air slot 911. In another preferred embodiment, first waterproof and breathable film 1510 is laser welded around first air hole 201, second air hole 202, ninth air hole 209 and tenth air hole 2010; the first waterproof and breathable film is welded near the outer circumference of first air hole 201 to prevent the sample from overflowing from first air hole 201 or blocking first air hole 201, which makes first air hole 201 unable to perform the air inlet or outlet operation; welding to second air hole 202 is to avoid the sample overflowing from the sample lysis chamber into second air hole 202 or even into first air hole 201, causing the problem of virus leakage from the sample, leading to a medical incident of human infection; welding on ninth air hole 209 and tenth air hole 2010 in order to make the liquid sample enters ninth air hole 209 or tenth air hole 2010, it can be quickly blocked by first waterproof and breathable film 1510, so that the sample stops continuing to enter the first PCR chamber or the second PCR chamber, and first waterproof and breathable film 1510 is welded around ninth air hole 209 and tenth air hole 2010, which can effectively increase the contact between first waterproof and breathable film 1510 and ninth air hole 209 and tenth air hole 2010. After the liquid sample comes out, it can be immediately in contact with first waterproof and breathable film 1510, preventing the sample from entering first air slot 911, which may easily cause contamination events. Alternatively, one waterproof and breathable film is welded around ninth air hole 209, i.e., the waterproof and breathable film is directly sealed on ninth air hole 209, and another waterproof and breathable film is welded around tenth air hole 2010, and the waterproof and breathable film is directly sealed on tenth air hole 2010, which also can achieve the above function.

In addition, ninth air hole 209 and tenth air hole 2010 can be disposed together in an independent air slot, and this air slot is covered and blocked by a waterproof and breathable film, or ninth air hole 209 is independently arranged in an air slot. In the groove, tenth air hole 2010 is independently disposed in an air slot, and is covered and blocked by corresponding waterproof and breathable films respectively. First air hole 201 and second air hole 202 are disposed in the same air slot to achieve communication. Meanwhile, to achieve communication between first air hole 201 and second air hole 202, a sealing film needs to be set on the first air slot for sealing, so that when air is withdrawn from or pumped into first air hole 201 by the air pump, it can act on the sample lysis chamber 132 through second air hole 202.

In this embodiment, the outer side of first waterproof and breathable film 1510 is provided with a second sealing film to seal the first air slot. When first air hole 201 is inflated with air by the air inflation device outside first air hole 201, the air enters first air slot 911 from first air hole 201, and then enters first air passage 211 from first air slot 911 through second air hole 202, enters sample lysis chamber 132 through first air passage 211. When sample lysis chamber 132 is in a closed state, the air entering sample lysis chamber 132 from first air hole 201 increases the air pressure in the sample lysis chamber. The sample in sample lysis chamber 132 can be pressed into sample filtration chamber 141 from sample lysis chamber 132 through the first valve chamber;

When air is withdrawn from first air hole 201 with the external air pressure regulating device, the air in sample lysis chamber 132 enters first air slot 911 from first air passage 211 through second air hole 202, then drawn out from air slot 911. Since the air in sample lysis chamber 132 is drawn out, the air pressure in the sample lysis chamber is reduced, so that the sample in siphon part 121 or sample addition chamber 111 is drawn into sample lysis chamber 132.

Cartridge body 100 is provided with second air slot 921, third air slot 931, third air hole 203, fourth air hole 204, fifth air hole 205, sixth air hole 206, seventh air hole 207, eighth air hole 208, second air passage 221 and third air passage 231.

One end of third air hole 203 communicates with the air pressure regulating device (such as an air pump) to be used for blowing air or extracting air, and the other end of third air hole 203 communicates with the third air passage 231 through second air passage 221, the one end of third air hole 203 communicating with the air pressure regulating device and third air passage 231 are located on the same surface of cartridge body 100, and second air passage 221 and third air passage 231 are located on the opposite surfaces of cartridge body 100; The reason why second air passage 221 is provided, and second air passage 221 is disposed on the surface opposite to the end where third air passage 231 and third air hole 203 communicate with the air pressure regulating device, are as follows:

1) when the air pump is directly connected to the third air passage, it cannot be effectively sealed, and the airtightness requirement of the air pump cannot be guaranteed;

2) The periphery of the third air passage needs to be welded to achieve sealing, and thus has a laser welding line, which can produce a bulged feature with a height of 0.001-0.1 mm on cartridge body 100, while the flat surface where cartridge body 100 is connected to the air pump needs good flatness to ensure the airtightness of the contact. Therefore, if the air pump is connected to the third air passage, the air pump cannot be sealed, but the cartridge can be sealed with the air pump through the second air passage.

Second air passage 221 and third air passage 231 communicate through fourth air hole 204, because the second air passage and the third air passage are not located on the same side of cartridge body 100, therefore, second air passage 221 and third air passage 231 are communicated through fourth air hole 204, so that the air can flow from fourth air hole 204 between second air passage 221 and third air passage 231.

In the present embodiment, the one end that the third air hole communicates with the air pressure regulating device and the third air passage 231 are all located on the first surface of cartridge body 100, and the second air passage is located on the second surface of cartridge body 100. Therefore, the air pressure adjusting device can be communicated with one end of the third air hole on the first surface of cartridge body 100 to avoid the welding line of the second air passage and the welding line of the third air passage, thus ensuring the airtightness of the connection between the air pressure regulator and the cartridge.

Fifth air hole 205 is disposed on third air passage 231 and second air slot 921, the upper part of first sample mixing chamber 1511 extends a first air passage, and sixth air hole 206 is disposed on second air slot 921 and the first air passage;

Second waterproof and breathable film 1520 is disposed on second air slot 921; second waterproof and breathable film 1520 allows second air slot 921 to be waterproof, breathable, while allowing air discharge from the sample. In one embodiment, second waterproof and breathable film 1520 is welded on second air slot 921. In another preferred embodiment, second waterproof and breathable film 1520 is welded around fifth air hole 205 and sixth air hole 206 on second air slot 921. In this way, when the sample enters sixth air hole 206, it is immediately blocked by second waterproof and breathable film 1520, thereby avoiding the risk of sample leakage. Optionally, a separate waterproof and breathable film is directly welded on sixth air hole 206, so that it can have better waterproofness, so as to prevent the risk of sample leakage caused by liquid flowing out of the waterproof and breathable film. Certainly, it is better to weld the second waterproof and breathable film around fifth air hole 205 and sixth air hole 206 respectively, which can further avoid sample leakage.

Further, a second sealing film is provided on the outside of second waterproof and breathable film 1520 to seal second air slot 921, so that the air communication between fifth air hole 205 and sixth air hole 206 can be realized. First sample mixing chamber 1511 communicates with third air hole 203 through the first air passage, sixth air hole 206, the second air slot, fifth air hole 205, third air passage 231, fourth air hole 204, and the second air passage in sequence.

Seventh air hole 207 is disposed on third air passage 231 and third air slot 931, the upper part of second sample mixing chamber 1521 extends with a second air passage, and eighth air hole 208 is disposed on third air slot 931 and the second air passage. Since the second air passage and the third air slot are located on different surfaces of cartridge body 100, it is avoided that when third air hole 203 is connected to the external air pump, it will not directly act on the external sealing film, resulting in the sealing film being destroyed under pressure thus leading to the problem of sample leakage;

Third waterproof and breathable film 1530 is disposed on third air slot 931; third waterproof and breathable film 1530 allows third air slot 931 to be waterproof, breathable, while allowing air discharge from the sample. In one embodiment, third waterproof and breathable film 1530 is welded on third air slot 931. In another preferred embodiment, third waterproof and breathable film 1530 is welded around seventh air hole 207 and eighth air hole 208 on third air slot 921. Therefore, when the sample enters the eighth air hole, it is immediately blocked by the third waterproof and breathable film 1520, thereby avoiding the risk of sample leakage.

Optionally, the waterproof and breathable film is directly welded on the eighth air hole, so that it can have better waterproofness, so as to prevent the risk of sample leakage caused by liquid overflowing outside the waterproof and breathable film. Certainly, it is better to weld third waterproof and breathable film 1530 around seventh air hole 207 and eighth air hole 208 respectively, which can further avoid sample leakage.

Further, a second sealing film is provided on the outside of third waterproof and breathable film 1530 to seal third air slot 931, so that the air communication between seventh air hole 207 and eighth air hole 208 can be realized. The second sample mixing chamber 1511 communicates with third air hole 203 through the second air passage, eighth air hole 208, the third air slot, seventh air hole 207, third air passage 231, fourth air hole 204, and the second air passage in sequence.

The bottom of sixth valve chamber 561 is provided with the sixth flow channel hole and three sixth bulged parts, and the side wall of sixth valve chamber 561 is provided with the sixth opening, and the three sixth bulged parts are disposed around the sixth flow channel hole with equal gaps, the sample can flow into the sixth flow channel hole through the gap between the three sixth bulged parts, and the bottom of the sixth rubber cushion is in contact with the sixth bulged part; When the sixth rubber cushion is compressed, the sixth rubber cushion is deformed and blocks the third flow channel hole, so that the sample cannot flow into other chambers through the sixth flow channel hole.

Cartridge body 100 is provided with sixth flow channel 256, ninth air hole 209 and the seventh flow channel, one end of sixth flow channel 256 communicates with first PCR chamber 1611, and the other end of sixth flow channel 256 communicates with first PCR chamber 1611. The sixth flow channel hole communicates with, one end of the seventh flow channel communicates with the sixth opening of the sixth valve chamber 561, and the other end of the seventh flow channel communicates with first air slot 911 through ninth air hole 209.

The bottom of seventh valve chamber 571 is provided with the seventh flow channel hole and three seventh bulged parts, and the side wall of seventh valve chamber 571 is provided with the seventh opening, and the three seventh bulged parts are disposed around the seventh flow channel hole with equal gaps, the sample can flow into the seventh flow channel hole from the gap between the three seventh bulged parts, and the bottom of seventh rubber cushion 572 is in contact with the seventh bulged part; when seventh rubber cushion 572 is compressed, seventh rubber cushion 572 is deformed and blocks the third flow channel hole, so that the sample cannot flow into other chambers through the seventh flow channel hole.

Cartridge body 100 is provided with eighth flow channel 258, tenth air hole 2010 and ninth flow channel 259, one end of eighth flow channel 258 communicates with second PCR chamber 1621, and the other end of eighth flow channel 258 communicates with the seventh flow channel hole, one end of ninth flow channel 259 communicates with the seventh opening of seventh valve chamber 571, and the other end of ninth flow channel 259 communicates with first air slot 911 through tenth air hole 2010.

Wherein, siphon part 121, first air passage 211, third air passage 231, seventh flow channel 257 and the ninth flow channel 259 are all slots disposed on the first face of cartridge body 100;

First flow channel 251, sixth flow channel 256, eighth flow channel 258, first air slot 911, second air slot 921, third air slot 931 and second air passage 221 are all slots disposed on the second side of cartridge body 100.

The parts of second flow channel 252, third flow channel 253, fourth flow channel 254, fifth flow channel 255 are slots being disposed on the first face of cartridge body 100, and the other parts are slots being disposed on the second surface of cartridge body 100; for the same flow channel, the slots provided on the first surface and the slots provided on the second surface are communicated through corresponding valve chambers, for example, for fourth flow channel 254, fourth valve chamber 541 communicates between the slots provided on the first surface and the slots provided on the second surface.

Figure 3:
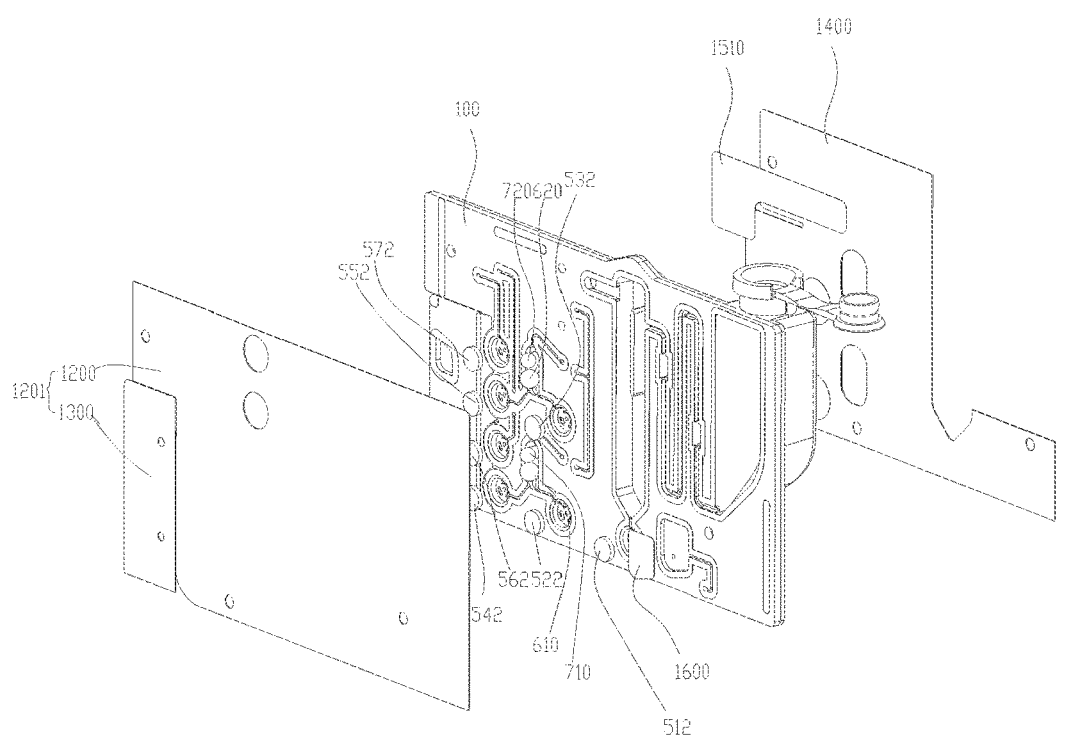
FIG. 3 is the front exploded view of the cartridge in Example 1 of the present invention.
Figure 4:
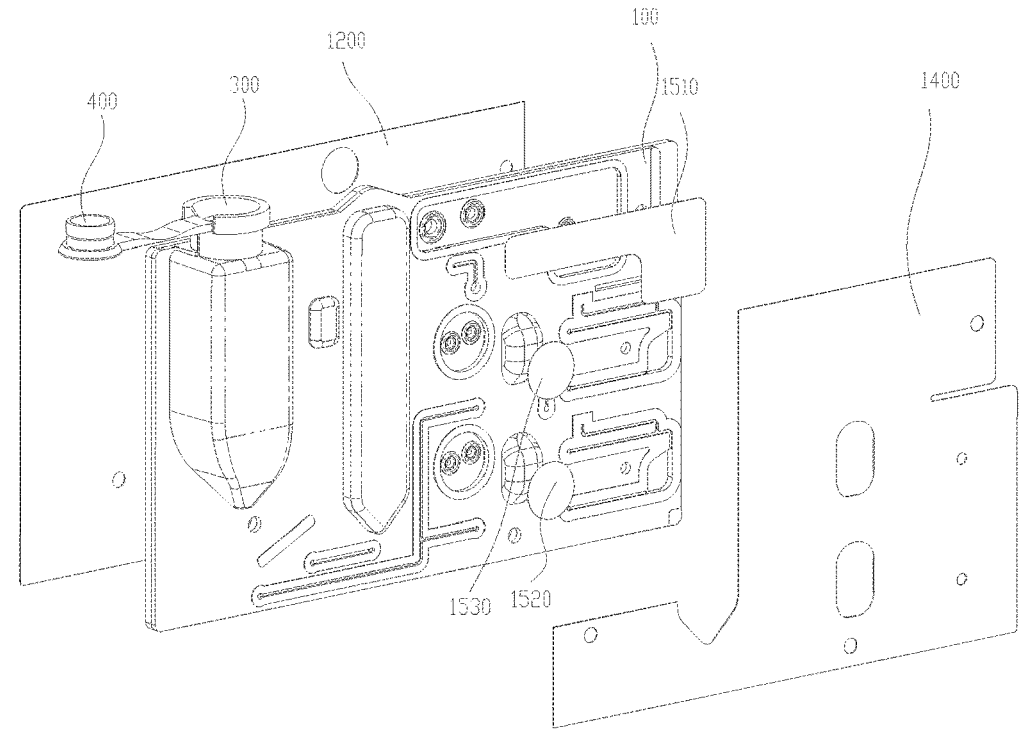
FIG. 4 is the back exploded view of the cartridge in Example 1 of the present invention.
Figure 14:
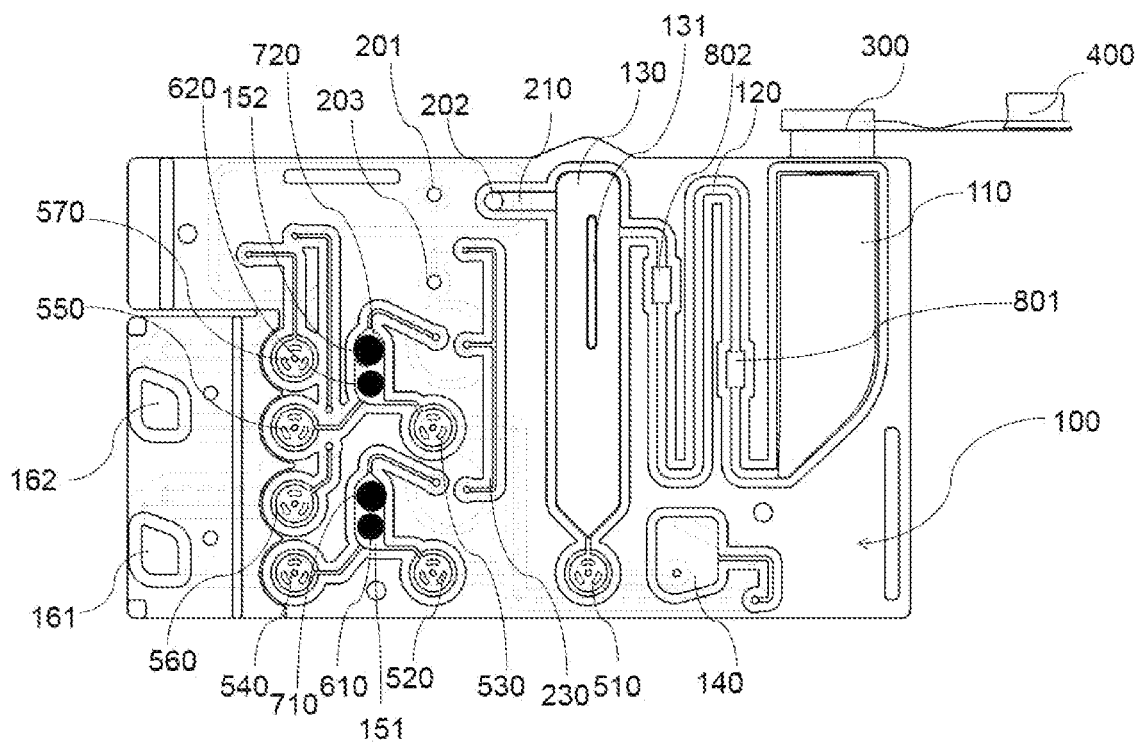
FIG. 14 is the structure schematic diagram of the front of the cartridge in Example 1 of the present invention.
Figure 15:
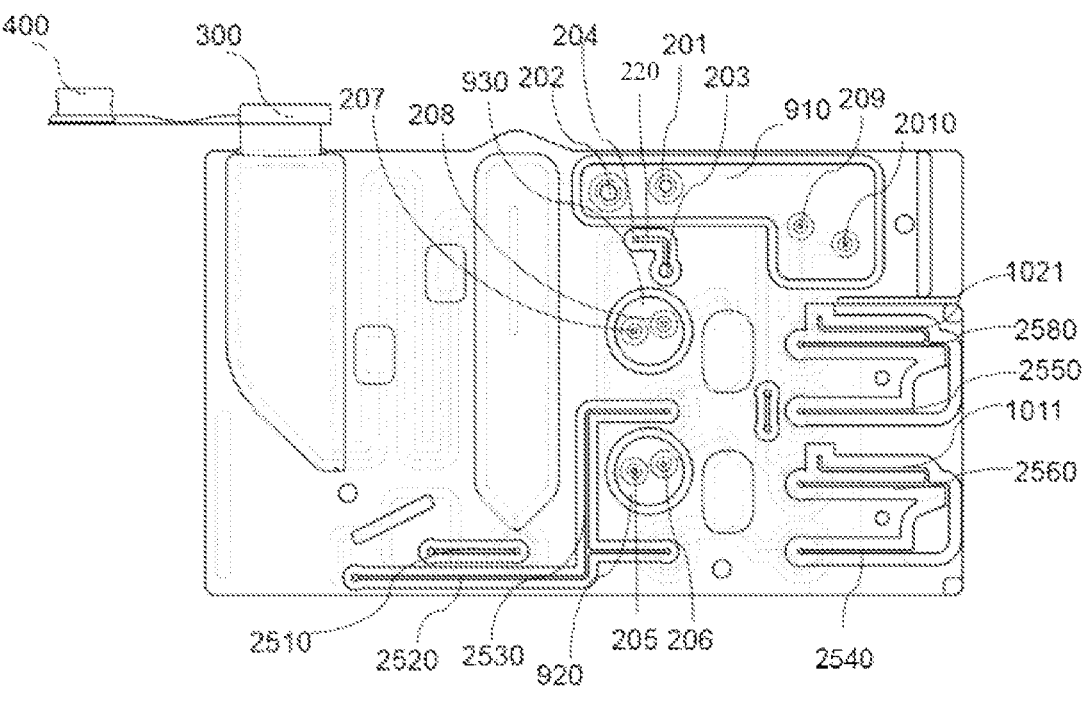
FIG. 15 is the structure schematic diagram of the back of the cartridge in Example 1 of the present invention.

As shown in FIG. 3, FIG. 14 and FIG. 15, wherein, first sealing film 1200 covers the first surface of cartridge body 100, specifically, first sealing film 1200 is welded on the first surface of cartridge body 100 On the surface, for sealing sample addition chamber 111, sample lysis chamber 132, the first valve chamber, sample filtration chamber 141, second valve chamber 521, first sample mixing chamber 1511, third valve chamber 531, and second sample mixing chamber 1521, fourth valve chamber 541, fifth valve chamber 551, sixth valve chamber 561 and seventh valve chamber 571, as well as sealing the slots such as siphon part 121, first air passage 211, third air passage 231, seventh flow channel, ninth flow channel etc., thereby avoiding the problem of sample leakage from the above-mentioned cavities or slots, resulting in the virus in the sample infecting the testing operators or spreading in the environment, causing testing accidents.

Sample addition chamber 111 and first sealing film 1200 together form a closed space, i.e. sample addition compartment 110; sample lysis chamber 132 and first sealing film 1200 together form a closed space, i.e. sample lysis compartment 130; sample filtration chamber 141 and first sealing film 1200 together form a closed space, i.e., sample filtration compartment 140; first sample mixing chamber 1511 and first sealing film 1200 together form a closed space, i.e., first sample mixing compartment 151; second sample mixing chamber 1521 and first sealing film 1200 together form a closed space, i.e., second sample mixing compartment 152.

Figure 10:
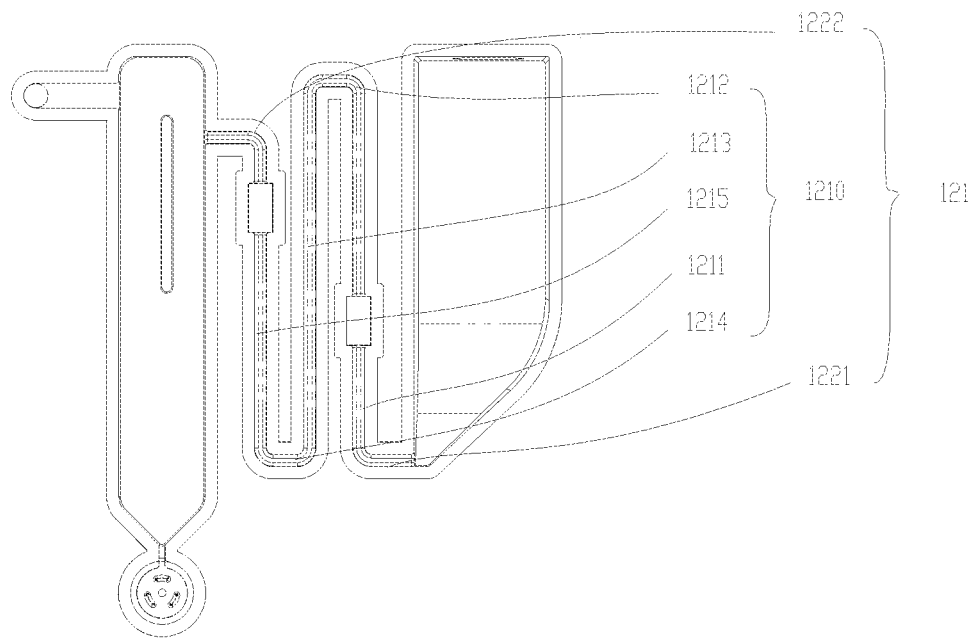
FIG. 10 is the structure schematic diagram of siphon part.

As shown in FIG. 10, siphon part 121 and first sealing film 1200 together form a closed space, i.e., siphon tube 120.

First air passage 211 and first sealing film 1200 form first air channel 210; third air passage 231 and first sealing film 1200 form third air channel 230; the seventh flow channel and first sealing film 1200 form seventh channel 2570; ninth flow channel 259 and first sealing film 1200 form ninth channel 2590; the first air passage and first sealing film 1200 form first air channel 1512; the second air channel and first sealing film 1200 forms second air channel 1522.

Compared with other parts of cartridge body 100, the upper surface of step portion 170 is overall concave. In this embodiment, a third sealing film 1300 is separately disposed to cover the surface of step portion 170, specifically: third sealing film 1300 is welded on step portion 170, and third sealing film 1300 is used to seal chambers such as first PCR chamber 1611 and second PCR chamber 1621. The thickness of third sealing film 1300 is 0.1 mm; the arrangement of the step portion 170 facilitates the processing and manufacture of the cartridge, and also facilitates the providing of the first PCR chamber and the second PCR chamber with smaller thicknesses.

First PCR chamber 1611 is sealed by second sealing film 1400 and third sealing film 1300, and together form a closed space, i.e., first PCR chamber 161; second PCR chamber 1621 is sealed by second sealing film 1400 and first PCR chamber 161, and together form a closed space, i.e., second PCR compartment 162;

Second sealing film 1400 is covered on the second surface of cartridge body 100, for sealing the slots such as first flow channel 251, second flow channel 252, third flow channel 253, fourth flow channel 254, fifth flow channel 255, sixth channel 256, eighth channel 258, and second air passage 221, etc.

First flow channel 251 and second sealing film 1400 form first channel 2510; second flow channel 252 and second sealing film 1400 form second channel 2520; third flow channel 253 and second sealing film 1400 form third channel 2530, fourth flow channel 254 and second sealing film 1400 form fourth channel 2540, fifth flow channel 255 and second sealing film 1400 form fifth channel 2550, and sixth flow channel 256 and second sealing film 1400 form sixth channel 2560, eighth flow channel 258 and the sealing film 1400 form eighth channel 2580, second air passage 221 and second sealing film 1400 form second air channel 220;

First waterproof and breathable film 1510 is disposed in first air slot 911, and first air compartment 910 is formed by sealing the second sealing film disposed on the outside; second waterproof and breathable film 1520 is disposed in second air slot 921, and second air compartment 920 is formed by the second sealing film disposed on the outer side; third waterproof and breathable film 1530 is disposed in third air slot 931, and third air compartment 930 is formed by the second sealing film disposed on the outside, second sealing film 1400 covers on first waterproof and breathable film 1510, second waterproof and breathable film 1520 and third waterproof and breathable film 1530, and is used for sealing first air compartment 910, second air compartment 920 and third air compartment 930, to prevent the samples in first air compartment 910, second air compartment 920 and third air compartment 930 from diffusing through the corresponding first waterproof and breathable film 1510, second waterproof and breathable film 1520 and third waterproof and breathable film 1530 into the environment, infecting the testing operators and causing testing accidents; in addition, when the air circulates in first air compartment 910, second air compartment 920 or third air compartment 930, the second sealing film can realize that the outer sides of first air compartment 910, second air compartment 920 and third air compartment 930 are not connected to the atmosphere, thus realizing adjusting the air pressure difference with other compartments.

Wherein, the material of first waterproof and breathable film 1510, second waterproof and breathable film 1520 and third waterproof and breathable film 1530 can be waterproof and breathable materials: nylon film, PTFE, polyethersulfone/poly or polyvinylidene fluoride etc.

First air compartment 910 and the first air channel are disposed on the opposite surfaces, and are connected through second air hole 202, which is to avoid that there would be a greater risk of sample leakage when the air pump is directly connected to the first air channel during air withdrawal or pumping in, especially when the sample enters the air pump through the first air channel during air withdrawal; by the structure of the cartridge in this embodiment, when the air pump is working, for example during air withdrawal, even if the sample enters the first air channel, would be already blocked by the first waterproof and breathable film when entering first air compartment 910, so that the sample cannot enter the air pump through the first waterproof and breathable film. Therefore, the structure of the cartridge of the present embodiment does not have the risk of sample leakage as described above.

The thickness of first sealing film 1200 and the thickness of second sealing film 1400 are 0.1 mm.

In some embodiments, first sealing film 1200 and third sealing film 1300 can be an integral main sealing film 1201, and the thicknesses of first sealing film 1200, second sealing film 1400 and third sealing film 1300 are in the range of 0.1 mm-0.5 mm;

The materials of first sealing film 1200, second sealing film 1400 and third sealing film 1300 may be polypropylene plastic sealing film or polyethylene plastic sealing film;

In the present embodiment, it is preferably polyethylene plastic sealing film (i.e., transparent PP film), and the selection is to match with cartridge body. Since the cartridge body in this embodiment is made of black PP material, if the laser welding process is to be used for sealing, the sealing film on the surface of this layer must also be made of the same PP material and transparent in color, so that the best laser welding effect can be achieved. Therefore, a transparent polyethylene plastic sealing film is used.

When the cartridge body is made by other materials, and when the cartridge body is sealed by a non-laser welding process, other forms of sealing films can also be used. In the present embodiment, the cartridge body is sealed with the sealing films by a laser welding process; other sealing processes can be adopted, such as ultrasonic welding, hot pressing, etc.

Figure 11:
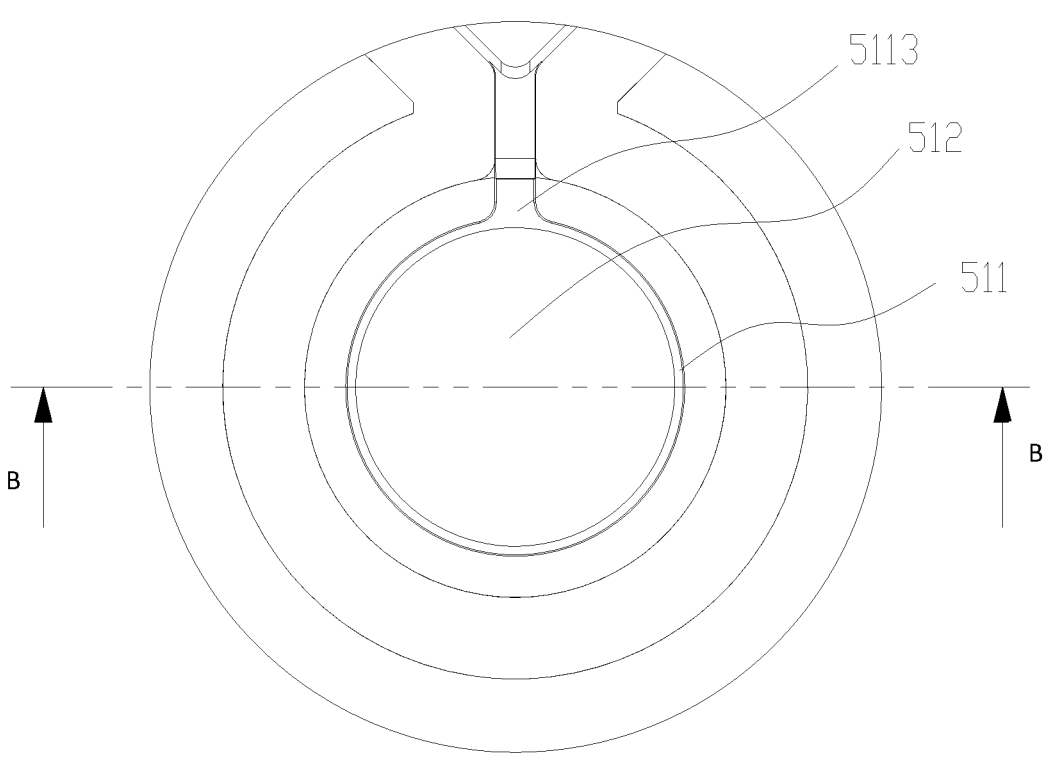
FIG. 11 is the front view schematic diagram of the first ejector valve.
Figure 12:
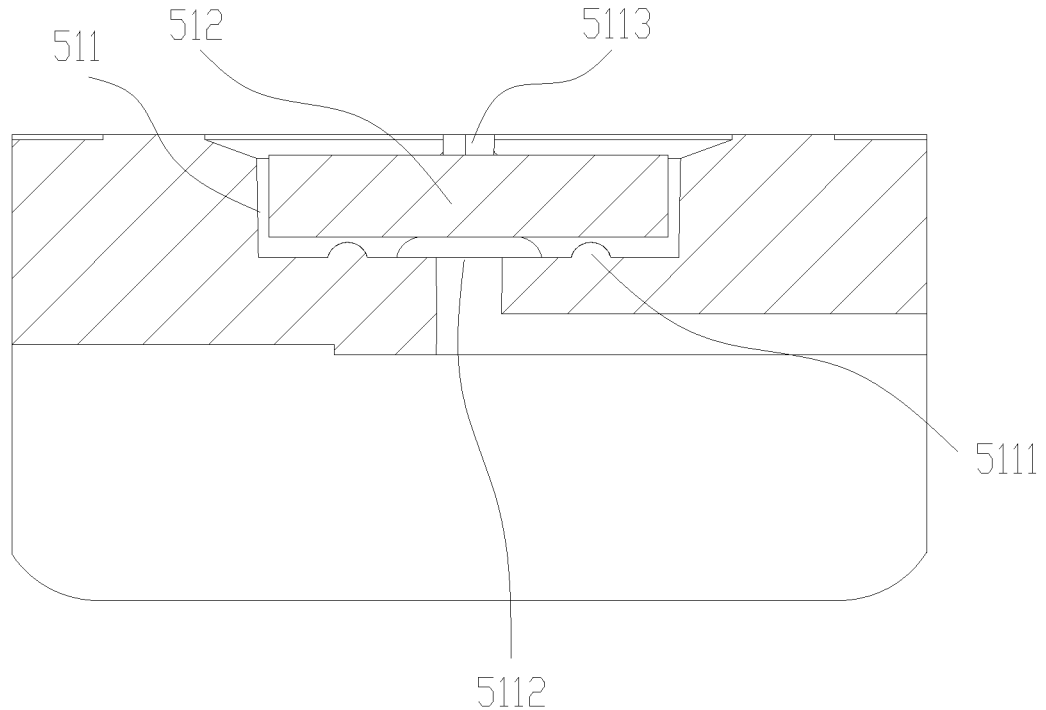
FIG. 12 is the sectional view of the first ejector valve in unoperated state, i.e. B-B in FIG. 11.
Figure 13:
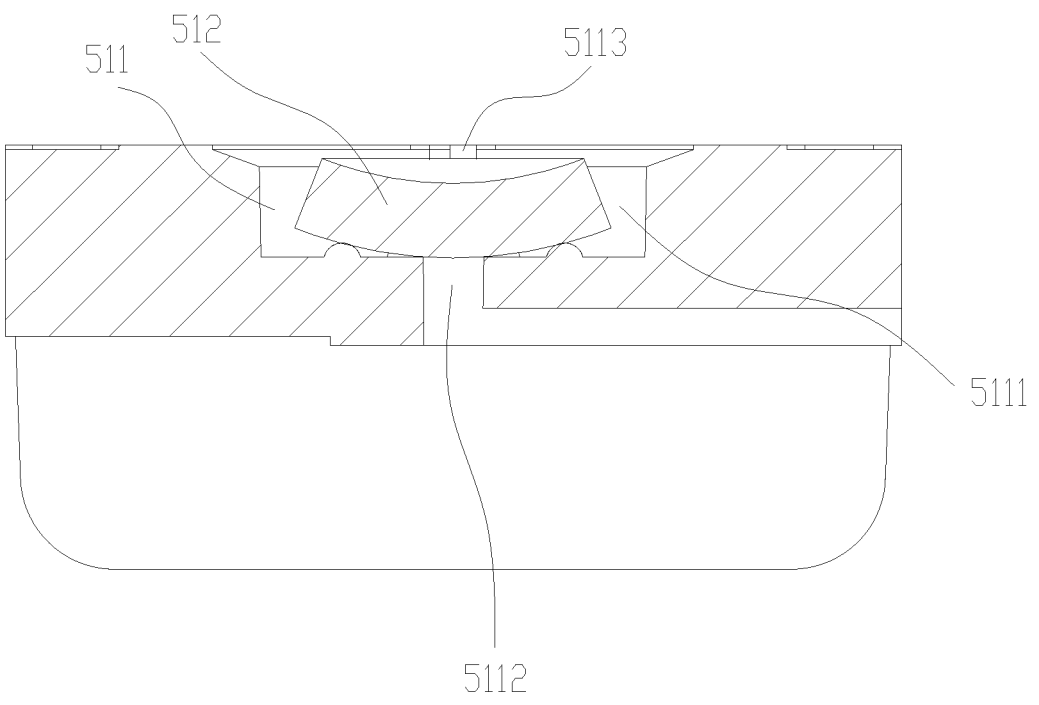
FIG. 13 is the sectional view of the first ejector valve in operated state, i.e. B-B in FIG. 11.

As shown in FIGS. 11-13, the first valve chamber and the first rubber cushion form first ejector valve 510, second valve chamber 521 and second rubber cushion 522 form second ejector valve 520, and third valve chamber 531 and third rubber cushion 532 form third ejector valve 530, fourth valve chamber 541 and fourth rubber cushion 542 form fourth ejector valve 540, fifth valve chamber 551 and the fifth rubber cushion form fifth ejector valve 550, the sixth valve chamber 561 and the sixth rubber cushion form sixth ejector valve 560, and seventh valve chamber 571 and seventh rubber cushion 572 form seventh ejector valve 570.

Figure 8:
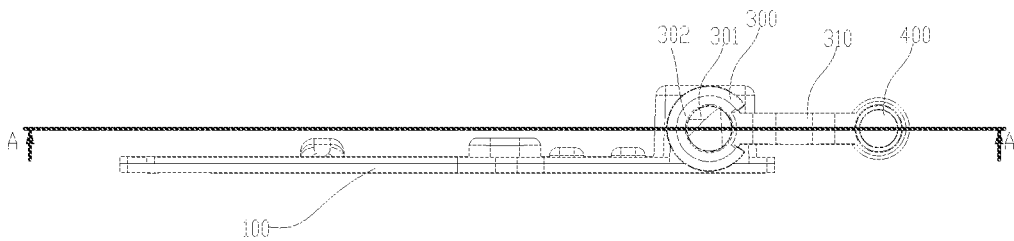
FIG. 8 is the top view schematic diagram of the cartridge body of the cartridge in Example 1 of the present invention.
Figure 9:
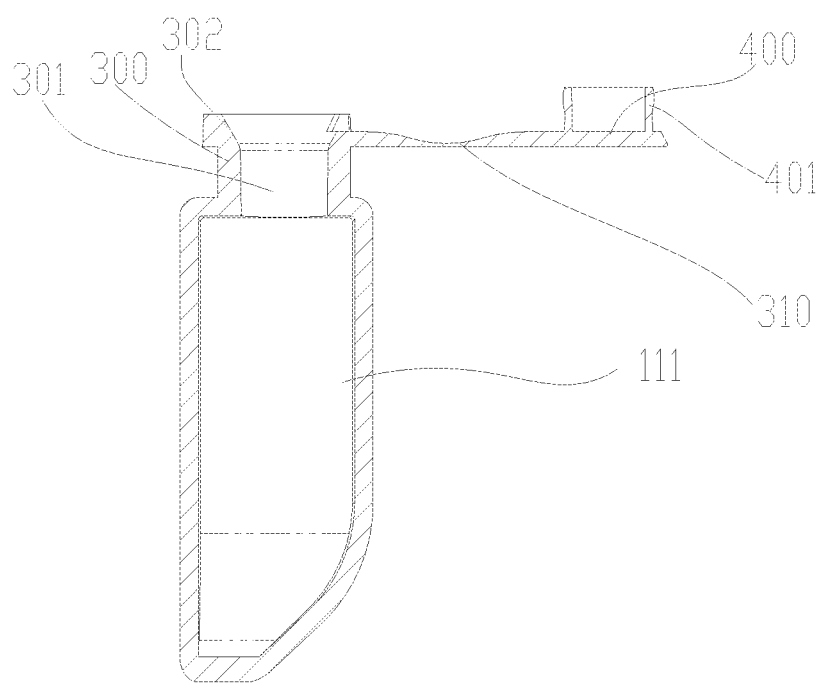
FIG. 9 is the sectional view of A-A in FIG. 8.

As shown in FIGS. 8 and 9, in the cartridge of the present embodiment, through-hole 301 on cassette sample addition nozzle 300 is provided, and through-hole 301 communicates with sample addition chamber 111, and lid 400 closes on cassette sample addition nozzle 300, for blocking through-hole 301 on cassette sample addition nozzle 300, so that cassette sample addition nozzle 300 can be sealed. As a result, foreign objects can be prevented from entering sample addition chamber 111 through cassette sample addition nozzle 300, the air pressure of each chamber in cartridge body 100 can be maintained, and liquid can be prevented from flowing out of the cartridge. The prevention of liquid outflow prevents the sample from leaking out of the cartridge, potentially infecting the testing personnel with the virus in the sample or causing the amplification product to spread in the environment, resulting in testing accidents.

Step 401 is provided on lid 400, and step 401 and through-hole 301 are interference fit, and when lid 400 covers cassette sample addition nozzle 300, through the relationship between through-hole 301 of step 401 and cassette sample addition nozzle 300, lid 400 realizes sealing cassette sample addition nozzle 300; when the testing operator presses lid 400 forcibly to cover lid 400 on cassette sample addition nozzle 300, it cannot be opened again, thereby avoiding the sample comes out from cassette sample addition nozzle 300, which causes the virus in the sample to infect the testing operators or spread into the environment, resulting in the problem of a testing accident.

Specifically: cassette sample addition nozzle 300 is provided with elastic part 310, the end of elastic part 310 is connected to lid 400, when not in use, lid 400 can stay on cartridge body 100 via the connection with elastic part 310, to avoid problems such as loss of lid 400 and placing lid 400 in other places after use, which may cause virus infection or inaccurate test results due to contamination of lid 400.

Wherein, lid 400, elastic part 310 and cassette sample addition nozzle 300 are integral to avoid over-processing of cartridge body 100 to affect the performance of cartridge body 100, and also to facilitate processing and manufacturing and reduce processing steps to achieve connection between lid 400, elastic part 310 and cassette sample addition nozzle 300.

In some embodiments, capping of the lid on the cassette sample addition nozzle 300 is achieved through a buckle; specifically: the lid is provided with a first protrusion, through-hole 301 is provided with a first groove. When the lid is closed in cassette sample addition nozzle 300, the first protrusion and the first groove cooperate with each other, so that the lid and cassette sample addition nozzle 300 can be closed by buckle connection; Alternatively, the lid is provided with a second groove and the through-hole 301 is provided with a second protrusion, and when the lid is closed in cassette sample addition nozzle 300, the second protrusion and the second groove cooperate with each other, so that the lid and cassette sample addition nozzle 300 are closed by buckle connection.

In some embodiments, lid 400, elastic part 310 and cassette sample addition nozzle 300 can also be connected by welding or nested connection, wherein lid 400 and cassette sample addition nozzle 300 can be tightly capped by means of a buckle; when elastic part 310 and lid 400 are rotatably connected, or when the elastic part 310 and the cartridge spacer 300 are pivotally connected, the lid 400 and cassette sample addition nozzle 300 can be tightly capped by means of a spin. When the elastic part 310 and lid 400 are rotatable or the elastic part 310 and cassette sample addition nozzle 300 are rotatable, lid 400 and cassette sample addition nozzle 300 can be tightly closed by means of screwing, i.e., when the elastic part and lid 400 or cassette sample addition nozzle 300 can be relatively rotatable, the lid and cassette sample addition nozzle 300 can be tightly closed by means of screwing, and the way of screwing can be provided with external threads on the outer circumference of the lid, and cassette sample addition nozzle 300 can be tightly closed by means of screwing. Cassette sample addition nozzle 300 is provided with an external thread on the outer circumference of the lid, and an internal thread matching the external thread is provided on through-hole 301 of cassette sample addition nozzle 300, and the lid and cassette sample addition nozzle 300 are screwed together by the internal thread and the external thread.

Elastic part 310 is rotatably connected to lid 400, specifically: an inlay slot is provided in the axial direction of lid 400, a kit is provided on elastic part 310, the kit is placed in the inlay slot, and the kit is a gap fit with the inlay slot, thereby achieving a rotatable connection between elastic part 310 and lid 400, or a first slot body is provided on elastic part 310, and a first convex ring is provided on the periphery of lid 400, and the first convex ring is set into the first slot body, and the first convex ring and the first slot body are gap-fitted, so as to achieve the rotatable connection between elastic part 310 and lid 400; the way to achieve the rotatable connection between elastic part 310 and lid 400 is not limited to the above-mentioned way, but can be set according to the actual situation, and can achieve the rotatable connection between elastic part 310 and lid 400. All the structure of the rotatable connection between the elastic part 310 and lid 400 is possible.

Elastic part 310 is rotatably connected with cassette sample addition nozzle 300, specifically: the second slot body is disposed on the outer periphery of cassette sample addition nozzle 300, elastic part 310 is provided with the corresponding second convex ring, the second slot body is connected with the second convex ring, and the second slot body and the second convex ring are in clearance fit, so that elastic part 310 and cassette sample addition nozzle 300 are rotatably connected; alternatively, elastic part 310 is provided with a third slot body, a corresponding third convex ring is disposed on the outer circumference of cassette sample addition nozzle 300, the third convex ring is connected with the third slot body, and the third slot body and the third convex ring are gap-fitted, so as to realize rotatable connection between elastic part 310 and cassette sample addition nozzle 300; The realization of the rotatable connection between elastic part 310 and cassette sample addition nozzle 300 is not limited to the above-mentioned ways, and can be set according to the actual situation. All structures that can realize the rotatable connection between elastic part 310 and cassette sample addition nozzle 300 are possible.

In some embodiments, lid 400 can be an independent lid 400 separated from cassette sample addition nozzle 300, and lid 400 directly covers on cassette sample addition nozzle 300 by means of buckle connection or screwing. The upper part of through-hole 301 of cassette sample addition nozzle 300 is provided with inclined surface 302. Inclined surface 302 is convenient for lid 400 to be closed on the one hand, and on the other hand, when the sample is added, it can completely fall into sample addition compartment 110 along inclined surface 302.

In the cartridge of the present embodiment, sample addition compartment 110 is used to store the samples added by cassette sample addition nozzle 300, wherein, sample addition compartment 110 is composed of first sealing film 1200 and the sample addition chamber, and siphon tube 120 is composed of siphon part 121 and first sealing film 1200. Since the bottom of the sample addition chamber and siphon part 121 are communicated to each other, the sample added to cassette sample addition nozzle 300 will directly enter sample addition compartment 110 and siphon tube 120. Since the structure of siphon part 121 is a U-shaped structure, the sample stays in siphon tube 120 and sample addition compartment 110, and lid 400 is closed on cassette sample addition nozzle 300 to seal it, so that the sample in sample addition compartment 110 cannot flow out from cassette sample addition nozzle 300, and after lid 400 is closed on cassette sample addition nozzle 300, each chamber in cartridge body 100 is completely sealed.

Wherein, the bottom of sample addition chamber 111 is provided with the inclined surface, the inclined surface is convenient to gather the sample at the bottom of sample addition chamber 111, so that the sample enters siphon tube 120, and the inclined surface is a smooth transition structure which can also reduce the residual volume of liquid in the sample chamber.

Sample addition compartment 110 and siphon tube 120 act together in such a way that the sample is able to stay stably within sample addition compartment 110 and siphon tube 120 in the absence of other forces, even when the first flow channel hole is not closed, the sample does not enter sample lysis compartment 130 and thus flow into sample filtration compartment 140. Since the sample has to react within sample lysis compartment 130, the sample must stay in sample lysis compartment 130, and cannot directly enter sample filtration compartment 140 for filtration. Under the combined action of sample addition compartment 110 and siphon tube 120, the sample will not directly enter sample lysis compartment 130 due to capillary action, and will not enter sample filtration compartment 140. Therefore, it is not necessary to close the first flow channel hole. Furthermore, there is no need to control the first flow channel hole, and there is no need to control the first flow channel hole. Further, the operation of adding samples to the cartridge without being installed on the testing device is realized, and the cartridge can be directly removed for sample adding, which improves the convenience of adding the sample and reduces the requirements for sample addition steps.

Siphon tube 120 is a reciprocating folded-back structure. Specifically, siphon tube 120 comprises inlet connecting portion 1221, first straight portion 1211, first curved portion 1212, second straight portion 1213, second curved portion 1214, third straight portion 1215 and outlet connecting portion 1222, one end of inlet connecting portion 1221 communicates with the bottom of sample addition compartment 110, one end of first straight portion 1211 communicates with the other end of inlet connecting portion 1221, the other end of first straight portion 1211 communicates with one end of first curved portion 1212, one end of first curved portion 1212 communicates with one end of second straight portion 1213, and one end of second straight portion 1213 communicates with one end of second curved portion 1214. The other end of second curved portion 1214 communicates with one end of third straight portion 1215, and the other end of third straight portion 1215 communicates with the outlet connecting portion 1222.

Sample addition compartment 110, inlet connecting portion 1221 and first straight portion 1211 together form a first U-shaped structure. When the cartridge is placed vertically, the sample enters sample addition compartment 110, inlet connecting portion 1221 and the first straight portion 1211. The first U-shaped structure effectively prevents the sample from directly entering sample lysis compartment 130 and sample filtration compartment 140, thus preventing testing failure.

Second straight portion 1213, second curved portion 1214 and third straight portion 1215 together form a second U-shaped structure, and the second U-shaped structure can further avoid the problem of the sample entering directly into sample lysis compartment 130 and sample filtration compartment 140, which leads to detection failure. Even if some samples cross over the first U-shaped structure, it will stay on the second U-shaped structure and cannot enter sample lysis compartment 130.

First choke valve 801 is provided in first straight portion 1211. First choke valve 801 is used to allow the sample to flow through first straight portion 1211 when it is open, and when first choke valve 801 is closed, the sample and/or air is blocked by first choke valve 801 and cannot flow through; first choke valve 801 can further prevent the sample and/or air from entering sample lysis compartment 130, thus can be directly controlled by first choke valve 801, thus can more effectively avoid the problem of the sample entering directly into sample lysis compartment 130 and sample filtration compartment 140, resulting in the failure of detection. Moreover, with first choke valve 801, the cartridge can be placed horizontally without the need to be placed vertically, and the sample will not flow into sample lysis compartment

130, which can effectively prevent the sample from spreading everywhere in the cartridge channel, affecting the detection accuracy.

Third straight portion 1215 is provided with a second choke valve. When the second choke valve is opened, the sample can flow through second straight portion 1213. When the second choke valve is closed, the sample and/or air are blocked by the second choke valve and cannot flow through; under the action of first choke valve 801, the second choke valve can further prevent the sample and/or air from directly entering sample lysis compartment 130, Moreover, it can be used as a backup choke valve. When first choke valve 801 cannot work effectively, the second choke valve can work effectively to prevent the sample from directly entering sample lysis compartment 130.

In some embodiments, a U-shaped structure is used to communicate sample addition compartment 110 and sample lysis compartment 130, specifically, one end of the inlet connecting portion 1221 communicates with the bottom of sample addition compartment 110, and the other end of the inlet connecting portion 1221 communicates with one end of communicating portion 1210, the other end of communicating portion 1210 communicates with one end of outlet connecting portion 1222, the other end of outlet connecting portion 1222 communicates with the upper part of sample lysis compartment 130, and communicating portion 1210 can be directly a first communicating tube.

Communicating portion 1210 can also be first straight portion 1211, first curved portion 1212, second straight portion 1213, second curved portion 1214, and third straight portion 1215, thereby forming the double U-shaped structure of this embodiment. First choke valve 801 and the second choke valve are both disposed on communicating portion 1210, and communicating portion 1210 does not necessarily have only first choke valve 801 and the second choke valve, but may also have other choke valves. For achieving flow blocking and preventing the sample and/or air from entering into sample lysis compartment 130 this example requires only at least one flow blocking valve on communication portion 1210.

In some embodiments, while adopting the above-mentioned U-shaped structure, first choke valve 801 is provided on first straight portion 1211, and first choke valve 801 is used to further avoid samples and/or air directly enter sample lysis compartment 130 and sample filtration compartment 140, resulting in the problem of detection failure. At the same time, the cartridge can be directly placed horizontally without being placed vertically, and the sample will not flow into sample lysis compartment 130, which can effectively prevent the sample from spreading everywhere in the channel of the cartridge, affecting the detection accuracy.

In some embodiments, adopting the first U-shaped structure and the second U-shaped structure in the above-mentioned sample addition compartment 110 and sample lysis compartment 130 can effectively prevent the sample from directly entering sample lysis compartment 130 and sample filtration compartment 140, which affects the detection accuracy.

In some embodiments, siphon tube 120 in the present example is not used, but a communication channel is directly provided between sample addition chamber 111 and sample lysis compartment 130 for communication, and a choke valve is provided in the communication channel, to control the flow of the sample and/or air in the communication channel through the choke valve, which can also achieve the problem of avoiding the direct entry of the sample into sample lysis compartment 130 and the sample filtration compartment, resulting in detection failure. At the same time, it can be realized that the cartridge can be placed horizontally without the need to be placed vertically, and the sample will not flow into sample lysis compartment 130, which can effectively prevent the sample from spreading everywhere in the channel of the cartridge, affecting the detection accuracy.

In the cartridge of the present embodiment, sample lysis compartment 130 is used as a reaction site for lysing the sample, and sample lysis compartment 130 is comprised of sample lysis chamber 132 and first sealing film 1200. Sample lysis compartment 130 is heated by the heating module of the device, and after the temperature reaches the temperature required for sample lysis, the sample is lysed.

Wherein, sample lysis chamber 132 is provided with plate 131, and plate 131 is vertically arranged in the middle position of sample lysis chamber 132, facing the junction of siphon part 121 and sample lysis chamber 132; In a specific embodiment, plate 131 is a long plate, and its cross-section is a long rectangle shape; plate 131 of the present invention has the following effects:

1) Plate 131 can play a buffering role to prevent the splashing generated by the excessively fast flow rate when the sample enters sample lysis compartment 130;

2) a plurality of valves provided on the cartridge needs an external force to realize their function, when the valves are unevenly distributed on the cartridge, it will lead to uneven forces on the entire cartridge. In order to balance the entire cartridge and prevent the cartridge from being bent and deformed, plate 131 can provide a force-bearing part for the cartridge, and a force is applied to the cartridge from the position of plate 131, which can play a role in balancing the force applied to the cartridge.

3) In the thermal lysis process, due to the heating of sample lysis compartment 130, the compartment itself will be thermally expanded, and after applying force to plate 131, it can also play the role of preventing the excessive expansion of the sealing film.

In the cartridge of this embodiment, before the sample enters sample lysis compartment 130 through siphon tube 120 from sample addition compartment 110, first ejector valve 510 needs to be closed, so that the sample in sample lysis compartment 130 will not flow into sample filtration compartment 140 to ensure that the sample can be fully lysed in sample lysis compartment 130. If some samples pass through first ejector valve 510 before being fully lysed and enter first flow channel 2510 and flow into sample filtration compartment 140, it will lead to inaccurate test results or even test failure;

Therefore, before the sample enters sample lysis compartment 130 from sample addition compartment 110 through siphon tube 120, first sealing film 1200 at the position of first ejector valve 510 needs to be compressed by an external force, so that the compressed force is transmitted to the first rubber cushion through first sealing film 1200, and the first rubber cushion is compressed and deformed, blocking the first flow channel hole, so that the sample cannot flow through first flow channel 2510 and into sample filtration compartment 140 through the first flow channel hole.

Wherein, first ejector valve 510, second ejector valve 520, third ejector valve 530, fourth ejector valve 540, fifth ejector valve 550, sixth ejector valve 560 and seventh ejector valve 570 are ejector valve with completely identical structure. Therefore, the following descriptions, explanations and effects of the structure of ejector valve 15 are applicable for first ejector valve 510, second ejector valve 520, third ejector valve 530, fourth ejector valve 540, fifth ejector valve 550, sixth ejector valve 560 and seventh ejector valve 570.

Ejector valve 15 comprises valve chamber 511, rubber cushion 512 and at least one bulged part 5111. Valve chamber 511 is provided with opening 5113 on the side, and flow channel hole 5112 on the bottom. Rubber cushion 512 is located above flow channel hole 5112. Bulged part 5111 is provided on the surface of rubber cushion 512 facing valve chamber 511, and/or at a position corresponding to rubber cushion 512 on the surface of valve chamber 511, so that a gap for the sample to flow in can be formed between undeformed rubber cushion 512 and flow channel hole 5112, and rubber cushion 512 is used to deform when being compressed and block flow channel hole 5112.

Figure 2:
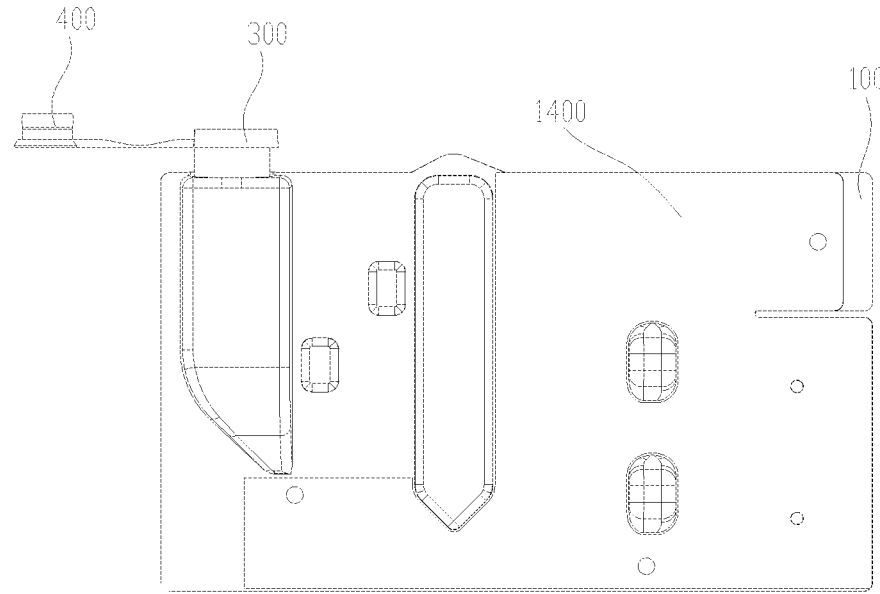
FIG. 2 is the back view of the cartridge in Example 1 of the present invention.

The working principle of ejector valve 15 structure proposed by present application is: due to the existence of the bulged part 5111, when rubber cushion 512 is not subject to external force (not deformed), referring to FIG. 2 and FIG. 3, due to the existence of the gap between rubber cushion 512 and channel holes 5112, the liquid sample can flow into valve chamber 511 from the opening 5113, and then flow into flow channel hole 5112, so as to flow out of ejector valve 15 structure along the flow channel. When rubber cushion 512 is subjected to a predetermined pressure, it will deform, and when rubber cushion 512 is deformed to block flow channel hole 5112, the liquid cannot flow into or out of flow channel hole 5112, i.e., it cannot pass through the structure of ejector valve 15, so the structure of ejector valve 15 can play the role of blocking the flow of liquid. Due to the elasticity of rubber cushion 512, when the external force is removed, rubber cushion 512 returns to its original state, i.e. a state where there is a gap between rubber cushion 512 and flow channel hole 5112, and the liquid can flow through the structure of ejector valve 15.

Ejector valve 15 proposed by the present invention has a simple structure, and the fluid control effect is reliable, and ejector valve 15 work can be controlled only by pressing action, effectively simplifying the operation of the supporting instrument.

When rubber cushion 512 is deformed under the compression of the external force, rubber cushion 512 enters the middle of the three bulged parts 5111, blocks flow channel hole 5112, and prevents the sample from flowing through first flow channel 2510 through flow channel hole 5112 into sample filtration compartment 140. Since rubber cushion 512 has elasticity, when the external force acts, rubber cushion 512 has a restoring elastic force, and when the external force is removed, rubber cushion 512 is restored to its original shape and placed on the top of the three bulged parts 5111, the sample flows through first flow channel 2510 through flow channel hole 5112 and flows into sample filtration compartment 140. Ejector valve 15 comprises a valve chamber and a rubber cushion, and the bottom of the valve chamber is provided with a flow channel hole and several bulged parts;

The rubber cushion is placed above the bulged part, and the bulged part supports the rubber cushion, so that a gap for the sample to flow into is formed between the undeformed rubber cushion and the flow channel hole, and the rubber cushion is used to block the flow channel holes when deformed by compressing.

Wherein, the gap between the three bulged parts 5111 can also be the same, or the interior of three bulged parts 5111 is provided with a hole, and the hole can be used for the sample to pass through; three bulged parts 5111 can be directly replaced by a convex ring, the convex ring is provided with a number of apertures, which can allow the sample to pass through, all the above structures can realize the function of first ejector valve 510 in this example.

In addition, bulged parts 5111 can be at least two or one, and when bulged part 5111 is one, the bulged part 5111 can lift rubber cushion 512 when the rubber cushion is not deformed, so that there provides a gap between the undeformed rubber cushion and flow channel hole 5112 for the sample to flow in, and rubber cushion 512 deforms when being compressed to block the flow channel hole, and the function of ejector valve 15 can also be realized.

The height of the bulged part in the present example is 0.2 mm, and the height of the entire ejector valve 15 is 1.2 mm, and the bulged part accounts for about 16.7% of the height of the entire ejector valve 15, and the thickness of the rubber cushion of the present example is 1 mm, the hardness is 40 A. For example, when the height of the bulged part increases, a rubber cushion with a softer hardness can be selected; and when the height of the bulged part decreases, a rubber cushion with a higher hardness can be selected. According to the fact that the bulged part accounts for 5%-30% of the height of the entire ejector valve 15, the rubber cushion with the hardness in the range of 60 A-30 A can be selected. In the above description of the structure of ejector valve 15, first ejector valve 510, second ejector valve 520, third ejector valve 530, fourth ejector valve 540, fifth ejector valve 550, sixth ejector valve 560 and seventh ejector valve 570 and other ejector valves can be applied.

Ejector valve 15 in the present example has good tightness, can realize automatic reset at the same time, and cannot react with the sample and the reagent in the cartridge that may cause test error.

In some embodiments, the structure of ejector valve 15 can also be: the bottom of valve chamber 511 is provided with a flow channel hole 5112, three bulged parts 5111 are disposed on rubber cushion 512, and the three bulged parts 5111 are arranged along the rubber cushion 511. The center of the bottom surface of rubber cushion 512 is surrounded by a certain gap, rubber cushion 512 is arranged in valve chamber 511, and the center of the bottom surface of the rubber cushion 512 corresponds to the center of flow channel hole 5112;

When rubber cushion 512 is not compressed by an external force, i.e., in the open state of ejector valve 15, the sample flows through the gaps of the three bulged parts 5111, or directly flows through the bottoms of the three bulged parts 5111, and flows into flow channel hole 5112, and flows into first flow channel 2510 through flow channel hole 5112;

When rubber cushion 512 is compressed by an external force, rubber cushion 512 is deformed, the three first bulged parts are compressed against the bottom of the valve chamber, and the center of rubber cushion 512 blocks flow channel hole 5112, so that the sample cannot pass through flow channel hole 5112, i.e. the closed state of the first ejector valve 15.

When removing the external force that compresses rubber cushion 512, under the action of the elasticity of three bulged parts 5111 and rubber cushion 512 itself, rubber cushion 512 restores its original shape, i.e., ejector valve 15 returns to the open state for use next time.

In this embodiment, bulged parts 5111 can be one, two or four, which can be realized. The bulged part 5111 mainly supports rubber cushion 512 for the sample to enter flow channel hole 5112. When rubber cushion 512 is compressed, rubber cushion 512 can seal flow channel hole 5112.

In some embodiments, the structure of ejector valve 15 can also be: the bottom of valve chamber 511 is provided with a flow channel hole 5112 and a convex ring, and the periphery on rubber cushion 512 is provided with several holes, and the sample can enter flow channel hole 5112 through the peripheral holes on rubber cushion 512.

When rubber cushion 512 is compressed by an external force, rubber cushion 512 is deformed, and the center of rubber cushion 512 blocks flow channel hole 5112, so that the sample cannot flow into first flow channel 2510 through flow channel hole 5112, i.e., ejector valve 15 is in a closed state.

When the external force compressing rubber cushion 512 is removed, rubber cushion 512 returns to its original shape under the elasticity of the convex ring and rubber cushion 512 itself, i.e., ejector valve 15 returns to the open state for the next use.

In this embodiment, the center of rubber cushion 512 can be further provided with a bulged part i.e. adapting to flow channel hole 5112. In the closed state of ejector valve 15, the bulged part is inserted to block flow channel hole 5112. Flow channel hole 5112 can be blocked more effectively to prevent the sample from flowing into flow channel hole 5112.

In some embodiments, ejector valve 15 in the present embodiment is not used for control, and the adopted method can be providing a choke valve at the bottom of sample lysis chamber 132, or, providing valve chamber 511 and flow channel hole 5112, and then providing a magnetic element, and providing a sealing layer on the magnetic element; it is controlled by the external magnetic device, when sealing is required, the sealing layer of the magnetic element is pressed against the flow channel hole 5112 in the way of opposites attract repulsion through the external magnetic device, so that flow channel hole 5112 is sealed, preventing the sample from entering flow channel hole 5112.

The function to be realized by ejector valve 15 is: in the closed state, flow channel hole 5112 is sealed to prevent the sample from flowing into sample filtration compartment 140 through first flow channel 2510 through flow channel hole 5112; and in the open state, flow channel hole 5112 is opened, so that the sample flows through first flow channel 2510 through flow channel hole 5112 and flows into sample filtration compartment 140. According to this embodiment and other embodiments described above, ejector valve 15 may also be other valves or switches capable of realizing the above functions.

Wherein, rubber cushion 512 can also adopt the rubber cushions that have elasticity and inertness and are not easy to adsorb nucleic acid, such as natural rubber cushion, EPDM rubber cushion and nitrile rubber cushion, etc. The rubber cushion used in this embodiment is a silicone rubber cushion, which avoids the impact on the test caused by the problem of the cartridge during the test process.

In the cartridge of the present embodiment, sample filtration chamber 141 is used for filtering the impurities of macromolecules, mainly filtering out macromolecules exceeding 200 nm in the sample, and preventing the impurities of macromolecules from blocking the subsequent one or more channels of second channel 2520, third channel 2530, fourth channel 2540, fifth channel 2550, sixth channel 2560 and seventh channel 2570, which may reduce the test efficiency, and if any flow channel is blocked, the test may fail.

Filtration films such as terylene or nylon filtration film etc. that can realize macromolecular filtration can be employed, filtration film is preferably nylon filtration film, which is low in price and can better realize the effect of filtration, effectively reduces the cost of the cartridge, especially in the mass production process; and in the PCR test, it is found that the use of polyester or nylon filtration film has little negative impact on the test results.

In the cartridge in this embodiment, first sample mixing chamber 1511 and second sample mixing chamber 1521 may be chambers of the same shape and size, or may be chambers of different structures, shapes and sizes. First sample mixing compartment 151 is composed of first sample mixing chamber 1511 and first sealing film 1200, and second sample mixing compartment 152 is composed of second sample mixing chamber 1521 and first sealing film 1200.

First mixing bead 710 and first lyophilized bead 610 are located in first sample mixing compartment 151, and second mixing bead 720 and second lyophilized bead 620 are located in second sample mixing compartment 152; first lyophilized bead 610 and second lyophilized bead 620 are nucleic acid amplification reaction reagents set according to the actual target to be detected. Generally, according to different targets, first lyophilized bead 610 and second lyophilized bead 620 are different lyophilized beads, so that the cartridge can detect multiple different targets at the same time, which improves the detection function and detection efficiency of the cartridge.

The working mode and process of first sample mixing compartment 151 and second sample mixing compartment 152 are the same, but only for different targets. Therefore, taking first sample mixing compartment 151 as an example, first lyophilized bead 610 will be redissolved after the sample enters, and then by controlling first mixing bead 710 to move up and down, the redissolved lyophilized bead powder and the sample are fully mixed and shaken evenly, so as to achieve stable subsequent nucleic acid amplification;

First lyophilized bead 610 is placed in first sample mixing compartment 151 instead of using powdered reagents, because if the powdered reagents are used, when the sample enters first sample mixing compartment 151, the redissolution effect of powdered lyophilized reagents is unsatisfying, and the production process is difficult to control, and during transportation or placement, the powder easily enters other compartments which may result in poor nucleic acid amplification effects and even test failures. If the reagent is lyophilized in situ, the whole cartridge needs to be put into the lyophilizing compartment for lyophilization during the production process of the cartridge, so the production efficiency of the cartridge will be relatively low, and the redissolution effect of the in-situ lyophilized reagent will be less effective than that of the lyophilized bead.

The main components of first lyophilized bead 610 and second lyophilized bead 620 not only comprise the essential ingredients for nucleic acid detections such as primers, probes, reverse transcriptase, hot-start enzymes, dNTPs, strengthening agent, surfactants, salts and preservatives, etc. At the same time, substances such as excipients and protective agents must also be included. Excipients are usually inert substances, including sucrose, glucose, trehalose, melezitose, dextran, and mannitol, etc. The dosage of the excipient should be appropriate, a small amount makes it difficult to form, and a large amount makes it difficult to re-dissolve. In the cartridge of this embodiment, since first lyophilized bead 610 and first mixing bead 710 are stored in first sample mixing compartment 151 at the same time, the hardness of first lyophilized bead 610 needs to fulfill special requirements. If the amount of excipient is too small, it is easy to be broken by the impact of first mixing bead 710 during transportation, which affects the performance of subsequent reagent tests. But excessive excipient will increase the redissolution time of first lyophilized bead 610 and the mixing time of first mixing bead 710, and the same applies for second lyophilized bead 620. The weight of the excipient of first lyophilized bead 610 used in this embodiment accounts for 20%-60% of the total weight of first lyophilized bead 610 and the excipient of second lyophilized bead 620 accounts for 20%-60% of the total weight of second lyophilized bead 620, so that first lyophilized bead 610 can be effectively prevented from being broken by the impact of first mixing bead 710 during transportation, and at the same time, the time for redissolution of first lyophilized bead 610 and the time for first mixing bead 710 to be mixed will not be increased too much.

The design of aforementioned sample mixing compartment is such that it can accommodate both the mixing bead and the lyophilized bead while being as small as possible. The purpose is as follows:

1. The volume of the sample mixing compartment should not be too large to avoid collision between the mixing bead and the lyophilized bead during transportation. If the volume of the sample mixing compartment is too large, the movement space of the two kinds of beads will be large, so that the mixing bead can accumulate more kinetic energy to hit the lyophilized bead, causing the lyophilized bead to be more susceptible to damage.

2, the volume of the sample mixing compartment also cannot be too small. This is to ensure that the mixing bead has enough space for up and down movement, so that the sample and the reagent after the lyophilized bead redissolution can be effectively mixed and moved.

First lyophilized bead 610 has a stable structure and can stay in the sample mixing compartment, and when the sample enters, the contact area of the sample and first lyophilized bead 610 is increased due to the porous structure inside first lyophilized bead 610, which enhances the redissolution effect, and is easy to control, as well as due to the morphology of first lyophilized bead 610, there will be no problem that the powder-like reagent enters other compartments. Second lyophilized bead 620 is the same as first lyophilized bead 610.

First mixing bead 710 can move in first sample mixing compartment 151 under the action of an external magnet. The movement can be at various angles to shake and mix the re-dissolved first lyophilized bead 610 and the sample. As a result, the re-dissolution of first lyophilized bead 610 is accelerated, first lyophilized bead 610 and the sample can be thoroughly mixed to ensure that the test results have a high consistency.

First mixing bead 710 and second mixing bead 720 can be round beads made of iron or alloys, or beads of other materials that can be adsorbed by magnets but cannot adsorb nucleic acids, etc. Under the action of magnetic force, first lyophilized bead 610 or second lyophilized bead 620 are crushed and redissolved by moving in the corresponding sample mixing compartment, and first lyophilized bead 610 or second lyophilized bead 620 are mixed and stirred. Their shapes are not necessarily spherical, and can also be a polyhedron or other structure, i.e., first mixing bead 710 can be a first mixing component, and second mixing bead 720 can be a second mixing component.

In first sample mixing compartment 151, when the sample enters first sample mixing compartment 151, first lyophilized bead 610 is re-dissolved and mixed with the sample, and the up and down movement of first mixing bead 710 is controlled by the action of an external magnet, and while first lyophilized bead 610 being hit, the reagents redissolved in first lyophilized bead 610 in first sample mixing compartment 151 and the sample are mixed and stirred to fully and efficiently mix first lyophilized bead 610 with the samples, so that after the samples mixed with the reagents enter first PCR compartment 161, the PCR reaction can be performed, and results with high consistency can be obtained, thus effectively improving the reliability of subsequent sample detection (CV will be smaller).

After re-disposing the first lyophilized bead 610, it is critical to ensure that the concentration of the re-dissolved sample is uniform, so that the consistency of the reagent reaction system entering the first PCR compartment 161 is high every time. First mixing bead 710 and first lyophilized bead 610 are placed in first sample mixing compartment 151; by shaking first mixing bead 710 up and down, first lyophilized bead 610 is made to undergo rapid re-dissolution, and at the same time the concentration of the samples after re-dissolution of the first lyophilized bead 610 can be uniformly achieved, thereby ensuring that the consistency of the reagent reaction system in first PCR compartment 161 is maintained in a relatively high range. Using up-and-down shaking and stirring of first mixing bead 710 can quickly mix first lyophilized bead 610 with the sample, thereby improving the redissolution efficiency of first lyophilized bead 610 and the mixing efficiency of first lyophilized bead 610 with the sample.

Being identical to first sample mixing compartment 151, second sample mixing compartment 152 enables rapid mixing of the sample and PCR reaction reagents to enable subsequent mixing of the sample with the reagents into the first PCR compartment 161 for PCR reactions that can yield consistent results; thereby improving the reliability of the PCR reactions in second PCR compartment 162.

First PCR compartment 161 is comprised of second sealing film 1400, first PCR chamber 1611 and third sealing film 1300, and second PCR compartment 162 is comprised of second sealing film 1400, second PCR chamber 1621 and third sealing film 1300 is formed; the temperature of first PCR compartment 161 and second PCR compartment 162 is heated and cooled, and then the amplified nucleic acid corresponding to the optical detection device is detected to obtain the detection result.

First PCR compartment 161 corresponds to first sample mixing compartment 151, determined by the reagents of first lyophilized bead 610 in first sample mixing compartment 151, first lyophilized bead 610 is set for the nucleic acid required for amplification. In this embodiment, first PCR compartment 161 is used to detect COVID-19, and the corresponding first lyophilized bead 610 is an enzyme and other reagents formulated according to COVID-19. Second PCR compartment 162 is used for the determination of FluA/FluB, and the corresponding second lyophilized bead 620 are also formulated according to the enzymes and other reagents of FluA/FluB. Wherein, first PCR compartment 161 and second PCR compartment 162 can both detect multiple targets in one PCR compartment; in order to avoid interference between the targets, it is best not to detect more than three targets in each PCR compartment; First PCR compartment 161 and second PCR compartment 162 in this embodiment realize the detection of multiple targets with high sensitivity.

When liquid to be detected is filled in first PCR compartment 161, and when fourth channel 2540 is filled with the liquid, fourth ejector valve 540 and sixth ejector valve 560 are closed at this moment, closing fourth ejector valve 540 will cause excessive pressure in first PCR compartment 161 and fourth channel 2540 due to the liquid already in fourth channel 2540, and the above pressure will directly act on second sealing film 1400 and third sealing film 1300; when the above pressure is too high, it will cause either or both of second sealing film 1400 and third sealing film 1300 to burst, resulting in liquid leakage, thereby causing detection failure; and if either or both of second sealing film 1400 and third sealing film 1300 are burst, it will cause samples with viruses to enter the environment and even cause infection of the testing operators;

In addition, due to the need to perform temperature heating and cooling during the detection in first PCR compartment 161, when first PCR compartment 161 and fourth channel 2540 are both filled with samples, in the process of heating and cooling, due to the principle of thermal expansion and contraction, the pressure in first PCR compartment 161 increases and third sealing film 1300 is compressed, which easily causes third sealing film 1300 to be burst, resulting in liquid leakage, which in turn leads to the failure of detection and the entry of virus-containing samples into the environment, and even cause the problem of infection of testing operators.

For the above-mentioned risks and problems, cartridge body 100 is provided with first damping chamber 1010, and first damping chamber 1010 communicates with the top of first PCR chamber 1611; first damping chamber 1010 is disposed on the second surface of cartridge body 100, the first damping chamber 1010 and second sealing film 1400 together form first damping compartment 1011; when the sample fills first PCR compartment 161 and fourth channel 2540, fourth ejector valve 540 is closed, and the sample can enter first damping compartment 1011, thereby avoiding the problem of excessive pressure in first PCR compartment 161 and fourth channel 2540, thereby effectively solves the problem of excessive pressure in first PCR compartment 161 and fourth channel 2540, causing either or both of second sealing film 1400 and third sealing film 1300 to be burst, resulting in leakage, which in turn leads to test failure and the introduction of samples with viruses into the environment, resulting in infection of testing operators;

And, the first damping compartment communicates with the first PCR compartment; When the first PCR compartment is filled with liquid to be detected is heated and cooled, since the first PCR compartment is in a closed state under the control of the valve, the liquid cannot be removed from the first PCR compartment, and when the temperature rises, the pressure in the first PCR compartment will be too high, and the first damping compartment communicated with the first PCR compartment can allow the thermally expanded liquid to flow into it, thereby avoiding the problem of excessive pressure in the first PCR compartment, this can effectively solve the problem of the first PCR compartment being ruptured due to the excessive pressure in the first PCR compartment, which results in liquid leakage, and in turn leads to the failure of detection and the introduction of virus-containing samples into the environment, and infection of testing operators. When the temperature is lowered, the pressure in the first PCR compartment becomes smaller, and the liquid in the first damping chamber flows into the first PCR compartment under the action of pressure, so that good contact between the heating and cooling device and the first PCR compartment can be maintained, which avoids the problem of poor contact between the heating and cooling device and the first PCR compartment after cooling due to volume expansion of the first PCR compartment during heating.

First damping compartment 1011 is a channel structure, one end of first damping compartment 1011 communicates with first PCR compartment 161, and the other end is closed, when first PCR compartment 161 is filled, a gap is reserved in first damping compartment 1011. Specifically, first damping compartment 1011 is a slot provided on the cartridge, which is sealed by welding a sealing film on the surface to form a sealed channel structure, or an internal channel that can be dug out of the cartridge as first damping compartment 1011, wherein the gap enables the liquid to continue to flow into first damping compartment 1011 when first PCR compartment 161 is heated, so as to relieve the pressure in first PCR compartment 161 and avoid the problem of breaking first PCR compartment 161.

Wherein, the second end of first damping compartment 1011 is higher than first PCR compartment 161.

Wherein, first damping compartment 1011 is arranged in parallel with sixth channel 2560; first damping compartment 1011 is located above first PCR compartment 161, and the end of first damping compartment 1011 is bent upward.

The arrangement of first damping compartment 1011 also makes the selection of the valve more flexible and wider, which solves the problem that the pressure of first PCR compartment 161 increases due to the liquid flow when the valve is closed. Taking the preferred ejector valve in this embodiment as an example, the ejector valve has the advantages of a simple structure, reliable fluid control effect, and can flexibly switch the flow channel on the opposite surface of the cartridge, thus simplifying the operation of the supporting instrument; however, when it is closed, the pressure of first PCR compartment 161 will be increased, and the arrangement of first damping compartment 1011 can effectively solve this problem.

In the same way, second PCR compartment 162 and fifth channel 2550 also have the above-mentioned problems, thus, cartridge body 100 is provided with the second damping chamber 1020, and the second damping chamber realizes the same functions as the above-mentioned first damping chamber, The second damping chamber 1020 communicates with the upper part of second PCR chamber 1621; the second damping chamber 1020 is disposed on the second surface of cartridge body 100, and the second damping chamber 1020 and second sealing film 1400 together form the second damping compartment 1021; when the sample fills second PCR compartment 162 and fifth channel 2550, after closing fifth ejector valve 550 and seventh ejector valve 570, the sample will enter the second damping compartment 1021, thereby avoiding the problem of excessive pressure in second PCR compartment 162 and fifth channel 2550, thereby effectively solves the problem of liquid leakage due to excessive pressure in second PCR compartment 162 and the fifth channel 2550, which causes either or both of second sealing film 1400 and third sealing film 1300 to be ruptured, causing liquid leakage, which in turn leads to the failure of detection and the entry of virus-containing samples into the environment, causing infection of testing operators.

When second PCR compartment 162 filled with liquid to be detected is heated and cooled, since second PCR compartment 162 is in a closed state under the control of the valve, the liquid cannot flow out from the valve, and the pressure in second PCR compartment 162 will be too high when heating up, and the second damping compartment communicated with second PCR compartment 162 can allow the thermally expanded liquid to flow into it, so as to avoid the problem of excessive pressure in the second PCR compartment 162, causing second PCR compartment 162 to be broken, resulting in liquid leakage, which in turn leads to detection failure and the entry of virus-containing samples into the environment, causing the problem of infection of the testing operators. When the temperature is lowered, the pressure in second PCR compartment 162 becomes lower, and at this moment, the liquid in the second damping chamber flows into second PCR compartment 162 under the action of pressure, so that good contact between the heating and cooling device and second PCR compartment 162 can be maintained, which avoids the problem of poor contact between the heating and cooling device and the second PCR compartment after cooling due to volume expansion of the second PCR compartment during heating.

Wherein, first damping compartment 1011 communicates with the sixth channel, i.e., first damping chamber 1010 communicates with the sixth flow channel, and first damping compartment 1011 communicates with the sixth channel.

First damping compartment 1011 and second damping compartment 1021 are channel structures; first damping compartment 1011 and the sixth channel are substantially parallel, and second damping compartment 1021 and the eighth channel are substantially parallel.

Sample addition chamber 111 is located at the upper right of the first face of cartridge body 100, sample addition chamber 111, siphon part 121 and sample lysis chamber 132 are arranged from right to left, and sample filtration chamber 141 is located at the lower right position of cartridge body 100, and is located just below siphon part 121;

The positions of first sample mixing chamber 1511 and first PCR chamber 1611 are corresponding, and the positions of second sample mixing chamber 1521 and second PCR chamber 1621 are corresponding; first sample mixing chamber 1511 is located in the middle of cartridge body 100, first PCR chamber 1611 is located at the lower left of cartridge body 100, second sample mixing chamber 1521 is located above first sample mixing chamber 1511, and second PCR chamber 1621 is located above first PCR chamber 1611. With the above arrangement, the problem of interference caused by air bubbles can be reduced during the flow of the sample in cartridge body 100.

Figure 16:
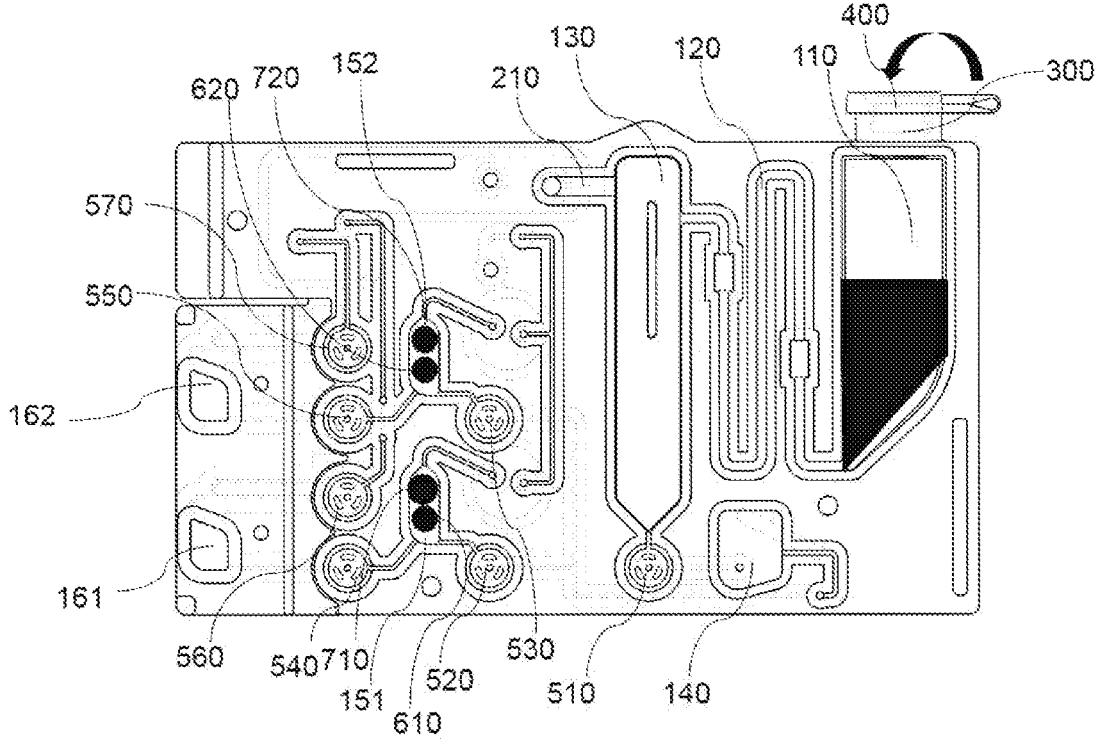
FIG. 16 is Schematic Diagram 1 of the working steps of the cartridge in Example 1 of the present invention.
Figure 17:
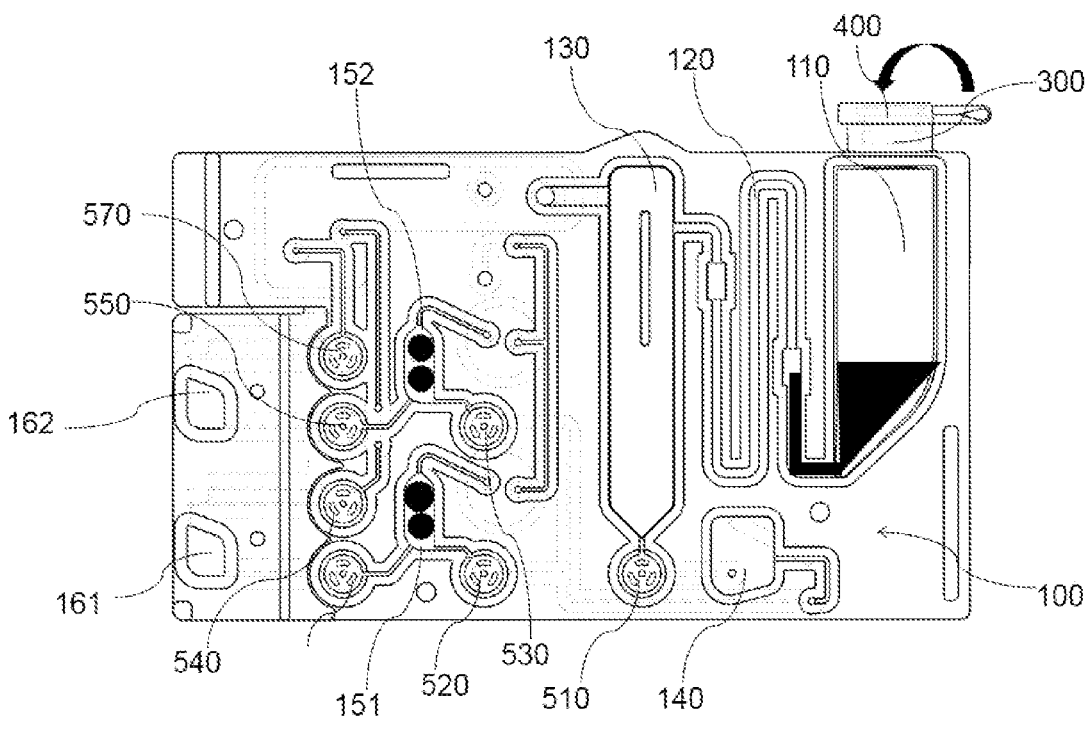
FIG. 17 is Schematic Diagram 2 of the working steps of the cartridge in Example 1 of the present invention.

As shown in FIGS. 16-33, detailed working steps of the cartridge of the present embodiment are as follows:

As shown in FIGS. 16 and 17, the first step: adding the sample into sample addition compartment 110 through cassette sample addition nozzle 300, and then pressing lid 400, lid 400 is closed on cassette sample addition nozzle 300, the cartridge is sealed by lid 400; it is ensured that lid 400 cannot be opened again after being pressed.

Figure 18:
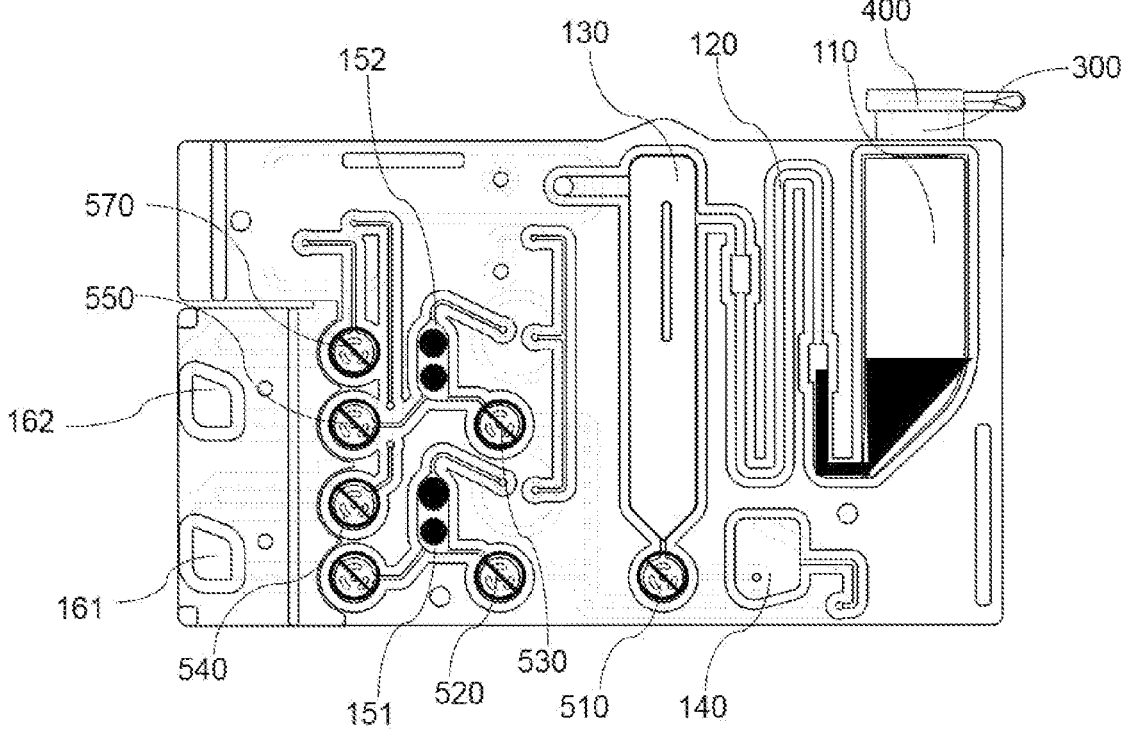
FIG. 18 is Schematic Diagram 3 of the working steps of the cartridge in Example 1 of the present invention.

Due to the action of siphon tube 120, first choke valve 801 and the second choke valve between sample addition compartment 110 and sample lysis compartment 130, the sample will stay in siphon tube 120 and will not flow into sample lysis compartment 130 due to capillary action;

As shown in FIG. 18, the second step: insert the cartridge into the testing device and fix it on the testing device. The first air pump of the testing device communicates with first air hole 201, and the second air pump of the testing device communicates with third air hole 203; wherein, the first air pump and the second air pump can be the same air pump and work through different operation ends.

Push each center rod driven by the testing device to compress first ejector valve 510, second ejector valve 520, third ejector valve 530, fourth ejector valve 540, fifth ejector valve 550, sixth ejector valve 560 and seventh ejector valve 570, so that first ejector valve 510, second ejector valve 520, third ejector valve 530, fourth ejector valve 540, fifth ejector valve 550, sixth ejector valve 560 and seventh ejector valve 570 are closed thus all channels in the cartridge are closed.

Figure 19:
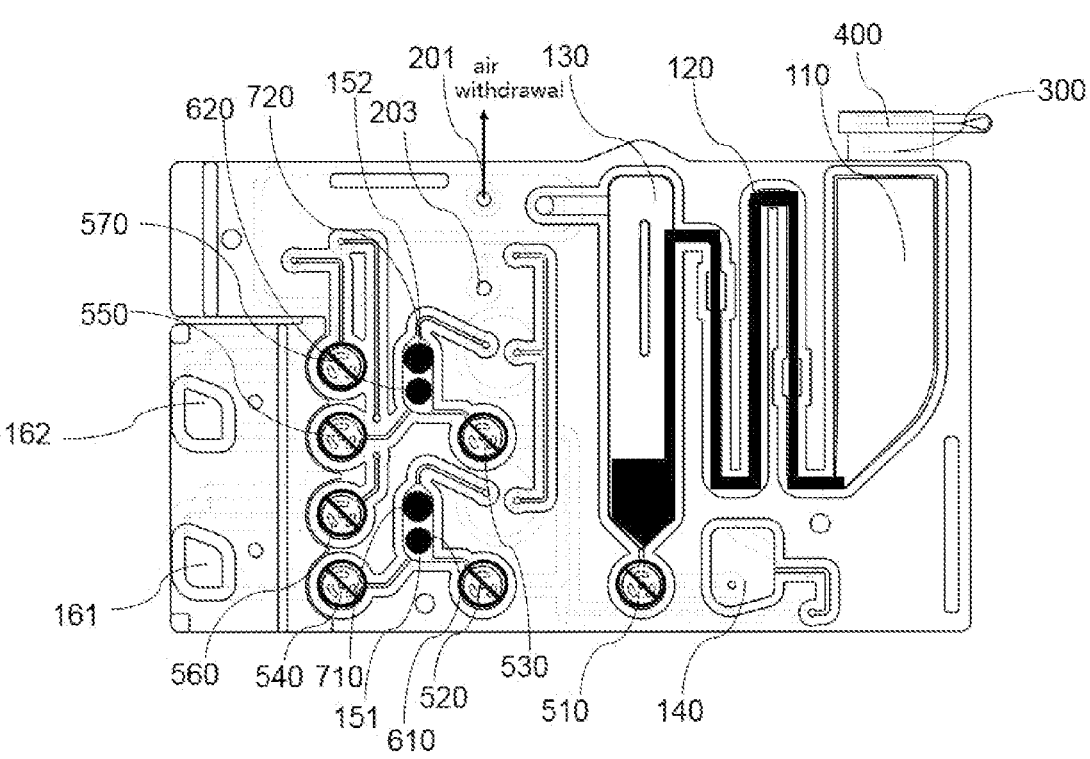
FIG. 19 is Schematic Diagram 4 of the working steps of the cartridge in Example 1 of the present invention.
Figure 20:
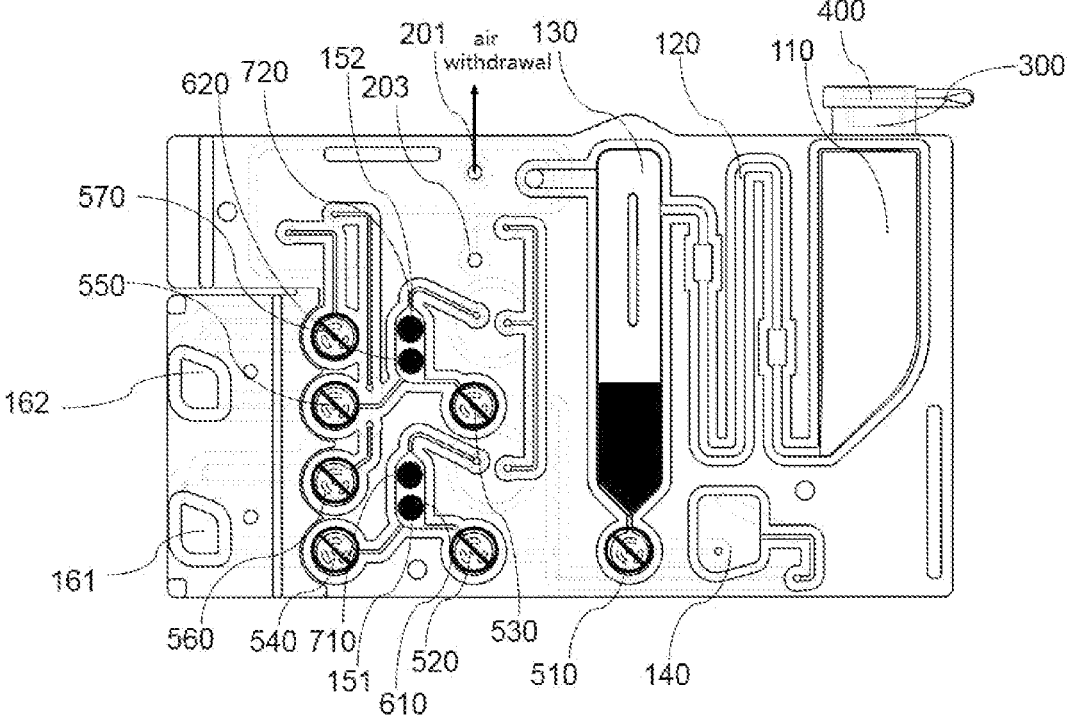
FIG. 20 is Schematic Diagram 5 of the working steps of the cartridge in Example 1 of the present invention.

As shown in FIGS. 19 and 20, the third step: drive the first air pump, draw the air in sample lysis compartment 130 through first air hole 201, first air hole 201 and second air hole 202 are communicated through first air compartment 910, therefore, the sample staying in siphon tube 120 will be pumped into sample lysis compartment 130.

Figure 21:
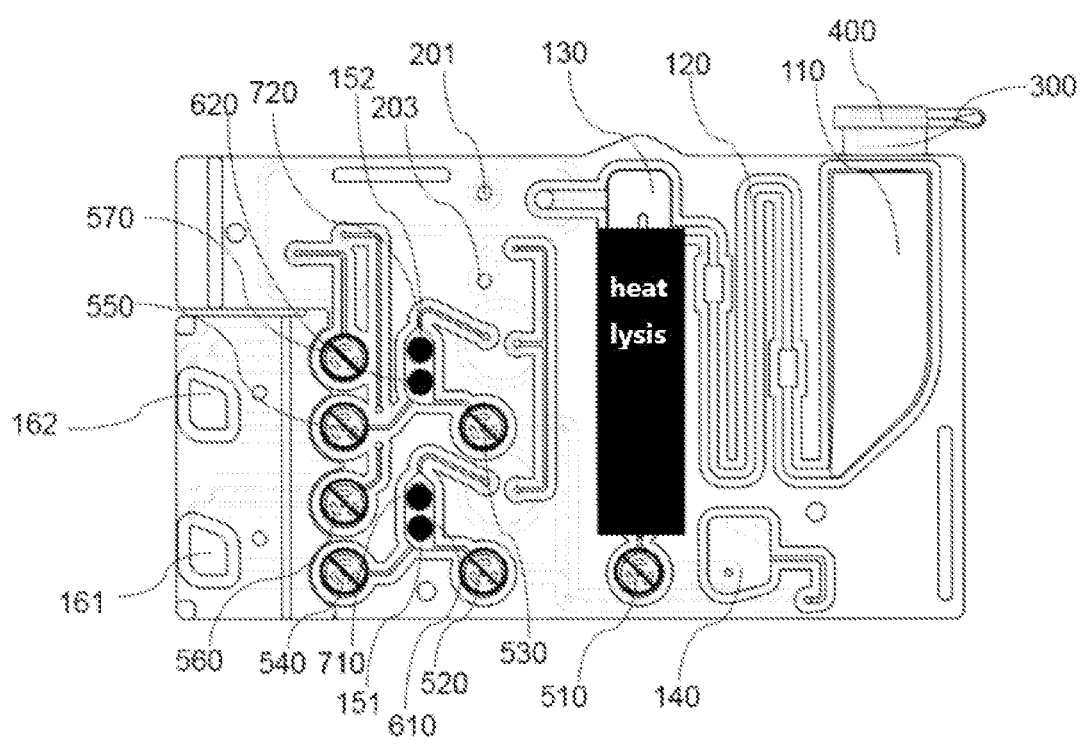
FIG. 21 is Schematic Diagram 6 of the working steps of the cartridge in Example 1 of the present invention.
Figure 22:
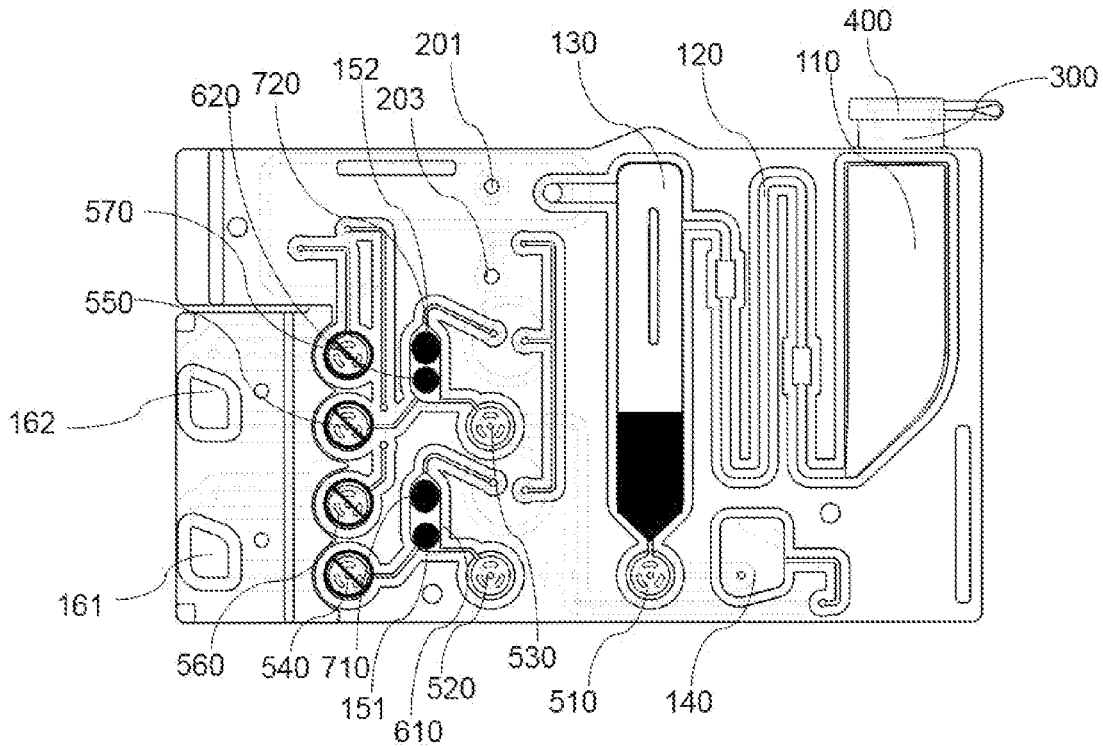
FIG. 22 is Schematic Diagram 7 of the working steps of the cartridge in Example 1 of the present invention.
Figure 23:
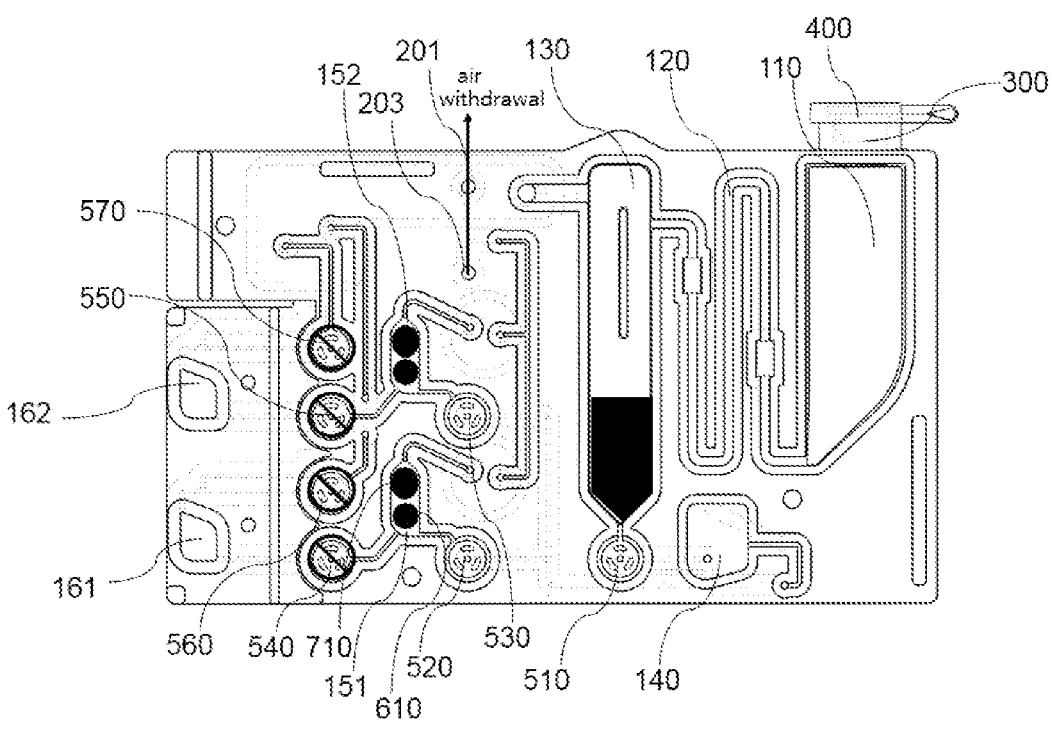
FIG. 23 is Schematic Diagram 8 of the working steps of the cartridge in Example 1 of the present invention.
Figure 24:
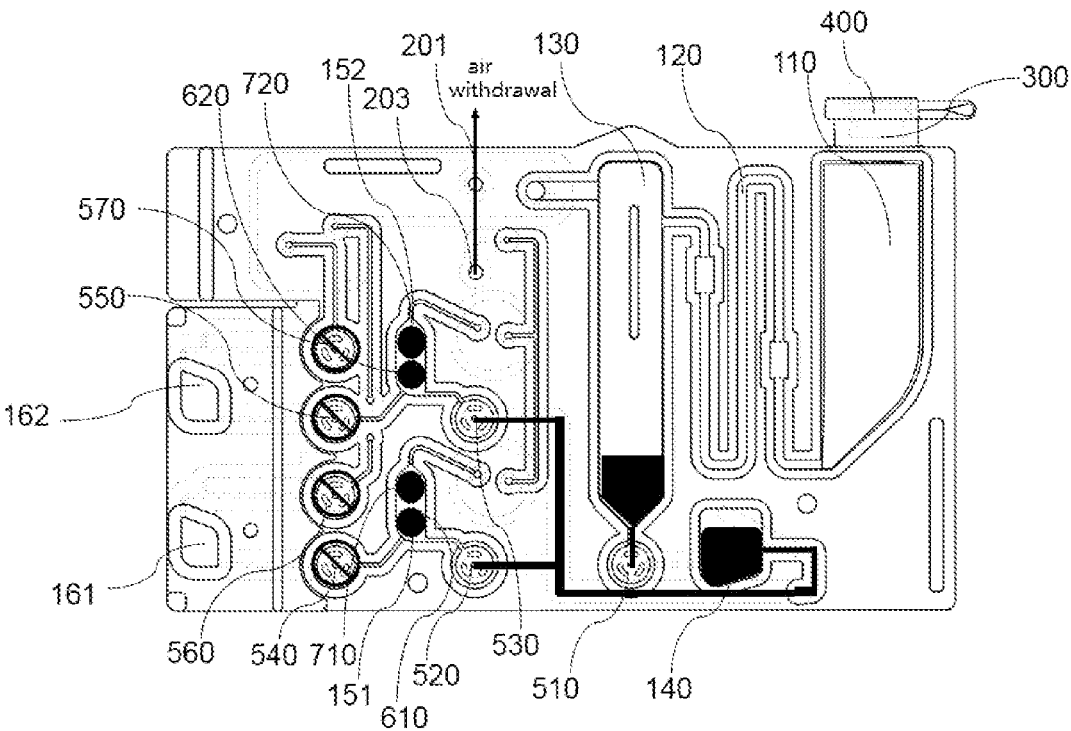
FIG. 24 is Schematic Diagram 9 of the working steps of the cartridge in Example 1 of the present invention.
Figure 25:
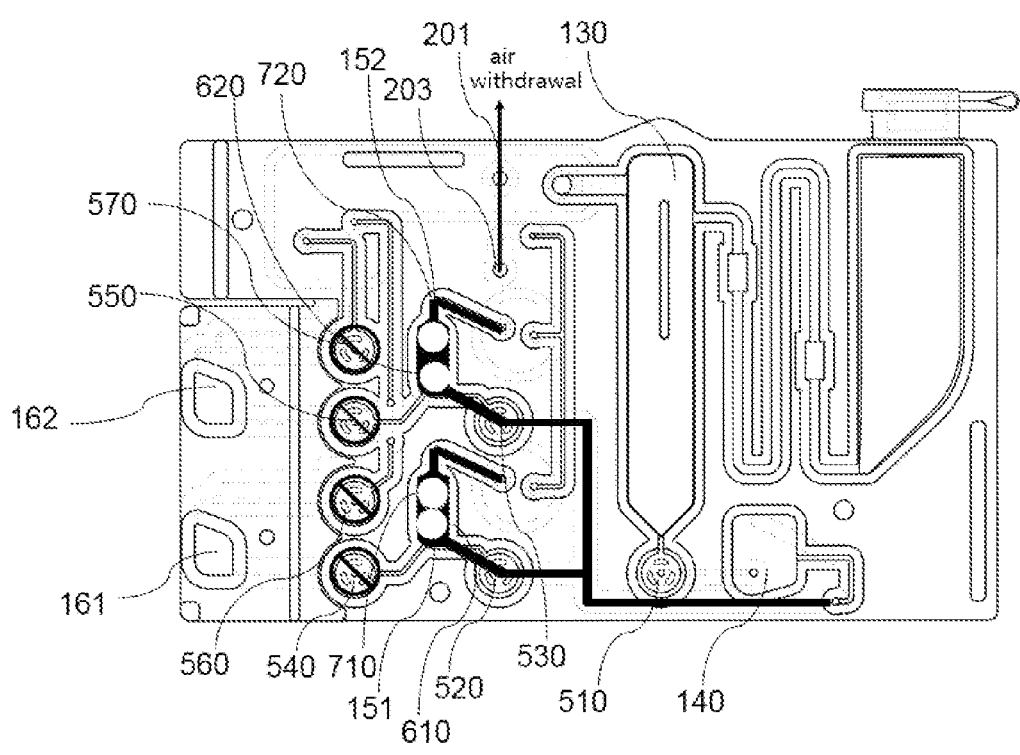
FIG. 25 is Schematic Diagram 10 of the working steps of the cartridge in Example 1 of the present invention.
Figure 26:
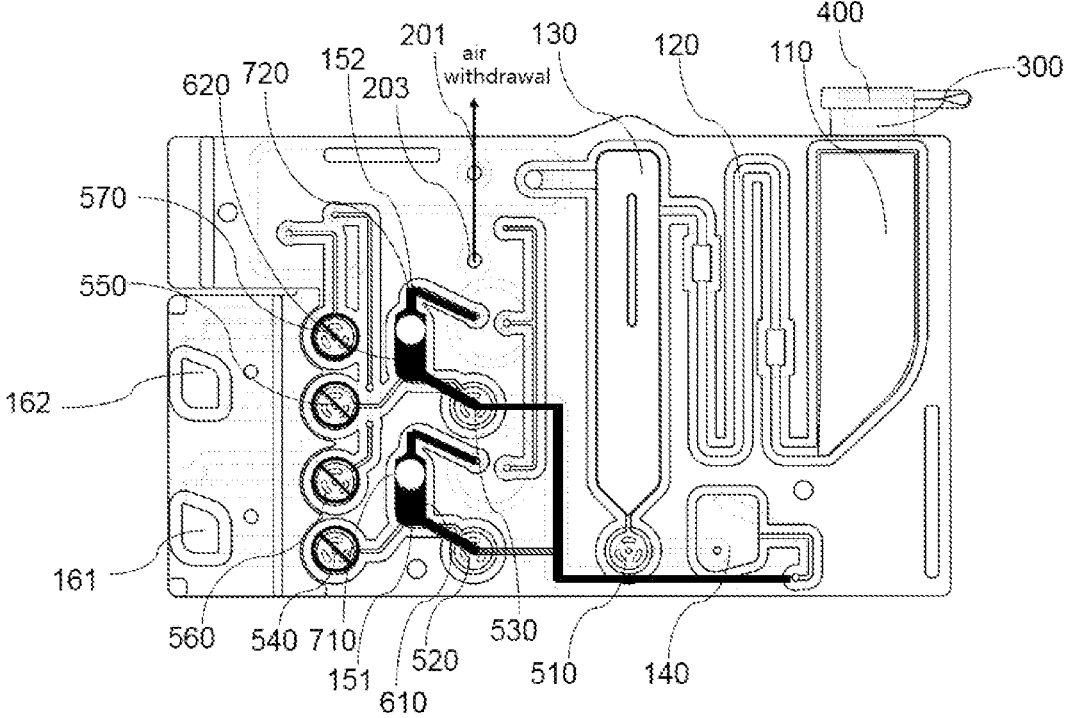
FIG. 26 is Schematic Diagram 11 of the working steps of the cartridge in Example 1 of the present invention.

As shown in FIG. 21, the fourth step: start heating module 2200 of the testing device, heat the sample in sample lysis compartment 130, so that the sample is lysed;

As shown in FIGS. 22-26, the fifth step: release the center rods corresponding to first ejector valve 510, second ejector valve 520 and third ejector valve 530 of the testing device; so that first ejector valve 510, second ejector valve 520, and third ejector valve 530 are in an open state.

The second air pump driving the testing device extracts air into the cartridge through third air hole 203; third air hole 203 and fourth air hole 204 are communicated through second air channel 220; when extracting air through third air hole 203, it causes the air in the first sample mixing compartment 151 and second sample mixing compartment 152 to be pumped out through third air channel 230, second air compartment 920 and third air compartment 930, resulting in the air pressure in first sample mixing compartment 151 and second sample mixing compartment 152 being changed so that the lysed sample will flow through the first valve chamber to flow through first channel 2510 to sample filtration compartment 140, and then enter first sample mixing compartment 151 and second sample mixing chamber 1521 after being filtered through the filtration film.

The sample filling sequence into first sample mixing compartment 151 and second sample mixing compartment 152 is not regular, and they may be filled one by one or at the same time; when either of first sample mixing compartment 151 and the second sample mixing compartment 151 is filled first, since second air compartment 920 has second waterproof and breathable film 1520, and third air compartment 930 has third waterproof and breathable film 1530, so that the sample cannot continue to enter first sample mixing compartment 151 or second sample mixing compartment 152 that is fully-filled first under the action of second waterproof and breathable film 1520 or third waterproof and breathable film 1530, thus allowing the sample to enter the other sample mixing compartment until both sample mixing compartments are filled; at the same time, due to second waterproof and breathable film 1520 and third waterproof and breathable film 1530, the air in the upper layer of the sample is expelled, avoiding the formation of air bubbles in first sample mixing compartment 151 and second sample mixing compartment 152, which affects the detection of nucleic acid amplification reactions in the subsequent PCR compartments;

For example: when the sample fills first sample mixing compartment 151, after the sample continues to enter sixth air hole 206 and contacts second waterproof and breathable film 1520, second waterproof and breathable film 1520 will adsorb and block sixth air hole 206, making it impossible for the sample to continue to flow into first sample mixing chamber 1511, at this moment, the sample will continue to fill second sample mixing compartment 152. After second sample mixing compartment 152 is filled, the sample will continue to enter eighth air hole 208 and reach third waterproof and breathable film 1530, third waterproof and breathable film 1530 will adsorb and block eighth air hole 208, so that the sample cannot continue to flow into second sample mixing chamber 1521, thus the sample fills first sample mixing compartment 151 and second sample mixing compartment 152.

Figure 27:
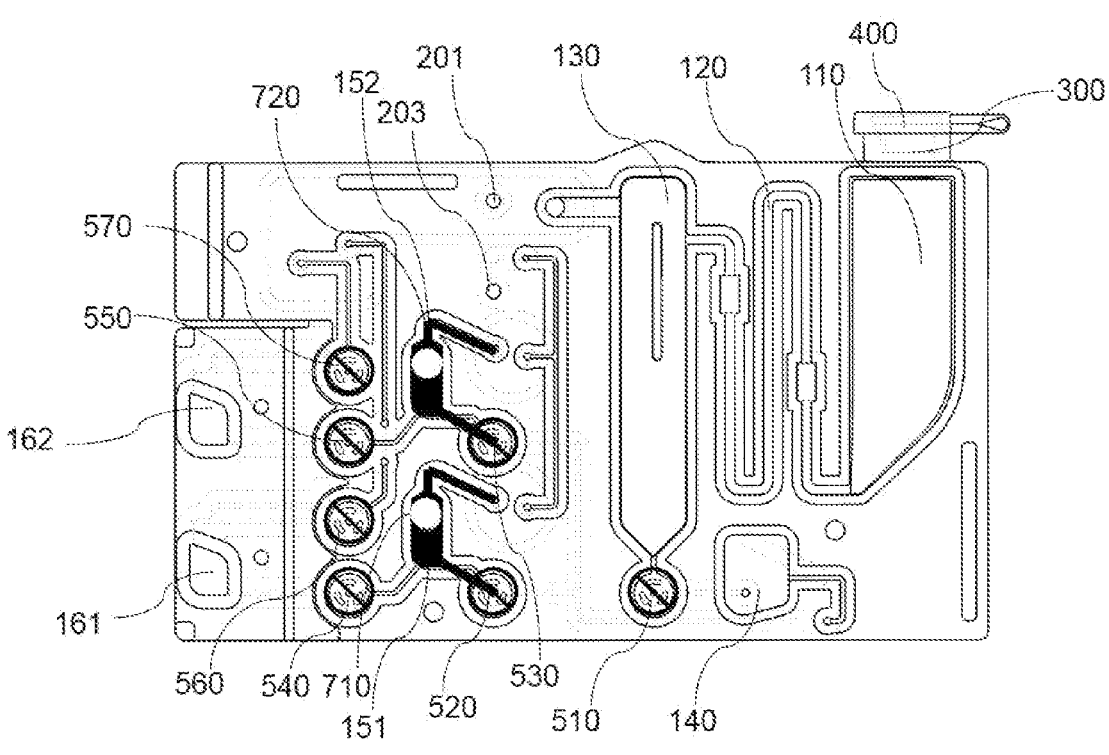
FIG. 27 is Schematic Diagram 12 of the working steps of the cartridge in Example 1 of the present invention.
Figure 28:
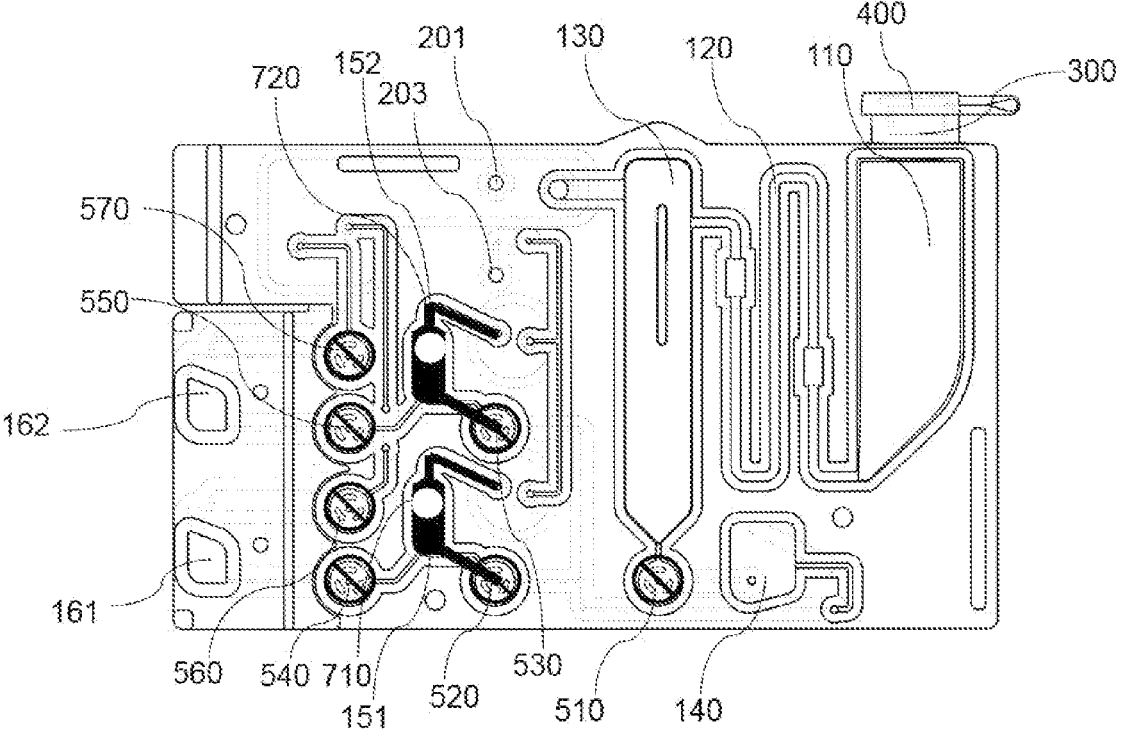
FIG. 28 is Schematic Diagram 13 of the working steps of the cartridge in Example 1 of the present invention.
Figure 29:
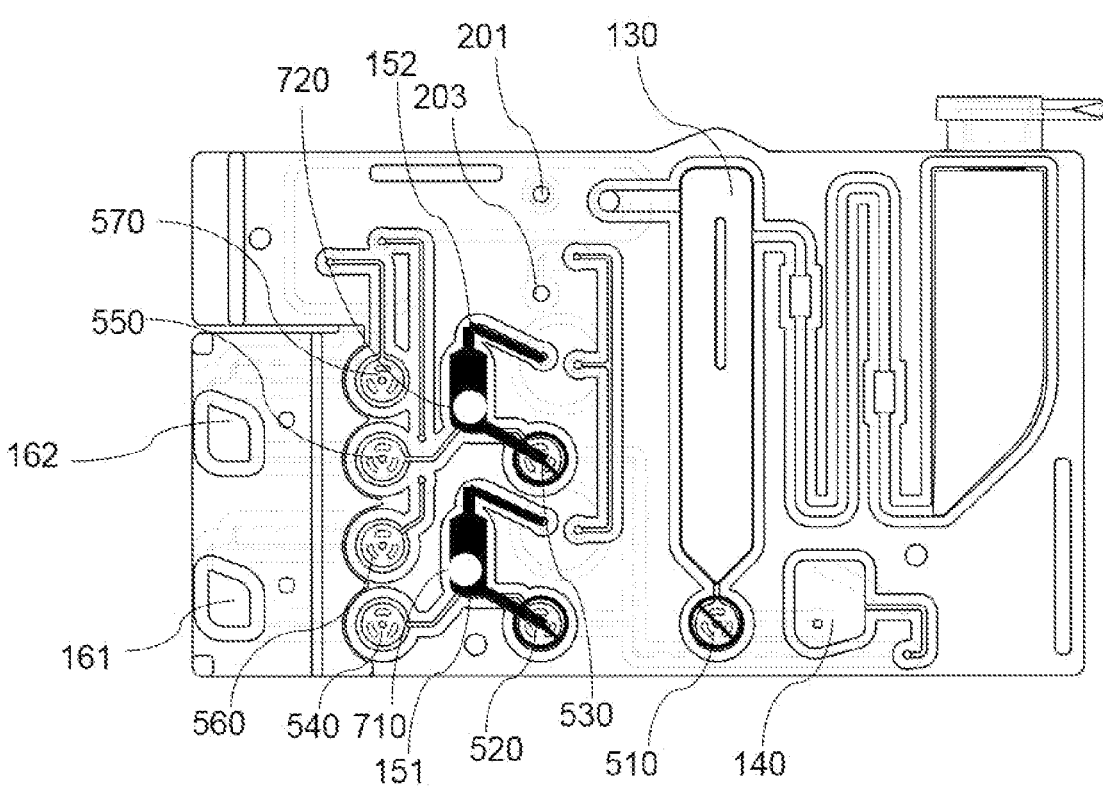
FIG. 29 is Schematic Diagram 14 of the working steps of the cartridge in Example 1 of the present invention.
Figure 30:
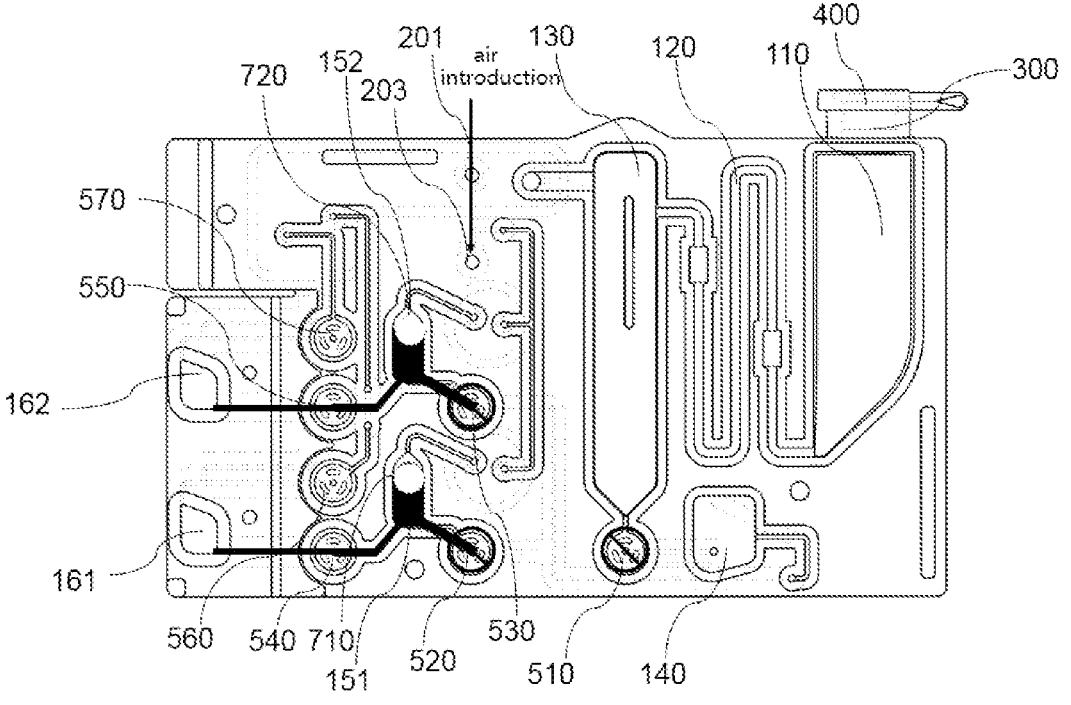
FIG. 30 is Schematic Diagram 15 of the working steps of the cartridge in Example 1 of the present invention.
Figure 31:
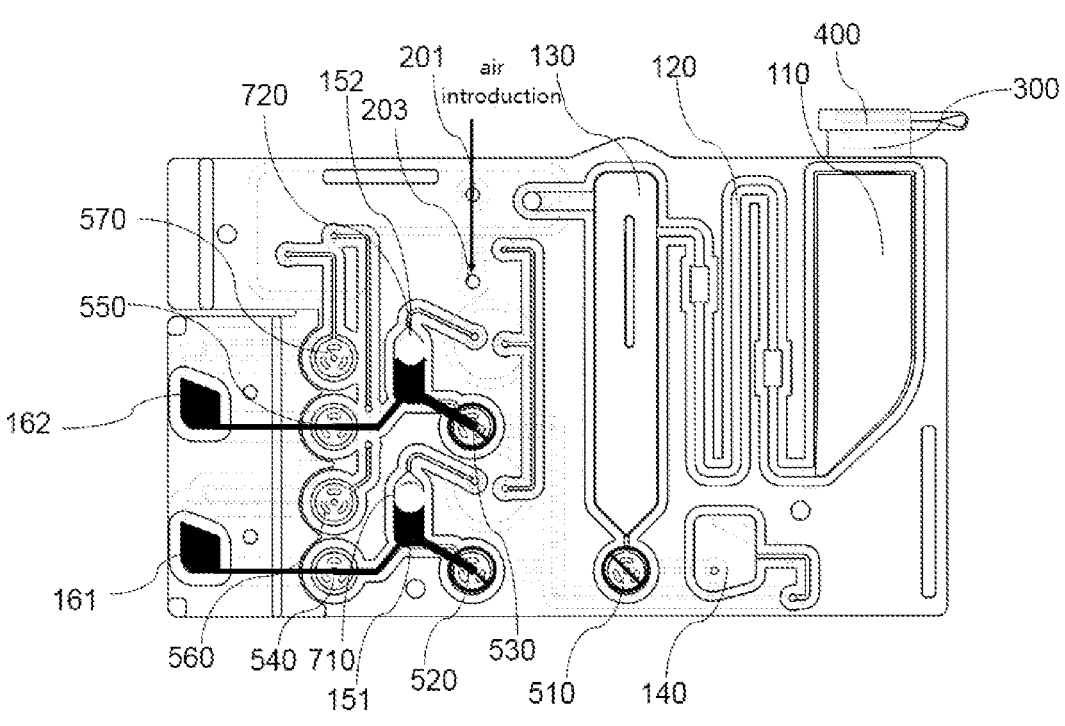
FIG. 31 is Schematic Diagram 16 of the working steps of the cartridge in Example 1 of the present invention.
Figure 32:
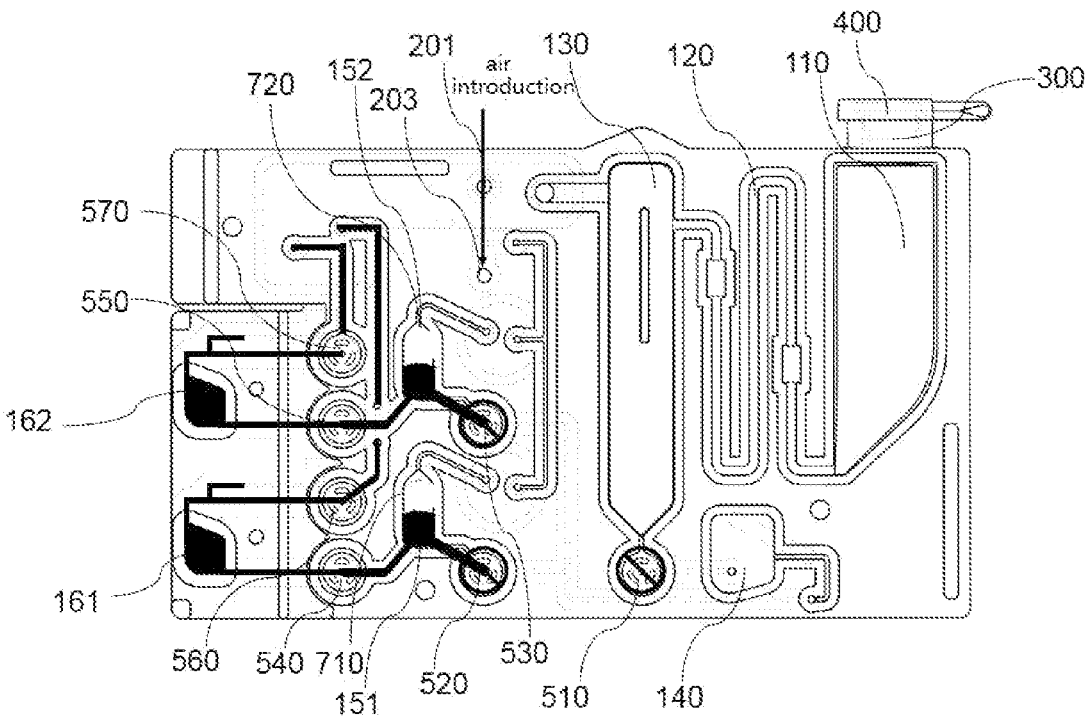
FIG. 32 is Schematic Diagram 17 of the working steps of the cartridge in Example 1 of the present invention.

As shown in FIGS. 27 and 28, the sixth step: after the sample flows into first sample mixing compartment 151 and second sample mixing compartment 152, it will be contacted with first lyophilized bead 610 and second lyophilized bead 620. First lyophilized bead 610 and second lyophilized bead 620 are rapidly redissolved;

Center rods corresponding to first ejector valve 510, second ejector valve 520, third ejector valve 530 are driven by the testing device to compress first ejector valve 510, second ejector valve 520, third ejector valve 530, so that first ejector valve 510, second ejector valve 520, and third ejector valve 530 are in a closed state; wherein, second ejector valve 520 is closed to prevent first mixing bead 710 in first sample mixing compartment 151 flow back into sample filtration compartment 140 during the mixing process of the samples with first lyophilized bead 610, thus avoiding the problem of reduced mixing of the sample in first sample mixing compartment 151 with the reagents of first lyophilized bead 610 due to some of the samples in first sample mixing compartment 151 flowing back into sample filtration compartment 140. Similarly, the third ejector valve is closed to avoid the problem of reduced effectiveness of mixing the sample in second sample mixing compartment 152 with the reagents of second lyophilized bead 620 due to some of the samples in the second sample mixing compartment 152 flowing back into the sample filtration compartment 140.

The electromagnet that drives first mixing bead 710 and second mixing bead 720 periodically moves first mixing bead 710 upward by generating a magnetic force to attract first mixing bead 710 and withdrawing the magnetic force to make first mixing bead 710 move downward due to its own gravity, cyclically controlling the electromagnet to make first mixing bead 710 move up and down in first sample mixing compartment 151, and first lyophilized bead 610 and the sample are mixed evenly, thus making the redissolved reagent in first lyophilized bead 610 is thoroughly mixed with the sample.

Similarly, second mixing bead 720 also performs the same up-and-down movement in second sample mixing compartment 152, and second lyophilized bead 620 is mixed with the sample evenly, thereby making the redissolved reagent in second lyophilized bead 620 is thoroughly mixed with the sample.

Figure 33:
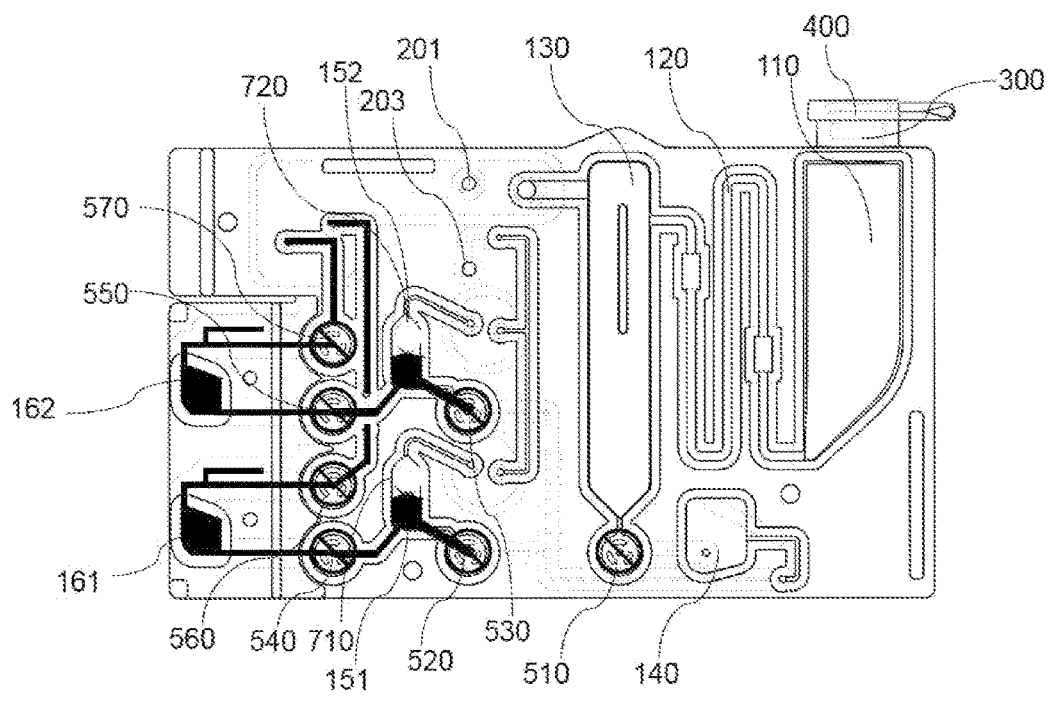
FIG. 33 is Schematic Diagram 18 of the working steps of the cartridge in Example 1 of the present invention.

As shown in FIGS. 29-32, the seventh step: center rods corresponding to fourth ejector valve 540, fifth ejector valve 550, sixth ejector valve 560 and seventh ejector valve 570 are driven by the testing device, so that fourth ejector valve 540, fifth ejector valve 550, sixth ejector valve 560 and seventh ejector valve 570 are in an open state;

Pushing air into the cartridge through third air hole 203 by the second air pump of the testing device will push the reacted sample in first sample mixing compartment 151 into first PCR compartment 161, and push the sample in second sample mixing compartment 152 into second PCR compartment 162;

Like the process of introducing first sample mixing compartment 151 and second sample mixing compartment 152 described above, the filling sequence of the first PCR compartment 161 and second PCR compartment 162 is not regular. When either of first PCR compartment 161 and second PCR compartment 162 is filled, the other PCR compartment will be filled immediately, or first PCR compartment 161 and second PCR compartment 162 may be filled at the same time. Since first air compartment 910 has the welded first waterproof and breathable film 1510, when the sample enters ninth air hole 209 through seventh channel 2570, first waterproof and breathable film 1510 will adsorb and block ninth air hole 209, so that the sample cannot continue to enter first PCR compartment 161, and the sample will continue to enter second PCR compartment 162. When the sample enters tenth air hole 2010 through the ninth channel 2590, first waterproof and breathable film 1510 will adsorb and block tenth air hole 2010, so that the sample cannot continue to enter second PCR compartment 162, thus both first PCR compartment 161 and second PCR compartment 162 are filled; meanwhile, first waterproof and breathable film 1510 permits discharge of air from the upper layer of the sample, thus preventing the formation of air bubbles in first PCR compartment 161 and second PCR compartment 162, which would interfere with the detection of the nucleic acid amplification reaction;

As shown in FIG. 33, the eighth step: release center rods of the testing device corresponding to fourth ejector valve 540, fifth ejector valve 550, sixth ejector valve 560 and seventh ejector valve 570, so that fourth ejector valve 540, fifth ejector valve 550, sixth ejector valve 560 and seventh ejector valve 570 are in a closed state;

First PCR compartment 161 and second PCR compartment 162 are respectively subjected to a cycle of heating and cooling by the testing device, and the amplification result is detected by the optical detection module to obtain the detection result.

The cartridge of the present embodiment has the following advantages:

(1) The cartridge of the present embodiment realizes the process of integration of sample lysis, nucleic acid amplification and detection, and realizes the process of automation from the sample adding to the detection result obtaining, and minimizes the process of human contact, reduces the probability of infection of the testing operators; it is more convenient and faster in which people without professional training can easily use, and reduces the requirements for the testing operators and the testing result has high reliability and accuracy.

(2) In the cartridge of the present embodiment, first sealing film 1200, second sealing film 1400 and third sealing film 1300 provide a fully enclosed and contamination-free seal for the cartridge, thereby ensuring the safety of the cartridge, and its simple operation eliminates the need to carry out the test in a specialized PCR laboratory, which reduces the requirements for the testing environment and avoiding the problem of virus leakage of samples caused by improper operation which may lead to infection of testing operators.

(3) In the cartridge of the present embodiment, by first mixing bead 710 moving up and down in first sample mixing compartment 151 to accelerate the nucleic acid amplification reaction, the samples and nucleic acid detection reagents can be sufficiently mixed to ensure the consistency of detection.

(4) The cartridge of the present embodiment only adopts the thermal lysis method to process the sample, and omits the complicated nucleic acid extraction steps, which can effectively shorten the total duration of nucleic acid detection, so that the total duration of nucleic acid detection is less than one hour, high-sensitivity detection of multiple targets in one sample can be completed simultaneously in even 45 minutes.

(5) In the prior art, nucleic acids are extracted from a sample and amplified. In this process, the sample is rinsed repeatedly, which may easily lead to the loss of nucleic acid: in each rinse round, about 10% to 20% of the nucleic acids are lost. Nucleic acid amplification assay is performed after rinsing, and the loss of nucleic acids may lead to inaccurate testing results. The cartridge of the present embodiment, which uses thermal lysis method to process samples, is suitable for analyzing relatively clean sample types such as nasopharyngeal swabs and cervical/vaginal swabs, and does not require rinsing in the nucleic acid amplification process, thus avoiding the loss of nucleic acid brought by the rinsing process.

(6) The cartridge of the present embodiment can complete sample adding outside the testing device, therefore is convenient and easy, and thus convenient for preservation and transportation in normal temperature conditions, without the need for a cold chain.

(7) In the cartridge of the present embodiment, lid 400 cannot be opened again after being closed, which avoids the virus leakage of the sample and causes the problem of infection to the testing operators.

(8) In the cartridge of this embodiment, only first sample mixing compartment 151 and second sample mixing compartment 152 are provided with reagents, and the reagents are all lyophilized components i.e. first lyophilized bead 610 and second lyophilized bead 620, which are free of liquid reagents, thus can be stored at room temperature for a long time, so that the cartridge of this embodiment can be stored at room temperature.

(9) The sample flow within this embodiment's cartridge is controlled by an air pump that can drive the sample flow. The dimensions of each compartment/chamber can be utilized to quantify the sample. This lowers the requirement for driving the air pump and improves testing consistency.

(10) In the cartridge of the present embodiment, the thickness of cartridge body 100 is greater than or equal to 1 mm, wherein the thickness of step portion 170 is less than 1 mm, and the thickness of other areas is 2 mm, which can be beneficial for the thermal exchange speed in the thermal cycle process; meanwhile, if there is air overflow during the PCR sample reaction, the air will go to the top of the PCR chamber due to gravity, and will not affect the optical detection.

(11) In the cartridge of this embodiment, a filtration film is provided in sample filtration compartment 140 for filtering large particles in the sample. When the sample flows through sample filtration compartment 140, if there are air bubbles in the sample, the air bubbles will stay above the sample filtration chamber due to buoyancy and will not flow into the next compartment/chamber, while the rest of the samples will flow into the next chamber, keeping the large particles and air bubbles in the sample stay in sample filtration compartment 140, thereby effectively preventing the large particles and air bubbles in the sample from blocking the flow channels and compartments/chambers, especially first PCR compartment 161 and second PCR compartment 162.

(12) Compared with existing testing kits, the cartridge of the present embodiment has a simpler structure and better testing quality. The simple structure is easier to produce and effectively reduces cost.

(13) In the cartridge of the present embodiment, the sample flows in one direction; that is, the sample sequentially flows from sample addition compartment 110, sample lysis compartment 130, sample filtration compartment 140, first sample mixing compartment 151 to first PCR compartment 161, This design prevents the sample from flowing back and forth in the channel, which may lead to the increased detection errors.

In the cartridge of another embodiment, it comprises cartridge body 100, first lyophilized bead 610, first mixing bead 710, first sealing film 1200, the first rubber cushion and fourth rubber cushion 542;

Cartridge body 100 is provided with lid 400, cassette sample addition nozzle 300, sample lysis chamber 132, a first valve chamber, first flow channel 251, first sample mixing chamber 1511, fourth flow channel 254, fourth valve chambers 541 and first PCR chamber 1611;

Wherein, sample lysis chamber 132, the first valve chamber, first flow channel 251, first sample mixing chamber 1511, fourth flow channel 254, fourth valve chamber 541 and first PCR chamber 1611 are all disposed on the first surface of cartridge body 100;

Lid 400 is disposed at the cassette sample addition nozzle, as described in the above-mentioned embodiment;

The first rubber cushion and the first valve chamber form first ejector valve 510, and fourth rubber cushion 542 and fourth valve chamber 541 form fourth ejector valve 540, as described in the above-mentioned embodiment;

The cassette sample addition nozzle is disposed on sample lysis chamber 132, the bottom of sample lysis chamber 132 communicates with the first valve chamber, the first flow channel hole communicates with first flow channel 251, and first flow channel 251 communicates with first sample mixing chamber 1511, third air hole 203 communicates with the first air passage of first sample mixing chamber 1511, third air hole 203 is used to communicate with the first air pump of the testing device, and first sample mixing chamber 1511 communicates with fourth valve chamber 541, and the fourth flow channel hole communicates with first PCR chamber 1611 through fourth flow channel 254;

First sealing film 1200 is welded on the first surface of cartridge body 100;

Sample lysis chamber 132 and first sealing film 1200 form first sample lysis compartment 130, first flow channel 251 and first sealing film 1200 form first channel 2510; first sample mixing chamber 1511 and first sealing film 1200 form first sample mixing compartment 151; fourth flow channel 254 and first sealing film 1200 form fourth channel 2540; first PCR chamber 1611 and first sealing film 1200 form first PCR compartment 161; first air path and first sealing film 1200 form first air passage 1512, the upper part of first PCR compartment 161 is provided with a waterproof and breathable film, so that the air above the sample pushed into first PCR compartment 161 can penetrate through the waterproof and breathable film, avoiding the occurrence of air bubbles in first PCR compartment 161 that would prevent air from being removed. Certainly, it can also be achieved by communicating first PCR compartment 161 with the air chamber provided with the waterproof and breathable film as in Example 1, as long as it can it is possible to achieve a structure that allows the air in the first PCR compartment 161 to be discharged and the sample to enter the first PCR compartment 161.

First mixing bead 710 and first lyophilized bead 610 are both located in first sample mixing compartment 151.

The detailed working process is as follows:

The first step: insert the cartridge of the present embodiment into the testing device;

Drive center rods of the testing device corresponding to first ejector valve 510 and fourth ejector valve 540, so that first ejector valve 510 and fourth ejector valve 540 are in a closed state;

The second step: add the sample into sample lysis compartment 130 through the cassette sample addition nozzle 300, since first ejector valve 510 is in a closed state, the sample will stay in sample lysis compartment 130;

The third step: drive the heating device of the testing device to heat sample lysis compartment 130, so that the sample in sample lysis compartment 130 is fully lysed;

The fourth step: release the center rods of the testing device corresponding to first ejector valve 510, so that first ejector valve 510 is in an open state;

Drive the second air pump of the testing device to withdraw air through third air hole 203, so that the air pressure in first sample mixing compartment 151 is reduced, and the lysed sample flows from sample lysis compartment 130 into first sample mixing compartment 151 through first flow channel 2510;

The fifth step: drive the center rod of the testing device corresponding to first ejector valve 510, so that first ejector valve 510 is in a closed state;

After the sample flows into first sample mixing compartment 151, it will come into contact with first lyophilized bead 610, and first lyophilized bead 610 is rapidly redissolved;

The electromagnet that drives first mixing bead 710 periodically moves first mixing bead 710 upward by generating a magnetic force to attract first mixing bead 710 and withdrawing the magnetic force to make first mixing bead 710 move downward due to its own gravity, cyclically controlling the electromagnet to make first mixing bead 710 move up and down in first sample mixing compartment 151, and first lyophilized bead 610 and the sample are mixed thoroughly to ensure high consistency in the subsequent nucleic acid amplification reaction.

The sixth step: release the center rod of the testing device corresponding to fourth ejector valve 540, so that fourth ejector valve 540 is in an open state;

Drive the second air pump of the testing device to inflate through third air hole 203, and the sample in first sample mixing compartment 151 is pushed into first PCR compartment 161 through fourth channel 2540;

First PCR compartment 161 is subjected to a cycle of heating and cooling by the testing device, and the amplification result is detected by the optical detection module to obtain the detection result.

The cartridge of the present embodiment has the following advantages:

(1) For the cartridge of the present embodiment, the cartridge is inserted into the testing device, thus realizing automatic and integrated amplification and detection of nucleic acid, which reduces the requirements for the testing operators, it is more convenient and faster in which people without professional training can easily use, and reduces the requirements for the testing operators and the testing result has high reliability and accuracy.

(2) In the cartridge of the present embodiment, first sealing film 1200 completely seals the cartridge, thereby ensuring the safety of the cartridge, and its operation is simple, avoiding the virus leakage from the sample caused by improper operation, which may lead to infection of testing operators.

(3) In the cartridge of this embodiment, by first mixing bead 710 moving up and down in first sample mixing compartment 151, so that the sample and the nucleic acid detection reagent can be fully mixed, ensuring the consistency of detection.

(4) The cartridge of the present embodiment only adopts the thermal lysis method to process the sample, and omits the complicated nucleic acid extraction step to accelerate the nucleic acid amplification reaction, which can effectively shorten the total duration of nucleic acid detection, so that the total duration of nucleic acid detection is less than one hour, high-sensitivity detection of multiple targets in one sample can be completed simultaneously in even 45 minutes.

(5) In the prior art, nucleic acids are extracted from a sample and amplified. In this process, the sample is rinsed repeatedly, which may easily lead to the loss of nucleic acid: in each rinse round, about 10% to 20% of the nucleic acids are lost. Nucleic acid amplification assay is performed after rinsing, and the loss of nucleic acids may lead to inaccurate testing results. The cartridge of the present embodiment, which uses thermal lysis method to process samples, is suitable for analyzing relatively clean sample types such as nasopharyngeal swabs and cervical/vaginal swabs, and does not require rinsing in the nucleic acid amplification process, thus avoiding the loss of nucleic acid brought by the rinsing process.

Compared with the cartridge in Example 1, the cartridge of the present example simplifies the following aspects in Example 1:

(1) The cartridge in the present embodiment directly communicates the cassette sample addition nozzle into sample lysis compartment 130, in order to directly add samples to sample lysis compartment 130, and sample addition compartment 110 and siphon tube 120 are omitted, thus reducing the waste of samples and the time required for nucleic acid detection, and the manufacturing cost of the cartridge is also reduced;

When first ejector valve 510 of the present embodiment is other types of valves that can be directly controlled, such as a solenoid valve, a choke valve, a locking valve similar to a faucet and a valve that is opened by rotating to align with the flow channel, it is also possible to directly adjust the first valve corresponding to sample lysis compartment 130 to a closed state, so that the sample added into sample lysis compartment 130 does not flow into first flow channel 251, and adding sample outside the testing device can be also realized.

(2) For some cartridges which are relatively clean and with relatively high flow channel, no sample filtration is needed, thus the efficiency of this cartridge in performing nucleic acid detection can be effectively saved.

(3) Second sample mixing compartment 152; for this embodiment, second sample mixing compartment 152 is not used, which can effectively improve the working efficiency of the cartridge, without waiting for the first sample mixing compartment and second sample mixing compartment 152 being filled before driving the corresponding first mixing bead 710 and second mixing bead 720 to perform their function. In this embodiment, only first sample mixing compartment 151 is used, after first sample mixing compartment 151 is filled, first mixing bead 710 can be driven to perform mixing and shaking, thus reducing the time for the sample to fill second sample mixing compartment 152 and the working efficiency of the cartridge can be improved.

(4) Second PCR compartment 162; since second sample mixing compartment corresponds to second PCR compartment 162, the time for filling second PCR compartment 162 with fewer samples can also be reduced, thereby the working efficiency of the cartridge can be improved.

Those skilled in the art can clearly understand that, for the convenience and simplicity of description, each above-described technical feature in the cartridge, some undescribed features and the corresponding effects of the above-described features, such as the material selection for the first rubber cushion and first sealing film 1200, etc., can be referred to the corresponding descriptions in Example 1, thus will not be repeated herein.

In some embodiments, sample addition compartment 110, sample lysis compartment 130, sample filter chamber 140, first sample mixing compartment 151, second sample mixing compartment 152, first PCR compartment 161, second PCR compartment 162 and the corresponding communication channels, air passages and air compartments, except for the structures in Example 1 and other embodiments, chambers can also be opened on cartridge body 100 as in Example 1, and the corresponding film can be used for sealing. For example, sample lysis chamber 132 is sealed by welding the corresponding sample lysis compartment 132 sealing film above it to form sample lysis compartment 130; first sample mixing compartment 151 is sealed by welding the corresponding first sample mixing compartment 151 sealing film above it to form first sample mixing compartment 151, etc.;

Alternatively, sample addition compartment 110, sample lysis compartment 130, sample filtration compartment 140, first sample mixing compartment 151, second sample mixing compartment 152, first PCR compartment 161 and second PCR compartment 162 can be formed by combining to lid or cover that has a sealing function corresponding to sample addition chamber 111, sample lysis chamber 132, sample filtration chamber 141, first sample mixing chamber 1511, second sample mixing chamber 1521, first PCR chamber 1611 and second PCR chamber 1621;

Furthermore, sample addition compartment 110, sample lysis compartment 130, sample filtration compartment 140, first sample mixing compartment 151, second sample mixing compartment 152, first PCR compartment 161 and second PCR compartment 162 can also be directly arranged in cartridge body 100, first PCR compartment 161 and second PCR compartment 162 are provided with windows for detection by the optical device;

Those skilled in the art can clearly understand that sample addition compartment 110, sample lysis compartment 130, sample filtration compartment 140, first sample mixing compartment 151, second sample mixing compartment 152, first PCR compartment 161, second PCR compartment 162 can be formed in various ways, sample addition compartment 110, sample lysis compartment 130, sample filtration compartment 140, first sample mixing compartment 151, second sample mixing compartment 152, first PCR compartment 161 and second PCR compartment 162 in Example 1 and other embodiments can be more easily observed through first sealing film 1200, second sealing film 1400 and third sealing film 1300, and will not be repeated herein.

Channels, air channels and air compartments in Example 1 and other embodiments can also be arranged inside cartridge body 100, or can be formed as the above-described ways of forming sample addition compartment 110, sample lysis compartment 130, sample filtration compartment 140, first sample mixing compartment 151, second sample mixing compartment 152, first PCR compartment 161 and second PCR compartment 162, which can be clearly understood by those skilled in the art, thus will not be repeated herein.

Wherein, as in Example 1 and other embodiments, first ejector valve 510, second ejector valve 520, third ejector valve 530, fourth ejector valve 540, fifth ejector valve 550, sixth ejector valve 560 and seventh ejector valve 570 can have various structures, and their functions can be also realized by other valves that can be opened and closed thus can be directly replaced thereby. Thus, first ejector valve 510 only needs to be the first valve that can be opened and closed, second ejector valve 520 only needs to be the second valve that can be opened and closed, and third ejector valve 530 only needs to be the third valve that can be opened and closed, and fourth ejector valve 540 only needs to be the fourth valve that can be opened and closed, fifth ejector valve 550 only needs to be the fifth valve that can be opened and closed, sixth ejector valve 560 only needs to be the sixth valve that can be opened and closed, and seventh ejector valve 570 only needs to be the seventh valve that can be opened and closed, which can be clearly understood by those skilled in the art, thus will not be repeated herein.

Wherein in Example 1, first air hole 201 communicates with the first air pump corresponding to the testing device, third air hole 203 communicates with the second air pump of the testing device, the sample is driven by the mode of deflating or inflating air to flow between compartments/chambers and in channels; in other embodiments, only third air hole 203 is used to drive the sample to flow between compartments/chambers and in channels, and the first air pump can also be used to deflate or inflate through first air hole 201 to control the cartridge in other embodiments to realize the detection; first air hole 201 and/or third air hole 203 can be arranged at other positions, as long as they can push the sample from sample lysis compartment 130 to first PCR compartment 161 and second PCR compartment 162, i.e., the cartridge can be driven by a pneumatic module, the pneumatic module comprises first air hole 201 connected with the air pump and/or a third air hole 203 connected with the air pump and ninth air hole 209 and the tenth air hole, so that the pneumatic module can drive the sample to flow between sample lysis compartment 130, first sample mixing compartment 151 and first PCR compartment 161; in addition, the pneumatic module may also comprise the above-mentioned first air hole 201, second air hole 202, third air hole 203, fourth air hole 204, fifth air hole 205, sixth air hole 206, seventh air hole 207, eighth air hole 208, ninth air hole 209 and the tenth air hole; by using the pneumatic module, the sample can be driven to flow between sample lysis compartment 130, first sample mixing compartment 151 and first PCR compartment 161, and in the above embodiment the sample can be driven to communicate between sample addition compartment 110, siphon tube, sample lysis compartment 130, sample filtration compartment 140, first sample mixing compartment, and first PCR compartment, and communicate between sample addition compartment 110, siphon tube, sample lysis compartment 130, sample filtration compartment 140, second sample mixing compartment 152, and second PCR filtration compartment 162; which can be clearly understood by those skilled in the art according to the above-mentioned working steps, thus will not be repeated herein.

Example 2

Figure 34:
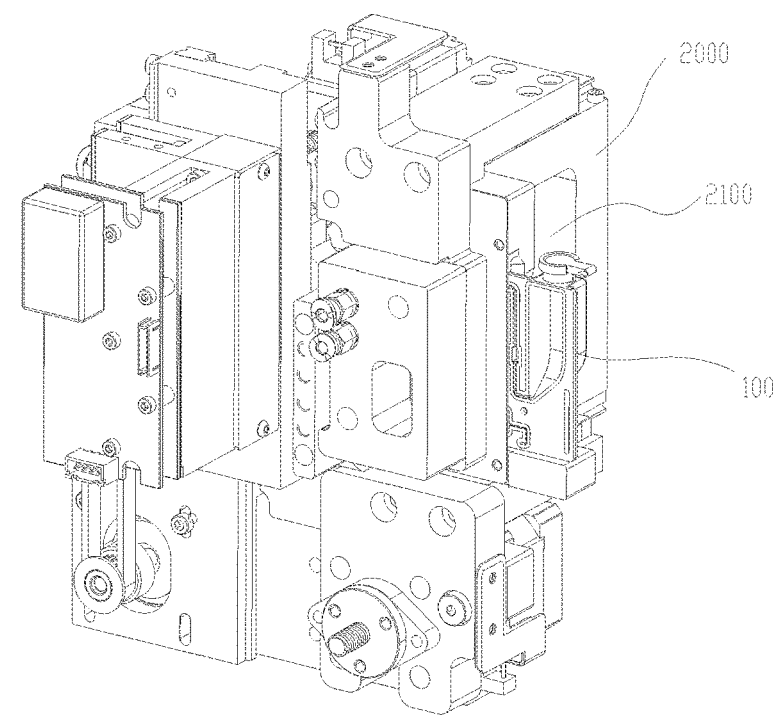
FIG. 34 is the front structure schematic diagram of the testing device in Example 2 of the present invention.
Figure 35:
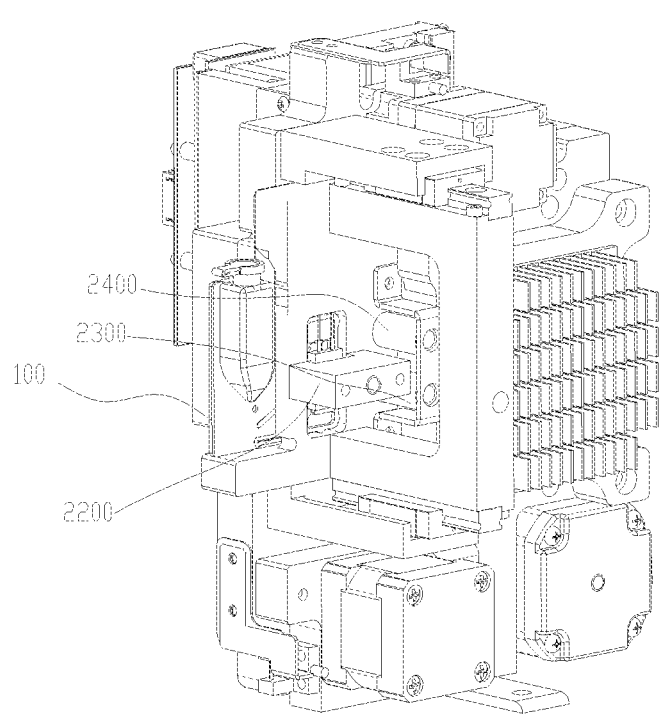
FIG. 35 is the back structure schematic diagram of the testing device in Example 2 of the present invention.
Figure 36:
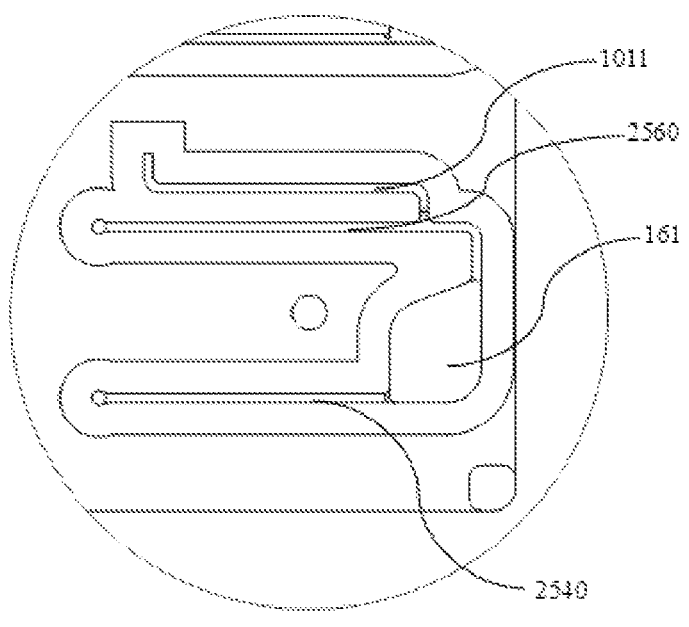
FIG. 36 is the structure schematic diagram of the PCR structure of the cartridge in the embodiment of the invention.
Figure 37:
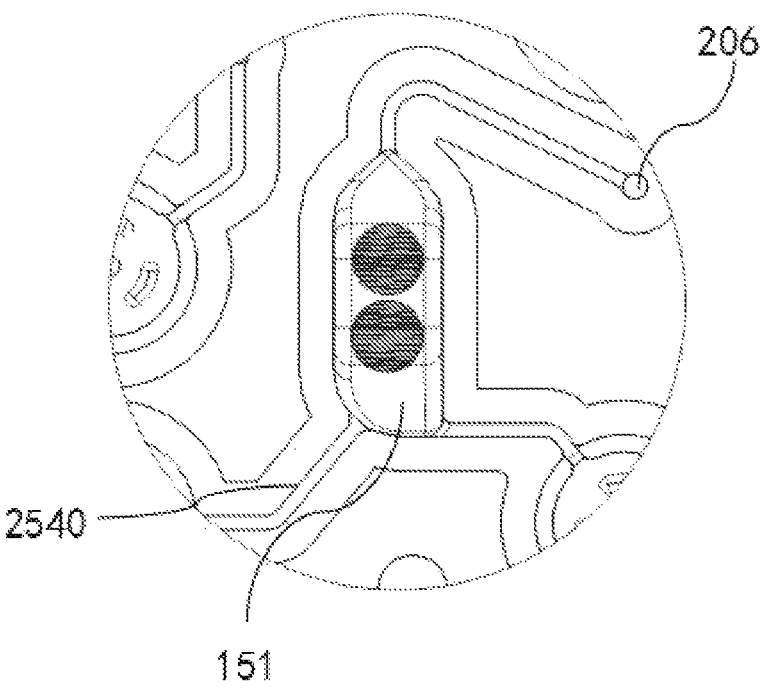
FIG. 37 is the structure schematic diagram of the mixing structure of the cartridge in the embodiment of the invention.
Figure 38:
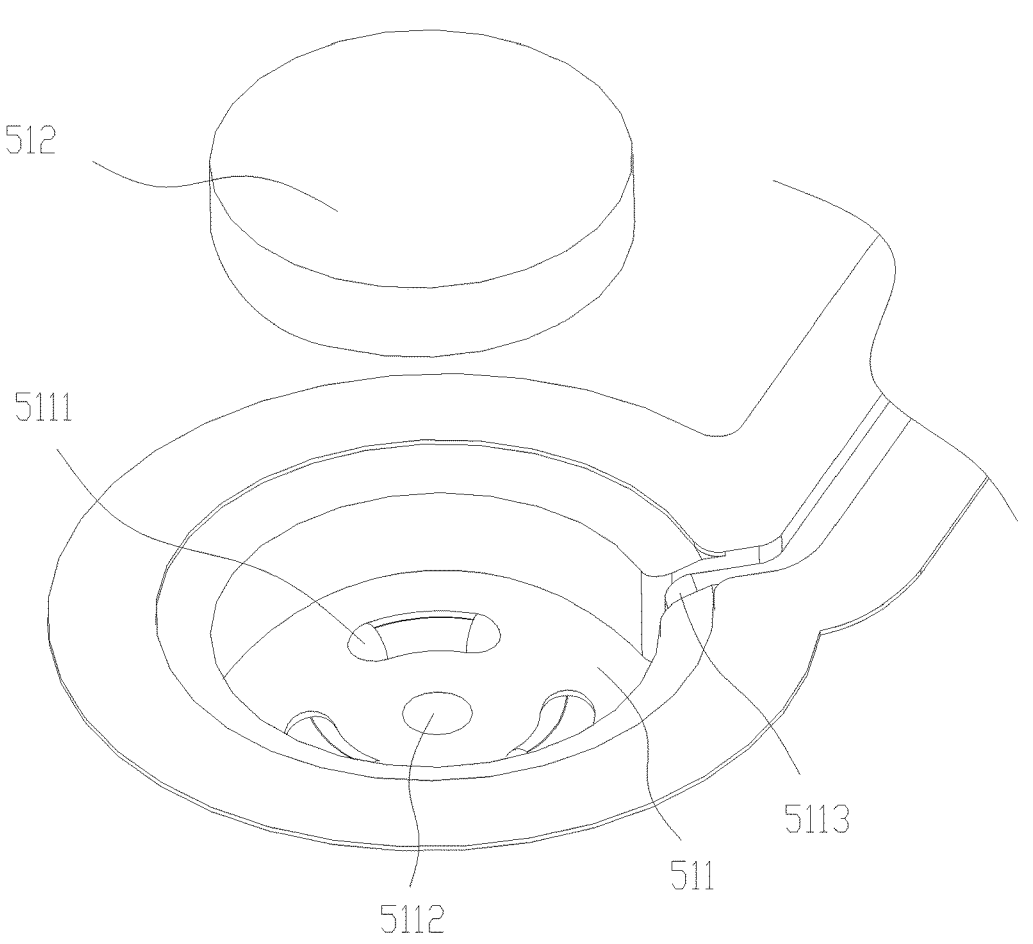
FIG. 38 is the exploded structure schematic diagram of the ejector valve structure in the embodiment of the invention.

Referring to FIG. 34, FIG. 34 is a schematic structure diagram of a testing device according to Example 2 of the present invention;

As shown in FIGS. 34 and 35, a testing device of another preferred embodiment of the present invention comprises the above-mentioned cartridge, and the supporting instruments used in cooperation with the cartridge;

The instruments mainly comprises: rack 2000 and the following disposed on rack 2000: the first air pump corresponding to first air hole 201, the second air pump corresponding to first air hole 201, the second air pump corresponding to third air hole 203, and the first center rod corresponding to first ejector valve 510, the second center rod corresponding to second ejector valve 520, the third center rod corresponding to third ejector valve 530, the fourth center rod corresponding to fourth ejector valve 540, and the fifth center rod corresponding to fifth ejector valve 550, the sixth center rod corresponding to sixth ejector valve 560, the seventh center rod corresponding to seventh ejector valve 570, and heating module 2200 disposed at the position corresponding to sample lysis compartment 130 for heating the sample lysis compartment 130 in which the sample is lysed, and first magnetic module 2300 disposed at the position corresponding to first sample mixing compartment 151, which is used to provide a magnetic attraction force and control the attraction or release of first mixing bead 710, and second magnetic module 2400 disposed at the position corresponding to second sample mixing compartment 152, which is used to provide a magnetic force to control the attraction or release of second mixing bead 720; the first temperature control module and the first optical detection module are provided at the position corresponding to first PCR chamber 1611, the second temperature control module and the second optical detection module are provided at the position corresponding to second PCR chamber 1621;

The first air pump and the second air pump can be realized by the remaining air pressure regulating devices.

When first ejector valve 510, second ejector valve 520, third ejector valve 530, fourth ejector valve 540, fifth ejector valve 550, sixth ejector valve 560 and seventh ejector valve 570 are replaced by other valves, in this embodiment, first ejector valve 510 is the first valve; second ejector valve 520 is the second valve; third ejector valve 530 is the third valve; fourth ejector valve 540 is the fourth valve; fifth ejector valve 550 is the fifth valve; sixth ejector valve 560 is the sixth valve; seventh ejector valve 570 is the seventh valve; the corresponding drive modules can preferably be used, i.e., the first drive module corresponding to the first valve, the second drive module corresponding to the second valve, the third drive module corresponding to the third valve, the fourth drive module corresponding to the fourth valve, the fifth drive module corresponding to the fifth valve, the sixth drive module corresponding to the sixth valve, and the seventh drive module valve corresponding the seventh valve.

Rack 2000 is provided with installation slot 2100, installation slot 2100 is disposed vertically, and the cartridge is vertically inserted into installation slot 2100. When the cartridge is disposed vertically, it can effectively avoid the generation of air bubbles in the process of flow between compartments/chambers, thus avoiding the interference of air bubbles, thereby effectively improving the accuracy of detection.

Wherein, heating module 2200 can be an electric heater, and can be heated for sample lysis compartment 130, so that the sample is lysed;

First magnetic module 2300 and second magnetic module 2400 may be electromagnets, which can drive first mixing bead 710 or second mixing bead 720 moving up and down, so that after the samples in first sample mixing compartment 151 thoroughly mixed with first lyophilized bead 610 and the samples in second sample mixing compartment 152 are thoroughly mixed with second lyophilized bead 620, nucleic acid amplification reactions occur in first PCR compartment 161 and second PCR compartment 162. By energizing and de-energizing the electromagnet to drive first mixing bead 710 or second mixing bead 720 to move up and down, it is simple to operate and can effectively enhance the mixing of the samples in first sample mixing compartment 151 and the second sample mixing compartment 152 with the reagents of the lyophilized bead to enable the results of the nucleic acid amplification reactions in first sample PCR compartment 151 and second PCR compartment 152 to maintain a high degree of consistency.

The working process of the testing device is as follows:

The first step: adding the sample into sample addition compartment 110 through cassette sample addition nozzle 300, then pressing lid 400, lid 400 covers cassette sample addition nozzle 300, and the cartridge is sealed by lid 400; it is to be ensured that lid 400 cannot be opened again after being pressed.

Due to the action of siphon tube 120, first choke valve 801 and the second choke valve between sample addition compartment 110 and sample lysis compartment 130, the sample will stay in siphon tube 120 and will not flow into sample lysis compartment 130 due to capillary action;

The second step: insert the cartridge vertically in installation slot 2100 of the testing device; the first air pump communicates with first air hole 201, and the second air pump communicates with third air hole 203;

Push the first center rod to compress first ejector valve 510, the second center rod to compress second ejector valve 520, the third center rod to compress third ejector valve 530, the fourth center rod to compress fourth ejector valve 540, the fifth center rod to compress fifth ejector valve 550, the sixth center rod to compress sixth ejector valve 560, and the seventh center rod to compress seventh ejector valve 570, so that first ejector valve 510, second ejector valve 520, third ejector valve 530, fourth ejector valve 540, fifth ejector valve 550, sixth ejector valve 560 and seventh ejector valve 570 are in a closed state, so that all channels in the cartridge are in a closed state.

The third step: drive the first air pump, draw the air in sample lysis compartment 130 through first air hole 201, first air hole 201 and second air hole 202 are communicated through first air compartment 910, therefore, the sample stayed in siphon tube 120 will be pumped into sample lysis compartment 130.

The fourth step: start heating module 2200 of the detection device, heat the sample in sample lysis compartment 130 to lyse the sample;

The fifth step: release the first center rod, the second center rod and the third center rod of the testing device so that first ejector valve 510, second ejector valve 520 and third ejector valve 530 are in an open state.

On the one hand, under the action of gravity, the sample will flow through the first valve chamber, then flow through first flow channel 2510 into sample filtration compartment 140;

On the other hand, the second air pump is driven to draw air into the cartridge through third air hole 203; third air hole 203 and fourth air hole 204 are communicated through second air channel 220; when the air is drawn from third air hole 203 and pass third air channel 230, second air compartment 920 and third air compartment 930, resulting in the air in first sample mixing compartment 151 and second sample mixing compartment 152 being evacuated, the air pressure of in first sample mixing compartment 151 and second sample mixing compartment 152 is changed, so that the lysed sample will be drawn into sample filtration compartment 140, and being filtered through the filtration film, and then enters into first sample mixing compartment 151 and second sample mixing compartment 152.

The sample filling sequence into first sample mixing compartment 151 and second sample mixing compartment

152 is not regular, and they may be filled one by one or at the same time; when either of first sample mixing compartment 151 and the second sample mixing compartment 151 is filled first, since second air compartment 920 has second waterproof and breathable film 1520, and third air compartment 930 has third waterproof and breathable film 1530, so that the sample cannot continue to enter first sample mixing compartment 151 or second sample mixing compartment 152 that is fully-filled first under the action of second waterproof and breathable film 1520 or third waterproof and breathable film 1530, thus allowing the sample to enter the other sample mixing compartment until both sample mixing compartments are filled; at the same time, due to second waterproof and breathable film 1520 and third waterproof and breathable film 1530, the air in the upper layer of the sample is discharged, avoiding the formation of air bubbles in first sample mixing compartment 151 and second sample mixing compartment 152, which affects the detection of nucleic acid amplification reactions in the subsequent PCR compartments;

For example: when the sample fills first sample mixing compartment 151, the sample continues to enter sixth air hole 206 and contacts second waterproof and breathable film 1520, second waterproof and breathable film 1520 will adsorb and block sixth air hole 206, making the sample cannot continue to flow into first sample mixing chamber 1511. At this time, the sample will continue to fill second sample mixing compartment 152. After second sample mixing compartment 152 is filled, the sample will continue to enter eighth air hole 208 and contact third waterproof and breathable film 1530, third waterproof and breathable film 1530 will adsorb and block eighth air hole 208, making the sample cannot continue to flow into second sample mixing chamber 1521, so that the sample fills first sample mixing compartment 151 and the second sample mixing compartment 152.

The sixth step: after the sample flows into first sample mixing compartment 151 and second sample mixing compartment 152, it will contact first lyophilized bead 610 and second lyophilized bead 620, and first lyophilized bead 610 and second lyophilized bead 620 are rapidly redissolved;

Drive the first center rod to compress first ejector valve 510, the second center rod to compress second ejector valve 520, the third center rod to compress third ejector valve 530, so that first ejector valve 510, second ejector valve 520 and third ejector valve 530 are in a closed state;

Drive first magnetic module 2300 and second magnetic module 2400, first magnetic module 2300 and second magnetic module 2400 are periodically energized and de-energized, and first mixing bead 710 move upward by generating a magnetic force by energizing and first mixing bead 710 move downward due to their own gravity by withdrawing a magnetic force by de-energizing, so that the electromagnet is cyclically controlled to make first mixing bead 710 move up and down in first sample mixing compartment 151, and first lyophilized bead 610 is evenly mixed with the sample, thus the redissolved reagent in first lyophilized bead 610 is completely mixed with the sample;

Similarly, second mixing bead 720 also performs the same up and down movement in second sample mixing compartment 152, and second lyophilized bead 620 is evenly mixed with the sample, thereby making the redissolved reagents in second lyophilized bead 620 thoroughly mixed with the sample.

The seventh step: release the fourth center rod, the fifth center rod, the sixth center rod and the seventh center rod, so that fourth ejector valve 540, fifth ejector valve 550, sixth ejector valve 560 and seventh ejector valve 570 are in an open state;

Push air into the cartridge through third air hole 203 by the second air pump, and the reacted sample in first sample mixing compartment 151 will be pushed into first PCR compartment 161, and the sample in second mixing chamber 1521 will be pushed into second PCR compartment 162;

Like the process of introducing first sample mixing compartment 151 and second sample mixing compartment 152 described above, the sequence in which the samples enter first PCR compartment 161 and second PCR compartment 162 is not regular. When either of first PCR compartment 161 and second PCR compartment 162 is filled, the other PCR compartment will be filled immediately, or first PCR compartment 161 and second PCR compartment 162 may be filled at the same time. Since first air compartment 910 has the welded first waterproof and breathable film 1510, when the sample enters ninth air hole 209 through seventh channel 2570, first waterproof and breathable film 1510 will adsorb and block ninth air hole 209, so that the sample cannot continue to enter first PCR compartment 161, and the sample will continue to enter second PCR compartment 162. When the sample enters tenth air hole 2010 through the ninth channel 2590, first waterproof and breathable film 1510 will adsorb and block tenth air hole 2010, so that the sample cannot continue to enter second PCR compartment 162, thus both first PCR compartment 161 and second PCR compartment 162 are filled; meanwhile, first waterproof and breathable film 1510 permits discharge of air from the upper layer of the sample, thus preventing the formation of air bubbles in first PCR compartment 161 and second PCR compartment 162, which would interfere with the detection of the nucleic acid amplification reaction;

The eighth step: drive the fourth center rod, the fifth center rod, the sixth center rod and the seventh center rod, so that fourth ejector valve 540, fifth ejector valve 550, sixth ejector valve 560 and the seventh ejector valve 570 are in a closed state;

First PCR compartment 161 is heated and cooled by the first temperature control module, and second PCR compartment 162 is respectively heated and cooled by the second temperature control module, and the amplification result obtained in first PCR compartment 161 is detected by the first optical detection module; the amplification result obtained in second PCR compartment 162 is detected by the second optical detection module.

Wherein the testing device also comprises a controller and a display. The controller is host computer, and the controller is electrically connected with the first air pump, the second air pump, the first center rod, the second center rod, the third center rod, the fourth center rod, the fifth center rod, the sixth center rod, the seventh center rod, heating module 2200, first magnetic module 2300, second magnetic module 2400, the first temperature control module, the second temperature control module, the first optical detection module and the second optical detection module;

The controller is used to control the first air pump, the second air pump, the first center rod, the second center rod, the third center rod, the fourth center rod, the fifth center rod, the sixth center rod, the seventh center rod, heating module 2200, first magnetic module 2300, second magnetic module 2400, the first temperature control module, the second temperature control module, the first optical detection module and the second optical detection module to complete the above working process.

The display is electrically connected with the controller for displaying that the controller controls the first air pump, the second air pump, the first center rod, the second center rod, the third center rod, the fourth center rod, the fifth center rod, the six center rod, the seventh center rod, heating module 2200, first magnetic module 2300, second magnetic module 2400, the first temperature control module, the second temperature control module, the first optical detection module and the second optical detection module to complete the process of the above steps, and when any step has a malfunction, the problem in that step will be displayed and an alert message will be shown.

The testing device proposed in the present invention enables the automatic processing of nucleic acid amplification and detection, has more accurate detection results, and only a small number of manual operation steps are required, thus is simple, safe and convenient to operate. Using the testing device, the detection duration time is less than one hour, the manual operation is no more than 2 minutes, and it can be used to detect pathogen genome targets of various different human clinical samples with wide applicability. The storage and transportation of the device of the present application are at normal temperature conditions, without the need for cold chain, which is highly economical. The cartridge of the testing device of the present invention is fully closed during the detection process, and its detection results are identical to those of the conventional methods, and it can be operated without professional training, which is safe and convenient.

Wherein, the first air pump and the second air pump in the Examples 1 and 2 can also be implemented using one air pump to realize through two output ends;

In addition, the effect of the cartridge and the description of the relevant components can be directly obtained according to Example 1 and other embodiments, which can be clearly and distinctly understood by those skilled in the art, thus will not be repeated herein.

Based on the cartridge in above-mentioned Example 1 and Example 2, the cartridge comprises sample lysis compartment 130, first sample mixing compartment 151 and first PCR compartment 161;

A first valve is provided between the sample lysis compartment 130 and the first sample mixing compartment 151, and the first valve is used to control the flow or blocking of the sample between the sample lysis compartment 130 and the first sample mixing compartment 151;

A fourth valve is provided between the first PCR compartment 161 and the first sample mixing compartment 151, and the fourth valve is used to control the flow or blocking of the sample between the first sample mixing compartment 151 and the first PCR compartment 161;

The first sample mixing compartment 151 is provided with a first reagent, and the first sample mixing compartment 151 is used to mix the nucleic acid in the sample with the first reagent.

The cartridge can obtain the following technical effects:

(1) In the cartridge of the present embodiment, insert the cartridge into the testing device, and the simple operation of the testing device enables automated and integrated amplification detection of nucleic acid, reducing the number of manual operation steps and the probability of infection of the testing operator; meanwhile, it reduces the requirements for the testing operators, thus is more convenient and quick, and can be easily used by personnel without professional training, and the testing results are highly reliable and accurate.

(2) In the cartridge of the present embodiment, the up and down movement by the first mixing bead in the first sample mixing compartment accelerates the mixing of the sample and the nucleic acid detection reagent, thus improving the stability of subsequent nucleic acid amplification.

(3) The cartridge of the present embodiment does not need to perform complicated nucleic acid extraction, and can effectively shorten the total duration of nucleic acid testing, so that the total duration of nucleic acid testing is less than one hour or even 45 minutes for simultaneously complete the high-sensitivity detection of multiple targets in one sample.

Based on the communication situation between each air passage, each flow channel, and each chamber disposed on the cartridge body in above-mentioned Example 1 and Example 2, the communication situation between each compartment, each channel, and each air channel can be easily obtained.

Based on Example 1 and Example 2, a PCR compartment structure of a cartridge is also provided in the embodiment of the present application, and the PCR compartment structure comprises:

First PCR compartment 161;

First damping compartment 1011, communicated with first PCR compartment 161, is used to relieve the pressure in first PCR compartment 161 during heating and cooling; and A valve is used to close first PCR compartment 161 during heating and cooling.

Wherein, first PCR compartment 161 communicates with ninth air hole 209; ninth air hole 209 is provided with first waterproof and breathable film 1510, and first waterproof and breathable film 1510 is used for discharging the air in first PCR compartment 161 and preventing liquid from overflowing outside first waterproof and breathable film 1510.

In the process of the liquid to be detected entering first PCR compartment 161, the air in first PCR compartment 161 is discharged from ninth air hole 209, and when first PCR compartment 161 is filled with liquid, first waterproof and breathable film 1510 on ninth air hole 209 blocks the liquid and prevents the liquid from overflowing outside first waterproof and breathable film 1510, so as to avoid the problem of sample leakage.

Wherein, the PCR compartment structure comprises:

Sixth channel 2560, sixth channel 2560 communicates with ninth air hole 209 and first PCR compartment 161, and sixth channel 2560 communicates with first damping compartment 1011.

First damping compartment 1011 is a channel structure, one end of first damping compartment 1011 communicates with first PCR compartment 161, and the other end is closed, when first PCR compartment 161 is filled, a gap is reserved in first damping compartment 1011. Specifically, first damping compartment 1011 is a slot provided on the cartridge, which is sealed by welding a sealing film on the surface to form a sealed channel structure, or an internal channel that can be dug out of the cartridge as first damping compartment 1011, wherein the size of the gap is adjusted with the change of pressure, so that when the temperature of the first PCR compartment 161 is raised and lowered, the liquid can flow between first PCR compartment 161 and first damping compartment 1011, so as to adjust the pressure change caused by the temperature change.

Wherein, the second end of first damping compartment 1011 is higher than first PCR compartment 161.

Wherein, first damping compartment 1011 is arranged in parallel with sixth channel 2560; first damping compartment 1011 is located above first PCR compartment 161, and the end of first damping compartment 1011 is bent upward; setting the end of first damping compartment 1011 to be bent upward is more beneficial to balance the pressure in first PCR compartment 161, especially when the temperature changes sharply.

Wherein, the valve includes the fourth valve and the sixth valve; the PCR compartment structure also comprises fourth channel 2540 and seventh channel 2570, and the seventh channel 2570 communicates with ninth air hole 209; the fourth valve is disposed on the fourth channel 2540; the sixth valve can communicate with sixth channel 2560 and seventh channel 2570 in a switchable manner, so that sixth channel 2560 can communicate with ninth air hole 209 in a switchable manner.

Optionally, the valve is an ejector valve; the ejector valve comprises a valve chamber and a rubber cushion, and the bottom of the valve chamber is provided with a flow channel hole and several bulged parts, and the side of the valve chamber is provided with an opening;

The rubber cushion is placed above the bulged part, and the bulged part supports the rubber cushion, so that a gap for the sample to flow into is formed between the undeformed rubber cushion and the flow channel hole, and the rubber cushion is used to block the flow channel holes when deformed by compressing.

Further, the bulged parts comprise at least two, all the bulged parts are arranged around the flow channel holes, and the sample flows into the flow channel holes from the gaps between adjacent bulged parts.

In the PCR compartment structure of the cartridge of the present embodiment, first damping compartment 1011 communicates with the upper part of first PCR compartment 161; when the sample fills first PCR compartment 161, the sample can enter first damping compartment 1011, and when heating first PCR compartment 161, the thermally expanded liquid can flow into first damping compartment 1011, thereby avoiding the problem of excessive pressure in first PCR compartment 161, thereby effectively solving the problem that the burst of first PCR compartment 161 due to excessive pressure in first PCR compartment 161, resulting in liquid leakage, which in turn leads to detection failure and virus-containing samples entering the environment, causing the problem of infection of the testing operators.

The providing of first damping compartment 1011 also makes the selection of the valve more flexible and wider, which solves the problem that the pressure increases of first PCR compartment 161 due to the liquid flow when the valve is closed. Taking the preferred ejector valve in this embodiment as an example, the ejector valve has the advantages of simple structure and reliable fluid control effect, and can flexibly switch the flow channels on the opposite surface of the cartridge, thus simplifying the operation of the supporting instruments; however, when it is closed, the pressure of first PCR compartment 161 will be increased, and the providing of first damping compartment 1011 can solve this problem.

Based on Example 1 and Example 2, the embodiments of the present application also provide a mixing structure of the cartridge provided by the embodiment of the present application, and the mixing structure comprises first sample mixing compartment 151;

First sample mixing compartment 151 is provided with a liquid inlet and a liquid outlet;

First sample mixing compartment 151 is provided with a first reagent and a first mixing component, and the first mixing element mixes the sample and the first reagent by movement, thus the nucleic acid in the sample is fully mixed with the first reagent thoroughly.

The liquid is the mixture after the sample is thoroughly mixed with the first reagent.

Wherein, the first mixing element is a mixing bead, which is a mixing bead of iron bead or other alloy material, and can move up and down under the control of an external drive device (such as a magnet), and thus the first reagent and a sample can be fully mixed, with a high mixing efficiency, and the consistency of the results obtained in the PCR detection after mixing is also high. Thereby, it effectively solves the problem in the prior art of using vibration to mix the sample and reagents with each other, with low efficiency and unsatisfying mixing effect, resulting in comparably lower consistency of the results in the subsequent PCR detection.

Wherein, the liquid inlet is an opening provided on first sample mixing compartment 151, communicated with an external channel, and is used for the sample to enter first sample mixing compartment 151;

The liquid outlet is an opening provided on first sample mixing compartment 151, communicated with an external channel, and is used for the sample to flow out of the opening outside first sample mixing compartment 151;

Wherein, the mixing structure also comprises:

Sixth air hole 206, first sample mixing compartment 151 communicates with sixth air hole 206;

Sixth air hole 206 is provided with a second waterproof and breathable film 1520. When first sample mixing compartment 151 is filled, second waterproof and breathable film 1520 can prevent liquid from overflowing outside second waterproof and breathable film 1520.

Second waterproof and breathable film 1520 can discharge air from second waterproof and breathable film 1520 when the sample enters first sample mixing compartment 151, otherwise, under the action of air pressure, it is difficult for the liquid to enter first sample mixing compartment 151.

The mixing structure also comprises:

Third air hole 203, fifth air hole 205 and second air compartment 920;

Fifth air hole 205 and sixth air hole 206 are both located in second air compartment 920, and second air compartment 920 is provided with a sealing film, and the sealing film is located outside second waterproof and breathable film 1520;

Wherein fifth air hole 205 and sixth air hole 206 can realize air communication in second air compartment 920;

Third air hole 203 is used to communicate with the second air pump, and third air hole 203 communicates with fifth air hole 205 to draw or push the air in first sample mixing compartment 151.

Draw air through third air hole 203 by the second air pump, so that the air in first sample mixing compartment 151 passes through sixth air hole 206, second air compartment 920 and fifth air hole 205 from first sample mixing compartment 151 and drawn through third air hole 203, so that the sample can enter first sample mixing compartment 151 under pressure, and is mixed with the first reagent by the first mixing element.

Wherein, the first reagent is first lyophilized bead 610; the first mixing element is first mixing bead 710.

First lyophilized bead 610 comprise excipients, and the weight of the excipients accounts for 20%-60% of the total weight of first lyophilized bead 610.

In first sample mixing compartment 151, one first lyophilized bead 610 and one first mixing bead 710 are provided.

The main components of first lyophilized bead 610 and second lyophilized bead 620 not only comprise the essential ingredients for nucleic acid detections such as primers, probes, reverse transcriptase, hot-start enzymes, dNTPs, strengthening agent, surfactants, salts and preservatives, etc. At the same time, substances such as excipients and protective agents must also be included. Excipients are usually inert substances, including sucrose, glucose, trehalose, melezitose, dextran, and mannitol, etc. The dosage of the excipient should be appropriate, a small amount makes it difficult to form, and a large amount makes it difficult to re-dissolved. In the cartridge of this embodiment, since first lyophilized bead 610 and the first mixing element are stored in first sample mixing compartment 151 at the same time, the hardness of first lyophilized bead 610 needs to fulfill special requirements. If the amount of excipient is too small, it is easy to be broken by the impact of the first mixing element during transportation, which affects the performance of subsequent reagent tests. But excessive excipient will increase the redissolution time of first lyophilized bead 610 and the mixing time of the first mixing element. The weight of the excipients of first lyophilized bead 610 used in this embodiment accounts for 20%-60% of the total weight of first lyophilized bead 610, more preferably 30%-50%, so that first lyophilized bead 610 can be effectively prevented from being broken by the impact of the first mixing element during transportation, and at the same time, the time for redissolution of first lyophilized bead 610 and the time for first mixing element to be mixed will not be increased too much.

Based on Example 1 and Example 2, the embodiment of the present application also provides an air intercommunication structure, the air intercommunication structure comprises:

The second air slot;

The fifth air hole, the fifth air hole communicates with the second air slot, for connecting the air pressure regulating device;

The sixth air hole, the sixth air hole communicates with the second air slot, and the sixth air hole is provided with a waterproof and breathable film I, for communicating with the compartment/chamber with sample reaction;

The second air slot is provided with the second sealing film to form the second air compartment;

Wherein, the fifth air hole and the sixth air hole realize air intercommunication in the second air compartment.

The second sealing film can seal the second air slot, so that the air in the second air slot is not communicated with the outside atmosphere, thus air intercommunication can be formed between the fifth air hole and the sixth air hole; deflation or inflation is performed with the air pressure regulating device, so that the liquid in the cartridge can flow among the compartments/chambers.

Wherein, the compartment/chamber communicated by the sixth air hole is the first sample mixing compartment in the present embodiment, and in other embodiments, the same can also be the sample lysis compartment, the second sample mixing compartment, the first PCR compartment and the second PCR compartment;

The waterproof and breathable film I on the sixth air hole can effectively prevent the liquid from overflowing into the first air slot, and meanwhile, the second sealing film can further effectively prevent the liquid from overflowing outside the cartridge. In addition, the providing of the second sealing film can realize the air intercommunication between the fifth air hole and the sixth air hole.

Further, the waterproof and breathable film is welded on the second air slot around the sixth air hole. In order to facilitate the setting of the waterproof and breathable film and effectively prevent liquid from overflowing outside the second air slot, the waterproof and breathable film is welded on the second air slot by laser spot welding and is located around the sixth air hole.

Further, the fifth air hole is provided with waterproof and breathable film II. The purpose of the second waterproof and breathable film II is to further prevent liquid from penetrating into the waterproof and breathable film I from the sixth air hole into the fifth air hole.

Further, the waterproof and breathable film I and waterproof and breathable film II are the same second waterproof and breathable film. The second waterproof and breathable film is attached to the second air slot, and is located above the fifth air hole and the sixth air hole, and is welded on the surface of the fifth air hole and the sixth air hole by laser spot welding, which is convenient for processing and manufacturing, and also effectively ensure that no liquid escapes from the fifth air hole and the sixth air hole.

Further, the second waterproof and breathable film is covered on the second air slot, and is welded on the second air slot around the fifth air hole and the sixth air hole.

Further, the air intercommunication structure also comprises:

The cartridge body and the third air hole, the second air channel and the third air channel disposed on the cartridge body;

Wherein, one end of the third air hole communicates with the air pressure regulating device; one end of the second air channel communicates with the other end of the third air hole; one end of the third air channel communicates with the other end of the second air channel, the other end of the third air channel communicates with the fifth air hole;

Wherein, the one end of the third air hole that communicates with the air pressure regulating device is located on the same surface of the cartridge body with the third air channel, and the second air channel and the third air channel are located on different sides of the cartridge body.

Specifically, the cartridge body is provided with the second air passage and the third air passage, and the second air passage and the third air passage are respectively located on opposite surfaces, i.e., the second air passage is located on the second surface of the cartridge body, the third air passage is located on the first surface of the cartridge body.

The second air passage is welded with the second sealing film on its surface to seal and form the second air channel, and the third air passage is welded with the main sealing film or the first sealing film on its surface to form the third air channel.

The reasons for providing the second air passage and disposing the second air passage on the face opposite to the one end that communicates with the third air passage and the third air hole communicating with the air pressure regulating device are as follows:

1) when the air pump is directly connected to the third air passage, it cannot be effectively sealed, and the air-tightness requirement of the air pump cannot be guaranteed;

2) The periphery of the third air passage needs to be welded to achieve sealing, thus existing a laser welding line, which can produce a bulged feature with a height of 0.001-0.1 mm on the cartridge body, and the plane of the cartridge body connecting with the air pump needs good flatness to ensure the contacting airtightness. Therefore, if the air pump communicates with the third air passage, it cannot be sealed with the air pump, but by employing the second air passage, the sealing between the cartridge and the air pump can be accomplished.

The second air passage and the third air passage are communicated through the fourth air hole, since the second air passage and the third air passage are not located on the same side of the cartridge body, thus, the second air passage communicate with the third air passage through the fourth air hole, allowing air to flow between the second air passage and the third air passage through the fourth air hole.

The air pressure regulating device is an air pump or the like, and the second air channel is deflated or inflated, thereby changing the pressure in the second air compartment.

Further, the second air slot, the fifth air hole and the sixth air hole are all disposed on the cartridge body, the sealing film on the second air channel and the sealing film of the second air compartment are all the same second sealing film, wherein the second sealing film is attached to the second surface of the cartridge body, specifically the peripheral side of the second air passage and the second air slot is welded and sealed to form a second air channel and a second air compartment that are not in contact with the outside atmosphere, thereby avoiding the problem of liquid leakage with the sample.

The second air channel and the third air channel are disposed on different surfaces of the cartridge body, to facilitate the providing of the second air channel and the third air channel, meanwhile there is sufficient space to provide the air pressure adjustment device such as an air pump, etc.; in addition, the installation of the air pressure adjustment device will not affect the third air channel. If the air pressure adjustment device is directly installed on the third air channel, when inflating or deflating, directly acting on the third air channel will easily cause the third air channel to be crushed under the direct action of changes in air pressure, resulting in damage of the cartridge and thus cannot be used. Providing the second air channel as a transition can effectively avoid the direct effect on the third air channel when inflating or deflating air, which is easy to cause the third air channel to be crushed under the direct action of the change of air pressure, resulting in the problem that the cartridge is damaged and cannot be used.

The embodiment of the present invention also provides an ejector valve structure, including valve chamber 511, rubber cushion 512 and at least one bulged part 5111. Valve chamber 511 is provided with an opening 5113 on the side, and flow channel hole 5112 on the bottom. Rubber cushion 512 is located above flow channel hole 5112. Bulged part 5111 is provided on the surface of rubber cushion 512 facing valve chamber 511, and/or at a position corresponding to rubber cushion 512 on the surface of valve chamber 511, so that a gap between the undeformed rubber cushion 512 and flow channel hole 5112 can be formed for the sample to flow in, and rubber cushion 512 is used to occur deforming when being compressed and blocks flow channel hole 5112.

The principle of operation of the ejector valve structure proposed by the present application is: due to the existence of bulged part 5111, when rubber cushion 512 is not subject to external force (undeformed), referring to FIGS. 11 and 12, there is a gap between rubber cushion 512 and the flow channel hole 5112, and the liquid sample can flow into valve chamber 511 from the opening 5113, and then into flow channel hole 5112, so as to flow out of the ejector valve structure along the flow channel. When rubber cushion 512 is subjected to a predetermined pressure, a deformation will occur, referring to FIG. 13, rubber cushion 512 is deformed to block flow channel hole 5112, so that the liquid cannot flow into or out of flow channel hole 5112, i.e., it cannot pass through the ejector valve structure, thus the ejector valve structure can play the role of blocking the flow of liquid. Due to the elasticity of rubber cushion 512, when the external force is removed, rubber cushion 512 returns to its original state, and returns to a state where there is a gap between rubber cushion 512 and flow channel hole 5112, and the liquid can flow through the ejector valve structure again.

The ejector valve of the present invention has a simple structure and reliable fluid control ability. The ejector valve structure can be controlled by only pressing, effectively simplifying the operation of the supporting instruments.

In some embodiments of the present application, bulged part 5111 is preferably disposed on the surface of valve chamber 511 to facilitate the processing and manufacture of the ejector valve structure.

In some embodiments of the present application, referring to FIGS. 1-44, flow channel hole 5112 may be disposed at the center of valve chamber 511, so that the liquid flows in and out from the center of valve chamber 511.

In some embodiments of the present application, rubber cushion 512 is preferably a silicone cushion, and the shape of rubber cushion 512 matches the shape of valve chamber 511. The shape of valve chamber 511 is circular, and the shape of rubber cushion 512 is also circular. The diameter of rubber cushion 512 is slightly smaller than the diameter of valve chamber 511, which ensures that rubber cushion 512 has sufficient space for deformation and also ensures the aesthetics of the structure.

For the ejector valve proposed by this application, a set of preferred values is provided below as a reference: the height of valve chamber 511 is 1.2 mm, and the height of the bulged part 5111 is 0.2 mm, accounting for about 16.7% of the height of valve chamber 511. The thickness of rubber cushion 512 is 1 mm and its hardness is 40 A. Further, when the height of the bulged part 5111 increases, rubber cushion 512 with softer hardness can be selected; and when the height of the bulged part 5111 decreases, rubber cushion 512 with higher hardness can be selected. According to the above principles, a rough value range can be obtained: the rubber cushion 512 with a hardness in the range of 60 A-30 A is selected according to the height of the bulged part 5111 which is 5%-30% of the height of the valve chamber 511.

In the ejector valve structure proposed by the present invention, the number, shape and disposing position of the bulged part 5111 may have various forms, and some preferred embodiments are provided below.

Detailed Implementation Process 1 is as follows:

The ejector valve structure of the present embodiment is provided with three bulged parts 5111, and all bulged parts 5111 are disposed on the surface of valve chamber 511. The bulged parts 5111 are arc-shaped, and are arranged at equal intervals in a circle shape with the center of flow channel hole 5112 as the center. Here, the bulged parts 5111 are not arranged in a complete circle, and there is a gap between two adjacent bulged parts 5111, and the liquid sample can flow into flow channel hole 5112 from the gap. The above arrangement enables bulged part 5111 to better fit rubber cushion 512, to create a gap between rubber cushion 512 and flow channel hole 5112 when rubber cushion 512 is not compressed.

In this embodiment, opening 5113 is disposed at the upper side of valve chamber 511, and its corresponding lower part is inclined downward from the outside to the inside, so that the liquid flows into valve chamber 511.

Figure 39:
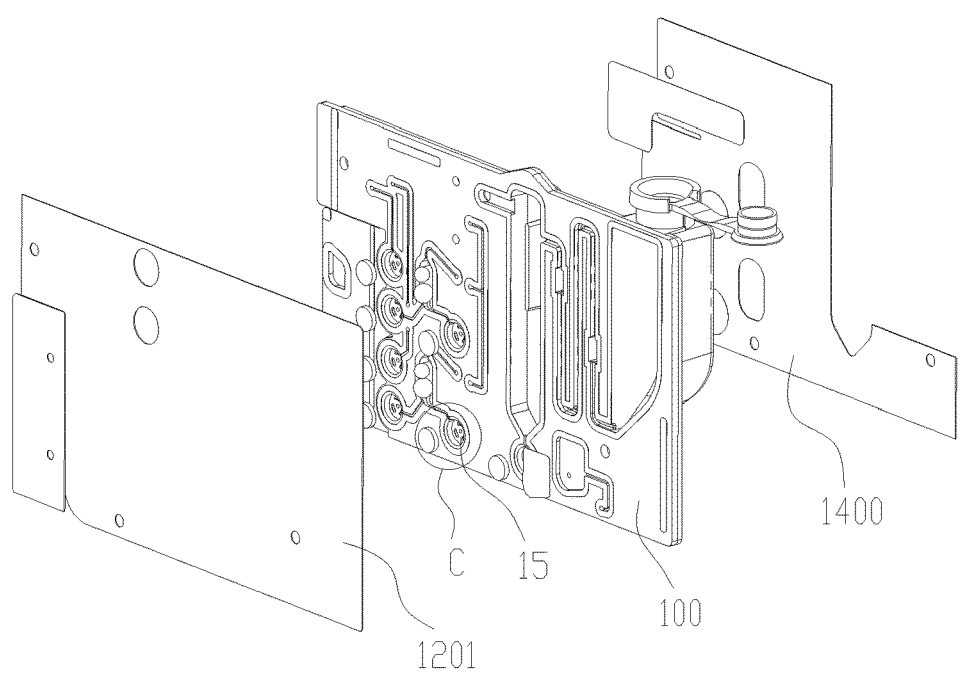
FIG. 39 is the exploded structure schematic diagram of the one-piece cartridge provided with the ejector valve structure of the embodiment.
Figure 40:
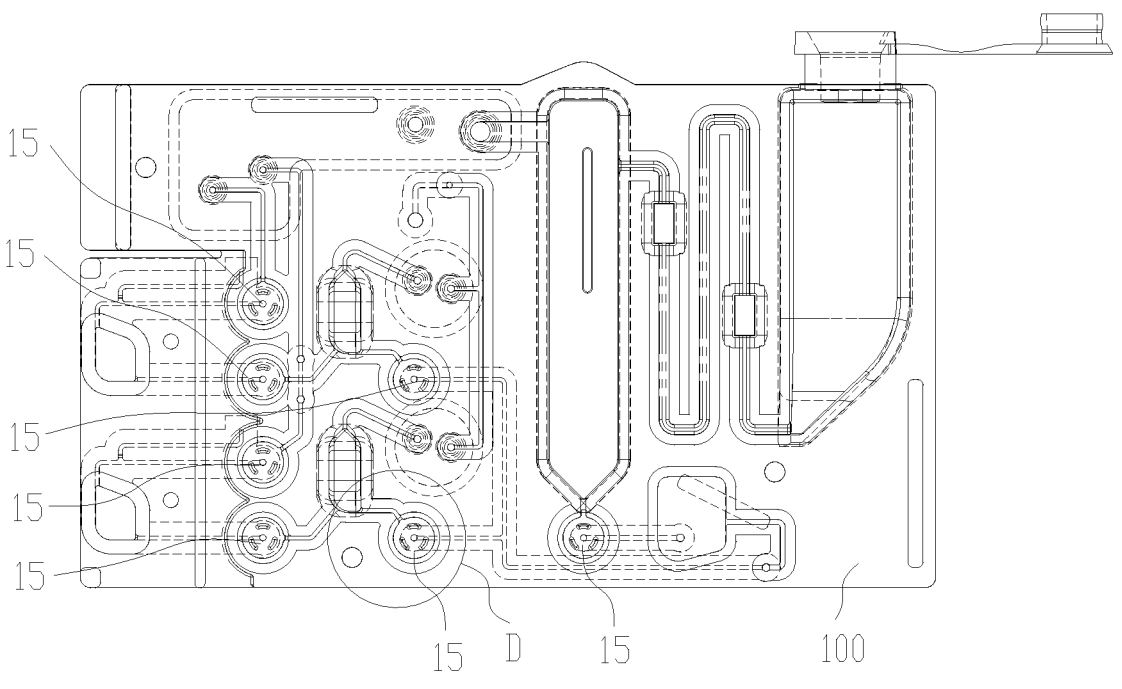
FIG. 40 is the front structure schematic diagram of the cartridge body in FIG. 39.
Figure 41:
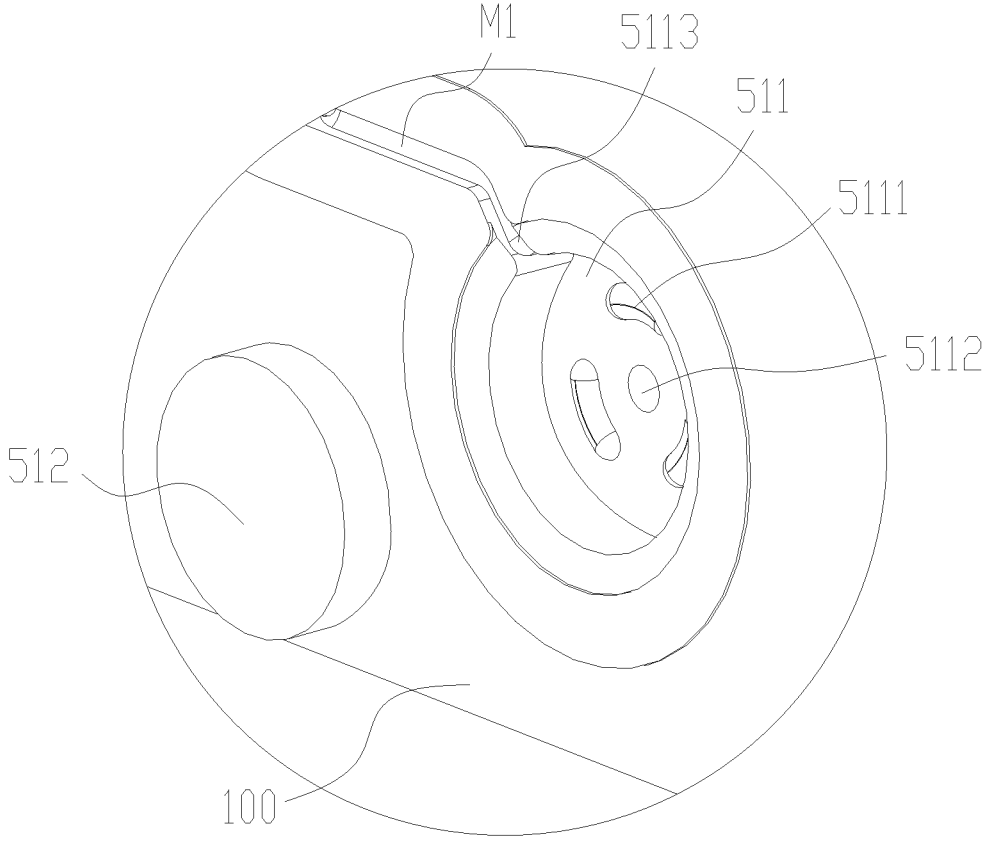
FIG. 41 is the enlarged view at C place in FIG. 39.
Figure 42:
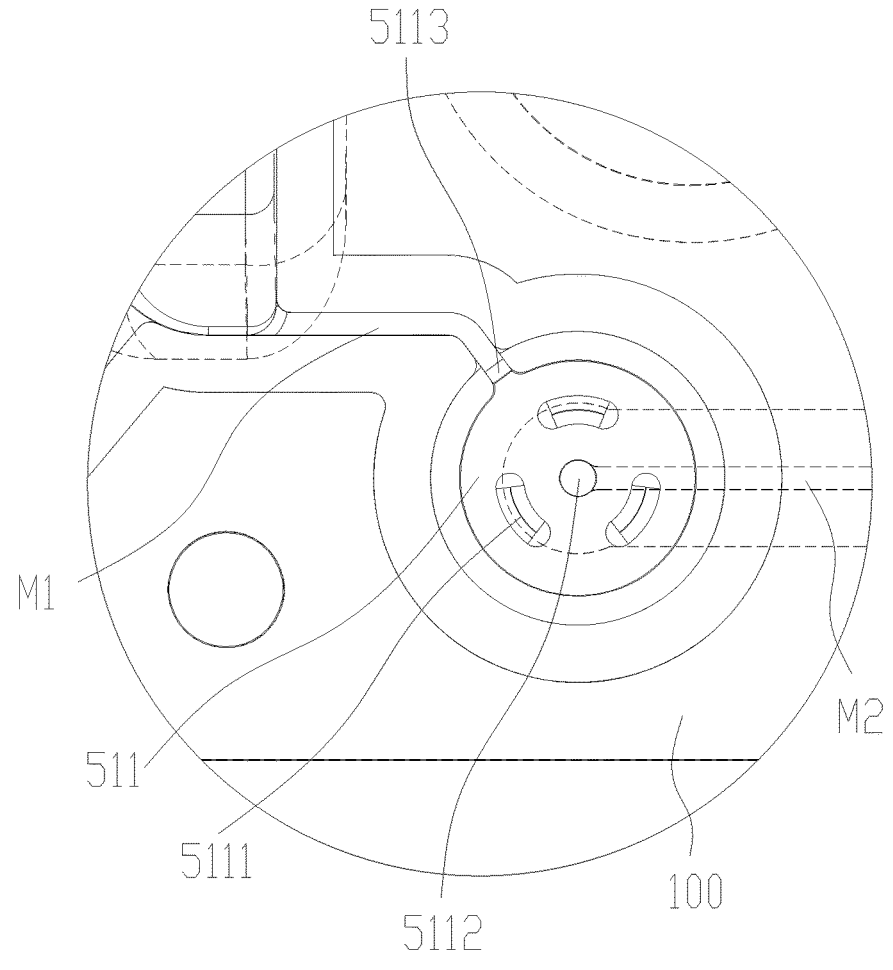
FIG. 42 is the enlarged view at D place in FIG. 7.

Referring to FIG. 39, a one-piece cartridge 10 provided with a plurality of ejector valve structures of the present embodiment for nucleic acid detection, one-piece cartridge 10 mainly comprises cartridge body 100, main sealing film 1201 and second sealing film 1400. The surface of cartridge body 11 is provided with a plurality of reaction chambers and a plurality of flow channels for communicating the reaction chambers. The ejector valve structure in this embodiment is denoted as ejector valve 15, which is disposed on the flow channel and is used to control the passage state of liquid. Referring to FIG. 40, the solid line in FIG. 40 represents front flow channel M1 provided on the front of cartridge body 11, and the dotted line represents back flow channel M2 provided on the back of cartridge body 11. Main sealing film 1201 and second sealing film 1400 are respectively attached to the front and back of cartridge body 11 to seal reaction chamber 14 and the flow channels. Referring to FIGS. 41-42, front flow channel M1 communicates with opening 5113, and back flow channel M2 communicates with flow channel hole 5112. Both opening 5113 and flow channel hole 5112 can allow the liquid to flow out or flow in, i.e., in ejector valve 15, the flow direction of the liquid is not limited. In the actual production of the cartridge, valve chamber 511, bulged part 5111, opening 5113 and flow channel hole 5112 of the ejector valve structure can be formed directly on the surface of cartridge body 11 by digging slots and holes, etc., and then a suitable rubber cushion 512 is configured according to the shape and size of valve chamber 511.

After the one-piece cassette 10 is assembled with the supporting instrument, a driving rod (not shown in the figure) is provided at the corresponding position of rubber cushion 512 of each ejector valve structure. When the driving rod moves forward, it presses rubber cushion 512, i.e., the ejector valve structure is closed, so that the liquid cannot pass through the ejector valve structure, thus realizing the blocking effect; when the driving rod moves backward, the pressure on rubber cushion 512 is removed, and rubber cushion 512 is restored to its original state, i.e., the ejector valve structure is opened, thus enabling liquid pass through the ejector valve structure, thereby achieving a flow-through effect. The above control method enables the ejector valve structure to achieve a fluid control effect.

Figure 43:
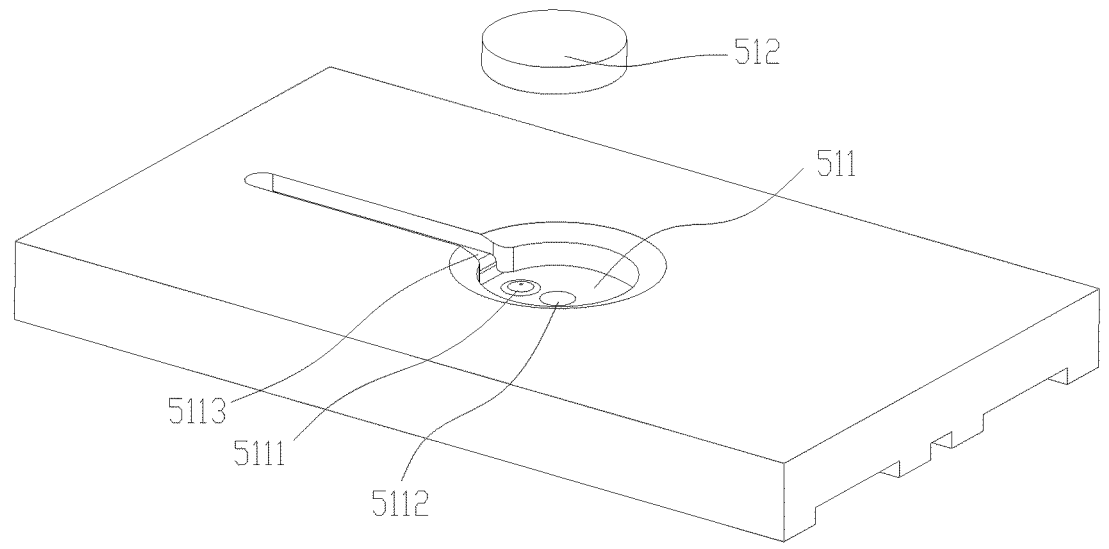
FIG. 43 is another exploded structure schematic diagram of the ejector valve structure in the embodiment of the present invention.
Figure 44:
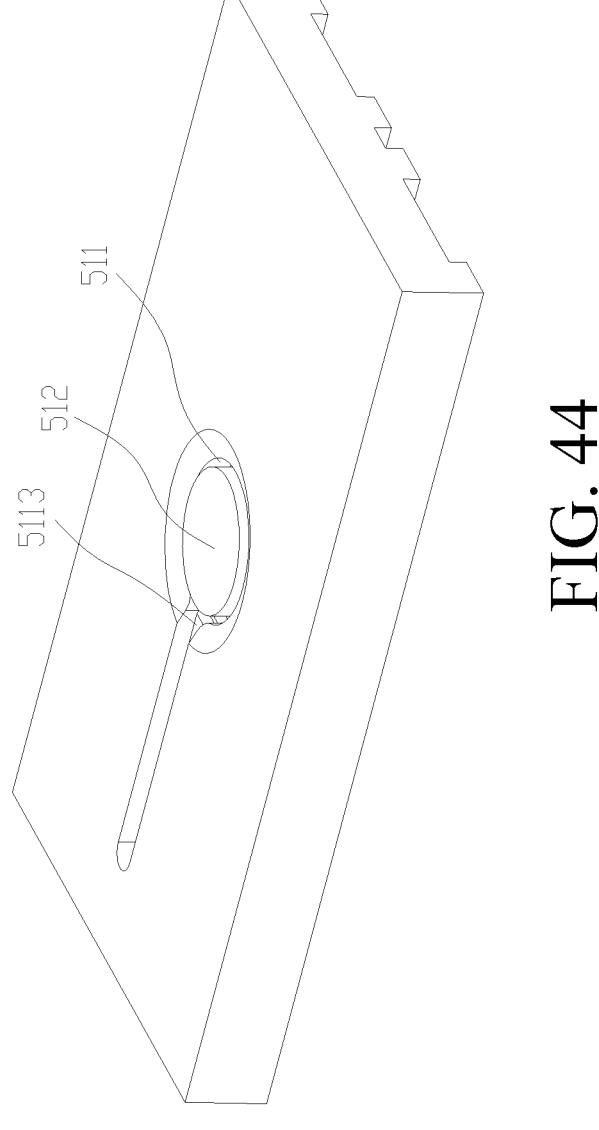
FIG. 44 is a schematic diagram of the axial side structure of the ejector valve structure of FIG. 43.

Detailed Implementation Process 2 is as follows:

Referring to FIGS. 43-44, the ejector valve structure of this embodiment is provided with only one bulged part 5111, and bulged part 5111 is provided on the surface of valve chamber 511.

In this embodiment, bulged part 5111 is provided on the connecting line between opening 5113 and flow channel hole 5112. When rubber cushion 512 is not compressed, the above arrangement makes the liquid flowing from opening 5113 into flow channel hole 5112 around the two sides of bulged part 5111, not only ensuring a gap can be formed between rubber cushion 512 and flow channel hole 5112, but also shortening the flow distance of the liquid from opening 5113 to flow channel hole 5112 as much as possible, thereby ensuring that the ejector needle valve structure is more reliable and more sensitive when performing liquid control.

In this embodiment, referring to FIGS. 43-44, the shape of bulged part 5111 is provided as an arcuate shape, so as to better fit rubber cushion 512 to form a gap between rubber cushion 512 and flow channel hole 5112.

In this embodiment, referring to FIGS. 43-44, opening 5113 is provided at the upper side of valve chamber 511, and its corresponding lower part is inclined downward from the outside to the inside, so that the liquid flows into valve chamber 511.

In the above-mentioned Implementation Process 1 and Implementation Process 2, the way of providing of the bulged part 5111 is a preferred solution, and does not constitute a limitation to the present application. According to the operation principle of the ejector valve structure proposed in the present application, it can be seen that in the ejector valve structure proposed in the present application, only one bulged part 5111 is needed to cooperate with rubber cushion 512 to realize the function of liquid control, and multiple bulged parts 5111 can also be provided. To cooperate to realize the function of liquid control.

In other embodiments, when there are more than two bulged parts 5111, the bulged parts 5111 can be arranged around the edge of flow channel hole 5112.

Further, bulged parts 5111 may be made to be provided in a circumferential array around the edges of flow channel hole 5112.

Further, bulged parts 5111 can be arranged at equal intervals.

All of the above-mentioned arrangements facilitate a better fit of bulged part 5111 with rubber cushion 512 to form a gap between rubber cushion 512 and flow channel hole 5112 when rubber cushion 512 is not compressed to ensure the flow-through effect.

In summary, in the ejector valve structure proposed by the present invention, opening 5113 is disposed on the side of valve chamber 511, flow channel hole 5112 is disposed at the bottom, and rubber cushion 512 is disposed above flow channel hole 5112, and is provided with bulged part 5111 for lifting rubber cushion 512. When no pressure is applied to rubber cushion 512, bulged part 5111 pushes up rubber cushion 512, so that a gap is formed between rubber cushion 512 and flow channel hole 5112, the liquid can pass through flow channel hole 5112, thus the ejector valve realizes the flow-through effect; when the pressure is applied to rubber cushion 512, rubber cushion 512 is deformed and blocks flow channel hole 5112, the liquid cannot pass through flow channel hole 5112, and the ejector valve achieves the flow blocking effect; when the pressure on rubber cushion 512 is withdrawn, rubber cushion 512 returns to its original state by its retractive force, and the ejector valve return to allow flow passing through, i.e., it can automatically return to its original state.

The ejector valve proposed by the present invention has a simple structure, and reliable fluid control effect, and the ejector valve structure can be controlled by just pressing, which effectively simplifies the operation of the supporting instruments.

The above is only the preferred embodiments of the present invention, it should be noted that some improvements and replacements can be made by those skilled in the art without departing from the technical principle of the present invention; these improvements and replacement should also be regarded as the protection scope of the present invention.

What is claimed is:

1. A cartridge comprising a sample lysis compartment (130), a first sample mixing compartment (151) and a first PCR compartment (161);

wherein a first valve is provided between the sample lysis compartment (130) and the first sample mixing compartment (151), and the first valve is configured to control the flow or blocking of a sample between the sample lysis compartment (130) and the first sample mixing compartment (151); a fourth valve is provided between the first PCR compartment (161) and the first sample mixing compartment (151), and the fourth valve is configured to control the flow or blocking of the sample between the first sample mixing compartment (151) and the first PCR compartment (161); and the first sample mixing compartment (151) is provided with a first reagent configured to mix with nucleic acids in the sample;

wherein the cartridge further comprises a pneumatic module, the pneumatic module is configured to drive sample flow between the sample lysis compartment (130), the first sample mixing compartment (151), and the first PCR compartment (161);

wherein the pneumatic module comprises a third air hole (203) and a ninth air hole (209), the third air hole (203) communicates with the first sample mixing compartment (151); the first PCR compartment (161) communicates with the ninth air hole (209); and a first waterproof and breathable film (1510) is provided on the ninth air hole (209), the first waterproof and breathable film (1510) is configured for discharging air from the first PCR compartment (161) while blocking liquid from flowing out of the first waterproof and breathable film (1510); and wherein the third air hole (203) communicates with a second air pump to draw or push air contained in the first sample mixing compartment (151).

2. The cartridge according to claim 1, further comprising a sample filtration compartment (140);

wherein the sample filtration compartment (140) communicates with the first sample mixing compartment (151); and the first valve is located between the sample lysis compartment (130) and the sample filtration compartment (140).

3. The cartridge according to claim 1, further comprising a first damping compartment (1011) communicating with the first PCR compartment (161).

4. The cartridge according to claim 1, further comprising a sample addition compartment (110) communicating with the sample lysis compartment (130).

5. The cartridge according to claim 1, wherein the first sample mixing compartment (151) is further provided with a first mixing bead (710), the first mixing bead (710) is configured to mix the sample and the first reagent thoroughly by its movement.

6. The cartridge according to claim 1, further comprising a cassette sample addition nozzle (300), wherein the cassette sample addition nozzle (300) communicates with the sample addition compartment (110), and is configured used for adding the sample into the sample addition compartment (110).

7. The cartridge according to claim 1, wherein a plate (131) is provided in the sample lysis compartment (130), the plate (131) is configured to prevent the sample from splashing when entering the sample lysis compartment (130) and configured to balance a force acting upon the cartridge.

8. The cartridge according to claim 1, wherein the first valve is disposed below the sample lysis compartment (130) and communicates with a bottom of the sample lysis compartment (130).

9. The cartridge according to claim 1, wherein the cartridge further comprises a sixth valve, the ninth air hole (209) communicates with the first PCR compartment (161) through the sixth valve in a switchable manner; and the pneumatic module further comprises a sixth air hole (206), the sixth air hole (206) communicates with the first sample mixing compartment (151), the sixth air hole (206) is provided with a second waterproof and breathable film (1520), when the first sample mixing compartment (151) is filled up, the second waterproof and breathable film (1520) is configured to prevent liquid from flowing out of the second waterproof and breathable film (1520).

10. The cartridge according to claim 1, wherein the pneumatic module further comprises a first air hole (201), and a first air channel (210) is provided at the cartridge;

said first air hole (201) communicates with the first air channel (210), the first air channel (210) communicates with the sample lysis compartment (130); and said first air hole (201) is configured to communicate with a first air pump to draw or push air contained in the sample lysis compartment (130).

11. The cartridge according to claim 9, further comprising a fifth air hole (205) and a second air compartment (920), wherein the fifth air hole (205) and the sixth air hole (206) are both located in the second air compartment (920), the second air compartment (920) is provided with a sealing film, and the sealing film is located on an outer side of the second waterproof and breathable film (1520); and wherein the fifth air hole (205) communicates with the third air hole (203), the fifth air hole (205) and the sixth air hole (206) exchange air in the second air compartment (920).

12. A testing device, comprising the cartridge according to claim 1 and a supporting instrument;

the supporting instrument comprises at least the following modules:

a first driving module configured for driving the opening and closing of the first valve;

a fourth driving module configured for driving the opening and closing of the fourth valve;

a first magnetic module (2300) configured for providing magnetic force;

a heating module (2200) configured for heating a sample mixture;

a first temperature control module configured for providing a heating and cooling cycle;

a first optical detection module configured for assessing amplification in a chamber.

13. The testing device according to claim 12, the device further comprises a rack (2000), the first driving module, the fourth driving module, the first magnetic module (2300), the heating module (2200), and the first temperature control module are all disposed on the rack (2000);

an installation slot (2100) is provided on the rack (2000) at a position corresponding to the positions of the first driving module, the fourth driving module, the first magnetic module (2300), the heating module (2200), and the first temperature control module; the cartridge is vertically inserted into the installation slot (2100).

14. A testing device, comprising the cartridge according to claim 2 and a supporting instrument;

the supporting instrument comprises at least the following modules:

a first driving module configured for driving the opening and closing of the first valve;

a fourth driving module configured for driving the opening and closing of the fourth valve;

a first magnetic module (2300) configured for providing magnetic force;

a heating module (2200) configured for heating a sample mixture;

a first temperature control module configured for providing a heating and cooling cycle;

a first optical detection module configured for assessing amplification in a chamber.

15. A testing device, comprising the cartridge according to claim 3 and a supporting instrument;

the supporting instrument comprises at least the following modules:

a first driving module configured for driving the opening and closing of the first valve;

a fourth driving module configured for driving the opening and closing of the fourth valve;

a first magnetic module (2300) configured for providing magnetic force;

a heating module (2200) configured for heating a sample mixture;

a first temperature control module configured for providing a heating and cooling cycle;

a first optical detection module configured for assessing amplification in a chamber.

16. A testing device, comprising the cartridge according to claim 4 and a supporting instrument;

the supporting instrument comprises at least the following modules:

a first driving module configured for driving the opening and closing of the first valve;

a fourth driving module configured for driving the opening and closing of the fourth valve;

a first magnetic module (2300) configured for providing magnetic force;

a heating module (2200) configured for heating a sample mixture;

a first temperature control module configured for providing a heating and cooling cycle;

a first optical detection module configured for assessing amplification in a chamber.

17. A testing device, comprising the cartridge according to claim 5 and a supporting instrument;

the supporting instrument comprises at least the following modules:

a first driving module configured for driving the opening and closing of the first valve;

a fourth driving module configured for driving the opening and closing of the fourth valve;

a first magnetic module (2300) configured for providing magnetic force;

a heating module (2200) configured for heating a sample mixture;

a first temperature control module configured for providing a heating and cooling cycle;

a first optical detection module configured for assessing amplification in a chamber.

18. A testing device, comprising the cartridge according to claim 6 and a supporting instrument;

the supporting instrument comprises at least the following modules:

a first driving module configured for driving the opening and closing of the first valve;

a fourth driving module configured for driving the opening and closing of the fourth valve;

a first magnetic module (2300) configured for providing magnetic force;

a heating module (2200) configured for heating a sample mixture;

a first temperature control module configured for providing a heating and cooling cycle;

a first optical detection module configured for assessing amplification in a chamber.

19. A testing device, comprising the cartridge according to claim 7 and a supporting instrument;

the supporting instrument comprises at least the following modules:

a first driving module configured for driving the opening and closing of the first valve;

a fourth driving module configured for driving the opening and closing of the fourth valve;

a first magnetic module (2300) configured for providing magnetic force;

a heating module (2200) configured for heating a sample mixture;

a first temperature control module configured for providing a heating and cooling cycle;

a first optical detection module configured for assessing amplification in a chamber.

20. The cartridge according to claim 4, wherein the cartridge further comprises a siphon tube (120), the sample addition compartment (110) and the sample lysis compartment (130) communicate with each other through the siphon tube (120).

21. The cartridge according to claim 20, wherein a first choke valve (801) is provided in the siphon tube (120); the first choke valve (801) is configured to control the flow or blocking of the sample and/or air between the sample addition compartment (110) and the sample lysis compartment (130).

22. The cartridge according to claim 1, wherein the first reagent is a first lyophilized bead (610).

23. The cartridge according to claim 22, wherein the first lyophilized bead (610) comprises an excipient, the weight of the excipient accounts for 20%-60% of the total weight of the first lyophilized bead (610).

24. The cartridge according to claim 6, wherein the cartridge further comprises a lid (400), the lid (400) is configured to cap the cassette sample addition nozzle (300); and the lid (400) is provided with a step (401), the step (401) and a through-hole (301) of the cassette sample addition nozzle (300) are in an interference fit.

25. The cartridge according to claim 10, wherein the pneumatic module further comprises a second air hole (202) and a first air compartment (910);

said first air hole (201) and the second air hole (202) are located in the first air compartment (910), the first air hole (201) communicates with the first air channel (210) through the second air hole (202); and said first waterproof and breathable film (1510) is sealed over the first air hole (201) and the second air hole (202); a sealing film is provided at an outer side of the first waterproof and breathable film (1510), so that the first air hole (201) and the second air hole (202) exchange air within the first air compartment (910).

26. The cartridge according to claim 11, wherein the pneumatic module further comprises a fourth air hole (204), a second air channel (220) and a third air channel (230);

one end of the third air hole (203) communicates with the second air pump, one end of the second air channel (220) communicates with the other end of the third air hole (203); the second air channel (220) communicates with the third air channel (230) through the fourth air hole (204); the third air channel (230) communicates with the fifth air hole (205); and the third air channel (230) and one end of the third air hole (203) that communicates with the second air pump are located at one surface of the cartridge, the second air channel (220) and the third air channel (230) are located at a surface opposite to the cartridge.

* * * * *